United States Patent
Õunap et al.

(10) Patent No.: US 12,195,751 B2
(45) Date of Patent: *Jan. 14, 2025

(54) PLATFORM FOR DEVELOPING STABLE MAMMALIAN CELL LINES

(71) Applicant: Icosagen Cell Factory OÜ, Tartumaa (EE)

(72) Inventors: Kadri Õunap, Õssu (EE); Eva-Maria Tombak, Õssu (EE); Mart Toots, Õssu (EE); Madis Jakobson, Õssu (EE); Mart Ustav, Jr., Õssu (EE); Kerttu Murumets, Õssu (EE); Urve Toots, Õssu (EE); Andres Männik, Õssu (EE); Mart Ustav, Sr., Õssu (EE)

(73) Assignee: Icosagen Cell Factory OÜ, Õssu (EE)

(*) Notice: Subject to any disclaimer, the term of this patent is extended or adjusted under 35 U.S.C. 154(b) by 0 days.

This patent is subject to a terminal disclaimer.

(21) Appl. No.: 18/314,979

(22) Filed: May 10, 2023

(65) Prior Publication Data

US 2023/0340542 A1 Oct. 26, 2023

Related U.S. Application Data

(62) Division of application No. 16/655,717, filed on Oct. 17, 2019, now Pat. No. 11,685,936.

(60) Provisional application No. 62/747,158, filed on Oct. 18, 2018.

(51) Int. Cl.
| | | |
|---|---|---|
| C12N 15/85 | (2006.01) | |
| C12N 15/10 | (2006.01) | |
| C12N 15/90 | (2006.01) | |

(52) U.S. Cl.
CPC ....... *C12N 15/907* (2013.01); *C12N 15/1024* (2013.01); *C12N 15/85* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 11,685,936 B2 * | 6/2023 | Õunap | C12N 15/1024 435/462 |
|---|---|---|---|
| 2003/0013157 A1 | 1/2003 | Jakobovits et al. | |
| 2003/0129169 A1 | 7/2003 | Krohn et al. | |

OTHER PUBLICATIONS

Groskreutz et al., Methods in Molecular Biology, Recombinant Protein Protocols Detection and Isolation, vol. 63, pp. 11-30, 1997 (Year: 1997).*
Minskaia et al., BioMed Research International 2013:291730, 2013, 12 pages (Year: 2013).*
Bebbington, C.R. et al., High-lever expression of a recombinant antibody from myeloma cells using a glutamine synthetase gene as an amplifiable selectable marker, Biotechnol. Nature Publishing Group, Feb. 1992, pp. 169-175, vol. 10.
Frye, Christopher et al., Industry view on the relative importance of "clonality" of biopharmaceutical-producing cell lines, Biologicals, 2016, pp. 117-122, vol. 4 Issue 2.
Inniss, Mara C. et al., A novel Bxb1 integrase RMCE system for high fidelity site-specific integration of mAb expression cassette in CHO cells, Biotechnology and Bioengineering, 2017, pp. 1837-1846, vol. 114.
Kaufman, Randal J. et al., Amplification and expression of sequences cotransfected with a modular dihydrofolate reductase complementary DNA gene, J. Mol. Biol., 1982, pp. 601-621, vol. 159.
Kim, Min Soo et al., Use of Flp-Mediated Cassette Exchange in the Development of a CHO Cell Line Stably Producing Erythropoietin, Journal of Microbiology and Biotechnology, Mar. 2008, pp. 1342-1351, vol. 18 Issue 7.
Liu, Pei-Qi et al., Generation of a Triple-Gene Knockout Mammalian Cell Line Using Engineered Zinc-Finger Nucleases, Biotechnology and Bioengineering, Dec. 2009, pp. 97-105, vol. 106, Issue 1.
Urlaub, Gail et al., Isolation of Chinese hamster cell mutants deficient in dihydrofolate reductase activity, Proceedings of the National Academy of Sciences of the United States of America, Jul. 1980, pp. 4216-4220, vol. 77 Issue 7.
Wigler, M. et al., Transformation of mammalian cells with an amplifiable dominant-acting gene, Proceedings of the National Academy of Sciences of the United States of America, Jun. 1980, pp. 3567-3570, vol. 77 Issue 6.
Zhang, Lin et al., Recombinase-Mediated Cassette Exchange (RMCE) for Monoclonal Antibody Expression in the Commercially Relevant CHOK1SV Cell Line, Biotechnology Progress, Sep. 2015, pp. 1-12, vol. 00 Issue 00.
Zhu, Jianwei, Mammalian cell protein expression for biopharmaceutical production, Biotechnology Advances, 2012, pp. 1158-1170, vol. 30 Issue 5.

(Continued)

*Primary Examiner* — David Steadman
(74) *Attorney, Agent, or Firm* — Koivula & Somersalo, LLC

(57) ABSTRACT

This disclosure provides methods and landing pad constructs for generation of parental cell lines suitable for targeted integration. A method is provided by the parental cell line development; this is, the introduction of binding sites of BPV1 E2 protein to landing pad vectors so that expressed BPV1 E2 protein could locate the vector to transcriptionally active region in the genome. Cells with high expression level of reporter genes are selected for the next stage and will be used in the development of cell lines expressing another recombinant protein by recombination mediated cassette exchange (RMCE). Landing pad constructs include recombination target sites for site-specific recombinases, and therefore, it could be replaced with gene-of-interest expression construct containing the same set of recombination target sites. This yields the generation of producer cell lines with less effort compared to traditional cell line development by random integration.

13 Claims, 11 Drawing Sheets

Figure 1:
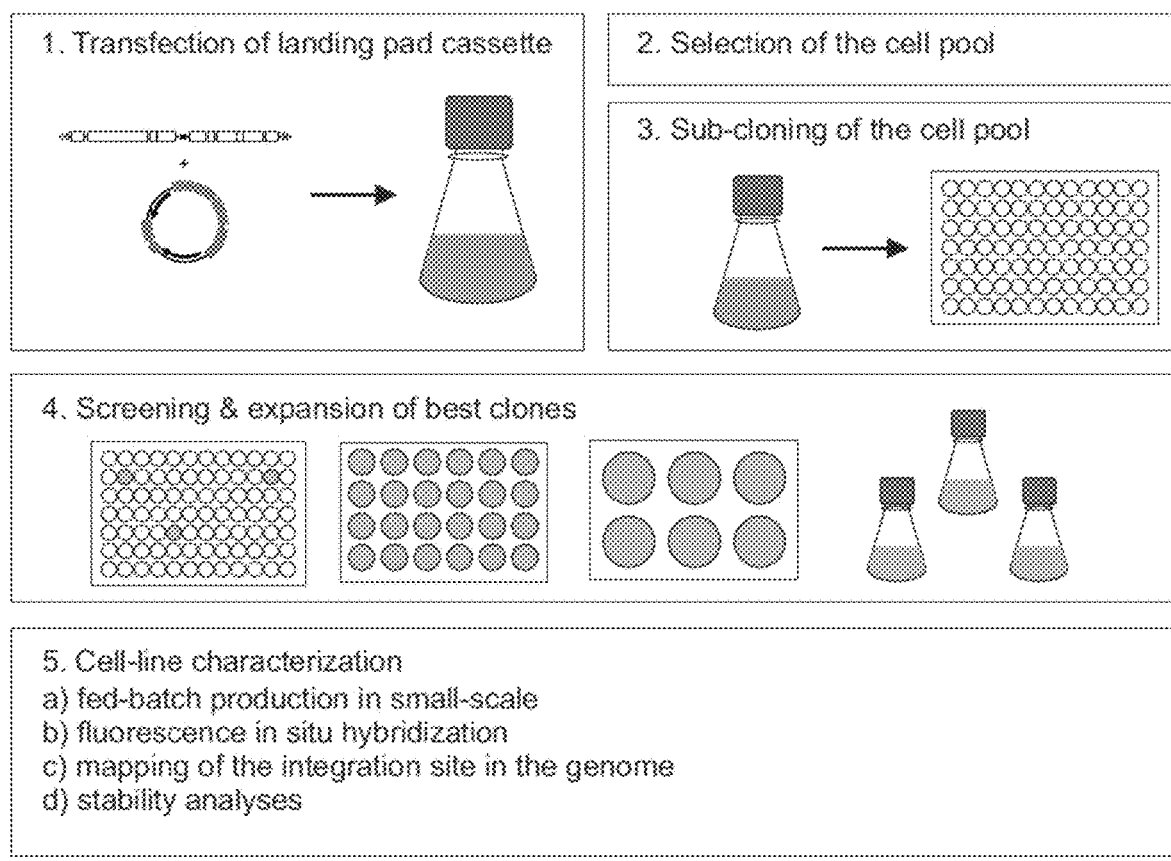

Specification includes a Sequence Listing.

(56) References Cited

OTHER PUBLICATIONS

O'Brien et al., Biotechnol. J. 13:e1800226, Jul. 2018, 10 pages (Year: 2018).
Sultana et al., Nat. Rev. Genet. 18:292-308, 2017 (Year: 2017).
Jang et al., J. Viral. 83:2592-2600, 2009 (Year: 2009).
Kurg, R., "DNA Replication—Current Advances", pp. 613-638, 2011 (Year: 2011).
Kim et al., Biotechnol. Bioprocess Engineer. 13:418-423, 2008 (Year: 2008).
Baker, Carl.C. 1987. Structural and transcriptional analysis of human papillomavirus type 16 sequences in cervical carcinoma cell lines. Journal of Virology. Vol. 61, No. 4. pp. 962-971.
Goodwin, Edward C. and Dimaio, Daniel. 2000. Repression of human papillomavirus oncogenes in HeLa cervical carcinoma cells causes the orderly reactivation of dormant tumor suppressor pathways. Proc. Natl. Acad Sci USA, Nov. 7, 200, vol. 97, No. 23 pp. 12513-12518.
Hwang, Eun-Seon; David J Reise II, Jeffety Settlemenn, Laura A. Nilson, Julie Honig, Stuart Flynn, and Daniel Dimaio. 1993. Inhibition of cervical carcinoma cell line proliferation by the introduction of a bovine papilloma regulatory gene Journal of Virology vol. 67 No. 7 pp. 3720-3729.
Romantczuk, Helen and Peter M. Howley. 1992. Distribution of either the E1 or the E2 regulatory gene of human papillomavirus type 16 increases viral immoralization capacity. Proc. Natl. Acad. Sci. USA vol. 89. pp. 3159-3163.
Schneider-Maunoury, Odile Coissant and Gerard Orth. 1987. Integration of human papillomavirus type 16 DNA sequences: a possible early event in the progression of genital tumors. Journal of Virology. vol. 61. No. 10. pp. 3295-3298.
Wells Susanne I, Delicia a. Francis, Alla Y. Karpova, Jennifert J. Dowhanick, John D Benson, Peter M. Howley. 2000. The EMBO Journal vol. 19, No. 21 pp. 5762-5771.
Lehman Chris W. and Michael R. Botchan. 1998. Segregation of viral plasmids depends on tethering to chromosomes and is regulated by phosphorylation. Proc. Natl. Acad. Sci. USA vol. 95. pp. 4338-4343.
Sciadopoulos, Mario H and Alison A McBride. 1998. Bovine papilloma type 1 genomes and the E2 transactivator protein are closely associated with mitotic chromatin. Journal of Virology vol. 72, No. 3. pp. 2079-2088.
Ilves Ivar, Sirje Kivi, and Mart Ustav. 1999. Long-term episomal maintenance of bovine paipllomavirus type 1 plasmids is determined by attachment to host chromosomes, which is mediated by the viral E2 protein and its binding sites. Journal of Virology vol. 73, No. 5, pp. 4404-4412.
Desaintes Christian, Sylvain Goyat, Serge Garbay, Moshe Yaniv, and Francoise Thierry. 1999. Papillomavirus E2 induces p53-independent apoptosis in Hela cells. Ocongene 18, 4538-4545.

\* cited by examiner

A
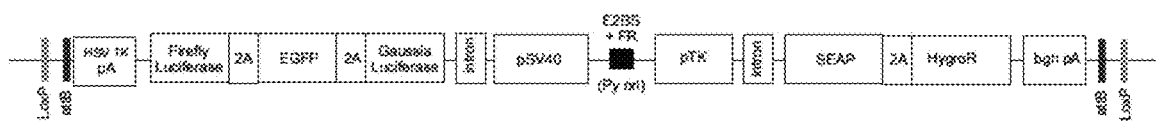
B
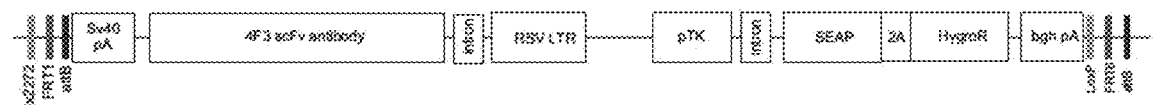
C
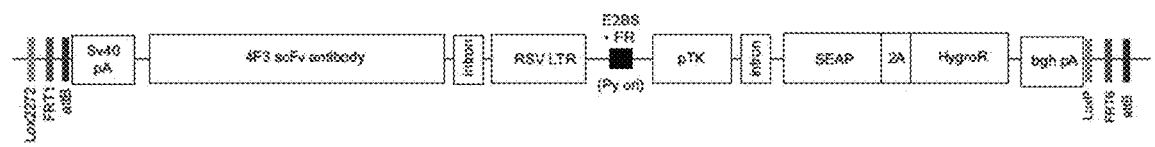
D
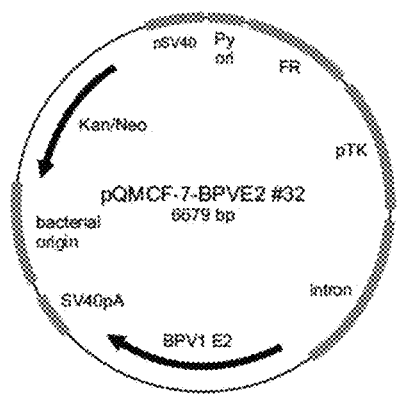
FIGS. 2(A), 2(B), 2(C), and 2(D)

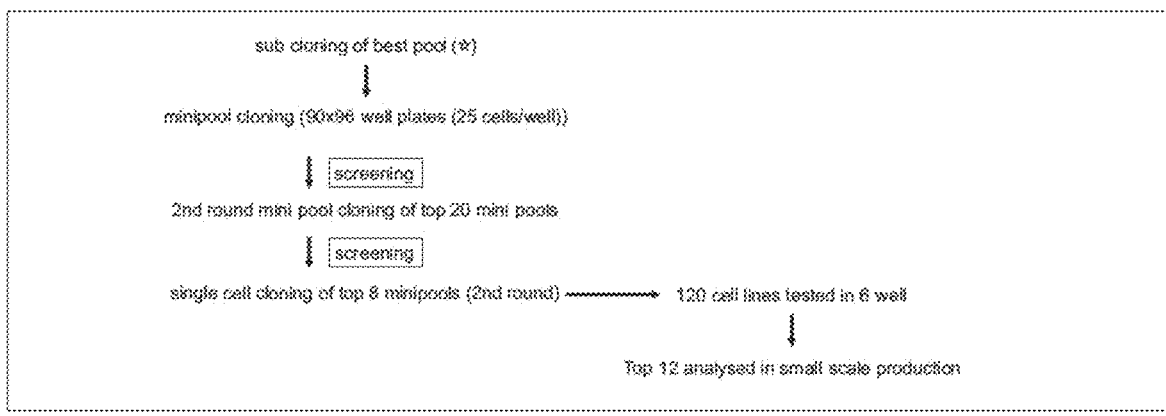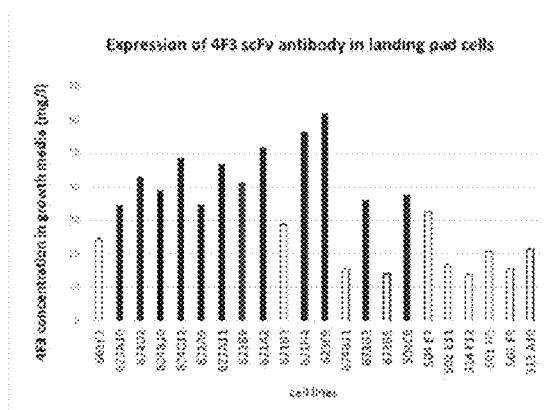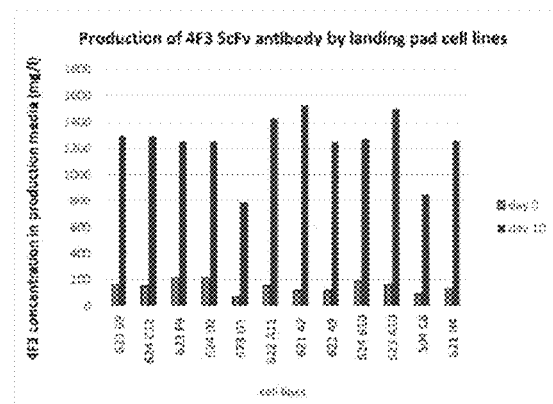
FIGS. 4(A), 4(B), and 4(C)

A

B

| Pool no | Recombination plasmid (ng) | recombinase mRNA (μg) | targeted integration (%) | targeted + random integration (%) | random integration, 1-2 integration sites (%) | random integration, <2 integration sites (%) |
|---|---|---|---|---|---|---|
| 1 | 100 | 1 | 21 | 15 | 54 | 10 |
| 2 | 300 | 1 | 26 | 15 | 32 | 27 |
| 3 | 1000 | 1 | 25 | 16 | 21 | 38 |
| 4 | 100 | 3 | 22 | 11 | 55 | 12 |
| 5 | 300 | 3 | 42 | 19 | 21 | 18 |
| 6 | 1000 | 3 | 31 | 24 | 24 | 21 |

PLATFORM FOR DEVELOPING STABLE MAMMALIAN CELL LINES

PRIORITY

This application is a divisional application of U.S. patent application Ser. No. 16/655,717 filed on Oct. 17, 2019 and claiming priority to U.S. provisional application No. 62/747,158 filed on Oct. 18, 2018; both of which are incorporated herein by reference.

SEQUENCE LISTING

The sequence listing entitled as 11344-008US2_sequence_listing.XML, created on May 9, 2023, and having a file size of 95,032 bytes is hereby incorporated by reference pursuant to 37 C.F.R. section 1.52(e) (5).

BACKGROUND OF THE INVENTION

About 20-30% of new drugs approved by European Medicines Agency (EMA) and US Food and Drug Administration (FDA) are biologics (biopharmaceuticals, biotherapeutics). In addition to approved biopharmaceuticals, a large number of biologic drugs are under development and in the pipeline for approval. To produce these products in large quantities, good and robust expression systems are needed for discovery, development and manufacturing of drug candidates.

Production of therapeutic proteins such as monoclonal antibodies, peptides and recombinant proteins is challenging as most of the biologics are proteins with complex post-translational modifications. To achieve proper modification, protein production using mammalian cells is required. Chinese hamster ovary (CHO) cells are used for the majority of products, both on the market and in clinical development, as the products produced in these cells are safe, efficient, and have a similar glycosylation pattern as human proteins (Zhu, 2012). In addition, CHO cells can grow in chemically defined serum-free media and cultivated in suspension culture, meaning that the protein production in CHO cells can easily be scaled-up which is crucial for industrial manufacturing of therapeutics.

To continuously produce biologics, stable high-producer cell lines need to be generated. Historically, such cell lines have been produced by random integration of gene-of-interest expression cassette to the genome, followed by selection with antibiotic compound and cassette amplification using either glutamine synthetase/MSX or dihydrofolate reductase/MTX systems (Bebbington et al., 1992; Kaufman and Sharp, 1982). For both systems, knock-out cell lines have been generated (Liu et al., 2010; Urlaub and Chasin, 1980; Wigler et al., 1980). However, stable cell line development using gene amplification approach is time consuming and always requires lot of effort as the selected pools are heterogeneous. Single-cell cloning of selected pools is necessary to identify rare high-producer clones. Furthermore, proofing of "monoclonality" of production cell line is required for the safety and efficiency of the produced protein (Frye et al., 2016). Stability of generated cell line(s) can be tested in the end of development and unfortunately, due to lack of control of insertion sites in random integration, protein productivity of some clones could be high in the beginning of the development but may diminish over time, causing instability of cell lines. This means that several clonal cell lines need to be generated and tested for further stability studies which naturally makes development work slow and expensive.

Accordingly, cell line development with classical random integration is a long and costly process. Mostly, the high cost is caused by large number of clones that need to be screened in order to get a suitable cell line and therefore, development of cell lines for production of therapeutics in large-scale is often unaffordable for small and medium size enterprises. Use of site-specific or targeted integration that improves development efficiency is a promising strategy which could reduce the price of stable cell line generation. Therefore, there is a need for new cell line development technologies, based on the targeted integration of a transgene for decreasing the number of clones to be screened and by that, to reduce the price of whole process.

Several enzymes can be used to achieve targeted integration of a transgene expression cassette to the cells—e.g., site-specific recombinases (Cre, Flp or BxB1), engineered nucleases (TALENs or zinc-finger nucleases), or the most recently developed tool, CRISPR-Cas9 system. The usage of site-specific recombinases like Cre, Flp or BxB1 needs introduction of specific recognition sequence(s) to the host cell genome and after that, the gene-of-interest expression cassette can be targeted into the same locus. For example, in the Flp-in system provided by Thermo Fisher Scientific, a single Flp-recognition (FRT) site is introduced in host genome to integrate the expression plasmids containing the same recognition site. However, with this type of integration, together with a gene-of-interest sequence, unnecessary plasmid backbone consisting of bacterial origin of replication and antibiotic resistance gene that were used for molecular cloning purposes also integrate to eukaryotic cell genome. Bacterial sequences are unwanted in eukaryotic cells because their presence can lead to silencing of the locus of integration. However, if there are 2 different or incompatible recombinase target sites (e.g., a wild-type and a mutant site) in the host cells, the gene-of-interest expression vector containing the same set of recombination sites can be integrated by the recombination-mediated cassette exchange (RMCE) reaction. RMCE leads to replacement of the sequence between the recombination sites and to the excision of the regions outside of the recombination sites. RMCE does not leave behind extraneous vector sequences such as bacterial origin of replication and antibiotic resistance cassette needed for plasmid amplification in bacteria, as these elements can be placed outside of the recombination target sites. The use of recombinase mediated cassette exchange allows avoiding the integration of unnecessary regions into the mammalian cell genome. Therefore, transgene silencing, caused by co-integration bacterial elements, should not occur in RMCE cell line.

Some CHO based parental cell lines that can be used for stable cell line development through RMCE have already been shown to have good productivities of monoclonal antibodies after recombination (Inniss et al., 2017; Zhang et al., 2015). However, the repertoire of different cell lines is scarce and only a very few genomic hotspots in CHO cells such as Fer1L4 locus, have been tested in terms of productivity and stability (Zhang et al., 2015). Thus, there is still demand for new parental cell lines containing integrated transgene in genomic hotspots.

In addition, the systems that help to target the transgenes to the transcriptionally active region are also needed for identifying superior genomic loci suitable for stable cell line development. Furthermore, it is crucial to uncover the mechanisms that help to increase the stable and transient expression of therapeutics in mammalian cells.

SUMMARY OF THE INVENTION

Here, a mammalian cell-based technology that allows for faster and more efficient production of recombinant proteins and biologic drugs compared to traditional random integration cell line development methods is disclosed. By creating parental landing pad cell lines that express the integrated reporter genes at high-yield for a long period of time and use these parental cell lines as platforms for making cell lines that produce protein of interest in a similar manner, it is possible to reduce the price of stable cell line development.

The present invention provides methods and constructs for developing parental cell lines that can be used for targeted integration to produce cell lines expressing protein-of-interest, such as antibodies or other recombinant proteins.

The parental cell lines are developed similarly to traditional methods, by random integration of the expression cassette to the cells. However, here an advantage is taken of the properties of the master transcriptional regulator of papillomaviruses, which is the E2-protein. Many different DNA viruses, including papillomaviruses, replicate as extra-chromosomal episomes. For efficient gene expression and replication, episomal viral genomes should be located to transcriptionally active regions of chromatin. The viral genomes are often transferred to these regions by viral proteins (e.g., BPV1 E2) that bind to their respective binding-sites (BS) located on viral genome. Here, we show that by inserting papillomavirus (e.g BPV1) E2 binding sites to landing pad cassette, in the presence of viral protein expression, the landing pad cassette is directed to transcriptionally active region of the chromatin prior to integration. E2 binding sites were added in the landing pad cassettes and when an BPV1 E2 expression vector is co-transfected with the landing pad or any other DNA that contains E2 binding sites (E2BS), it is possible to tether the vector to the transcriptionally active chromatin locus and thereby increase the chance that the construct integrates into an active genomic region ensuring stable high-yield expression of the integrated sequences.

Accordingly, it is an object of this invention to provide co-transfection of BPV1 E2 expression cassette and landing pad construct containing BPV1 E2 binding sites leading to generation of cell pools with higher expression of the reporter gene as compared to landing pads without the BPV1 E2 binding sites.

It is an object of the present invention to provide plasmid DNA sequence encoding bovine papillomavirus E2 protein for use in parental cell line development.

A further object of this invention is to provide increase in transcriptional activity of promoters that are in the proximity of BPV1 E2 binding sites, when the expression cassette of E2 protein is stably integrated to the cells and the cell line is expressing this protein.

It is an object of this invention to provide landing pad cassettes expressing detectable reporter genes for easy screening by high-throughput methods. These cassettes are flanked by recognition sites of site-specific recombinases, which makes it possible to replace the cassette with another vector containing the same set of recognition sequences in a recombination-mediated cassette exchange (RMCE) reaction. For targeted integration via RMCE, the gene-of-interest vector needs to be co-transfected with either the expression vector or mRNA of a site-specific recombinase. Compared to parental cell line development by random integration, the generation of protein of interest cell line via targeted integration takes less time and energy since less clones need to be screened to find clones with suitable stability and productivity.

It is an object of this invention to provide high producer gene of interest (GOI) cell lines.

Another object of the invention is to provide parental cell lines containing integrated landing pad vector for use in development of high producer GOI-cell lines.

It is an object of this invention to provide landing pad vectors including recognition sites of site-specific recombinases. According to certain aspects of the invention the recognition sites may be Cre, Flp and BxB1 sites. According to certain aspects the landing pad vectors encode one or more reporter proteins, enabling the screening of best producing clones.

According to certain aspects based on the expression of reporter genes, the clonal cell lines with high-yield expression of reporter genes can be screened out to generate the parental cell lines.

According to certain aspects of the parental cell lines will be characterized and the well-described parental cell lines with a single integration of the landing pad vector are used in recombination-mediated cassette exchange to replace the landing pad vector with a gene-of-interest expression vector to generate the cell line with similar properties as the parental cells.

Accordingly, it is an object the invention to provide:

A landing pad construct having recognition sites of site-specific recombinases at both of its ends, and comprising: coding sequences for at least one reporter gene coding for a detectable reporter protein, coding sequences for at least one selection marker and papillomavirus E2 binding sites.

It is another object of the invention to provide a landing pad plasmid having a nucleotide sequence according to SEQ ID NO:1; SEQ ID NO:2 or SEQ ID NO:3.

It is an object to provide a cell line, comprising a landing pad plasmid having recognition sites of site-specific recombinases at both of its ends, and comprising: coding sequences for at least one reporter gene coding for a detectable reporter protein, coding sequences for at least one selection marker and coding sequences for BPV 1 E2 binding site.

A further object of the invention is to provide a cell line co-transfected with a landing pad plasmid having recognition sites of site-specific recombinases at both of its ends, and comprising: coding sequences for at least one reporter gene coding for a detectable reporter protein, coding sequences for at least one selection marker and coding sequences for BPV 1 E2 binding site and with an expression vector for BPV E2 protein.

It is another object of the invention to provide a method to develop high producer cell lines, said method comprising the steps of: providing a landing pad vector flanked by recognition sites of site-specific recombinases, and comprising coding sequences for at least one reporter gene and for papillomavirus E2 binding sites; providing an expression plasmid of BPV1 E2 protein; co-transfecting a cell with the landing pad vector and the expression plasmid; allowing expression from the landing pad vector and the expression vector, whereby targeting of the landing pad vector to transcriptionally active regions of the chromatin is improved; and selecting the cells with highest production a parental cell lines.

Still another object of the invention is to provide a method for high stable production of a gene of interest, said method comprising the steps of developing a high producer cell line by way of co-transfecting a cell line with a landing pad vector flanked by recognition sites of site-specific recombinases, and comprising coding sequences for at least one reporter gene and for BPV1 E2 binding site, and with an expression plasmid of BPV1 E2 protein; providing a gene of interest vector comprising same recognition sites of site-specific recombinases as the landing pad vector; replacing the landing pad vector with the gene of interest vector by co-transfecting the cell line with the gene of interest vector and an expression vector or mRNA for site-specific recombinases recognized by the recognition sites, and cultivating the cell line in environment suitable for protein expression.

It is yet another object of this invention to provide a kit comprising, a landing pad vector flanked by recognition sites of site-specific recombinases, and comprising coding sequences for at least one reporter gene and for BPV1 E2 sites and with an expression plasmid of BPV1 E2 protein(s); a gene of interest vector comprising same recognition sites of site-specific recombinases as the landing pad vector; and a suitable cell line for co-transfection.

Further objects and aspects of the invention are described in the following drawings and detailed disclosure of the invention.

SHORT DESCRIPTION OF THE FIGURES

FIG. 1. Generic scheme of landing pad cell line development. Each box on the scheme characterizes one stage in a classical stable cell line development process.

FIG. 2. Schemes of constructs used in parental cell line development. A) LP2str #132; B) LP2str_4F3_wo BS #3; C) LP2str_4F3_CAR #182; D) pQMCF-7-BPVE2 #32. Panels A-C illustrate different landing pad constructs that are flanked by recombination target sites and encode for detectable reporter genes and antibiotic resistance gene. These cassettes can be used in parental cell line development for identifying suitable clonal cell lines that can later be used for protein of interest cell line generation. Panel D illustrates pQMCF-7-BPVE2 #32 vector encoding for BPV1 E2 protein that enables targeting the landing pad vectors to transcriptionally active region.

Figure 3:
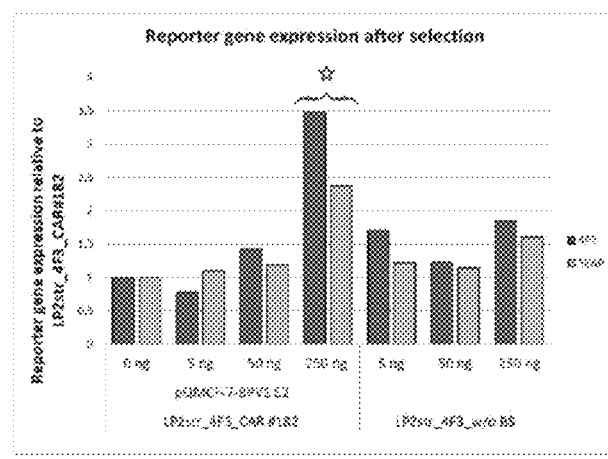

FIG. 3. ELISA assay for evaluating the role of BPV1 E2 in reporter gene 4F3 scFv expression in selected cell pools. Results are presented relative to LP2str_4F3_CAR #182 transfection. Marked cell pool, expressing 4F3 scFv at highest level, was selected to be used in parental cell line development.

FIG. 4. Example of a landing pad cell line generation. A) Scheme of the screening of high-producer cell line. The selected pool with highest expression of reporter gene was divided to mini-pools followed by single-cell cloning of best mini-pools based on the reporter gene expression. For final screening, the cell densities in 6-well plate were normalized and after 2 days, media was collected for the ELISA analysis. B) ELISA assay for measuring 4F3 expression in 6-well plate. C) The small-scale fed-batch culture production analysis of top 12 clonal cell lines. Length of production was 10 days, production supernatants were analyzed by Octet K2.

Figure 5:
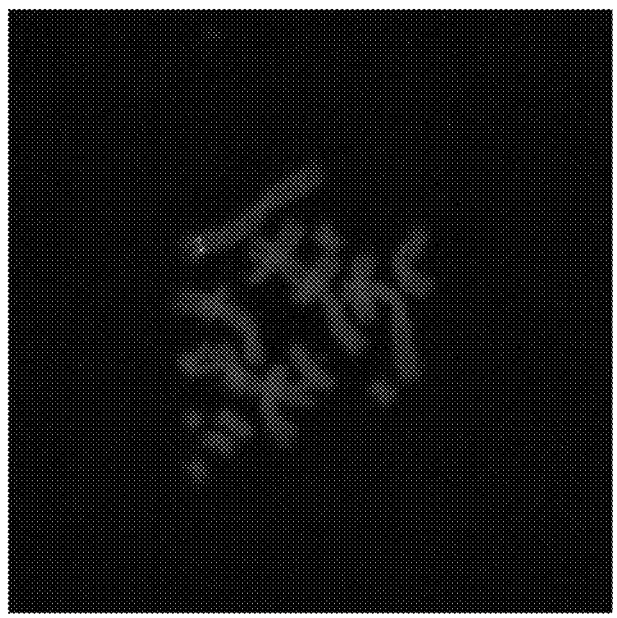

FIG. 5. Characterization of #504C6 landing pad cell line by fluorescence in situ hybridization. Metaphase chromosomes were hybridized with biotin labeled landing pad vector LP2str_4F3_CAR #182, signal was amplified with Tyramide signal amplification kit and detected with HRP-Streptavidin and Alexa Fluor™ 488 Tyramide. Here, the #504C6 cell line was characterized as having a single integration site.

Figure 6:
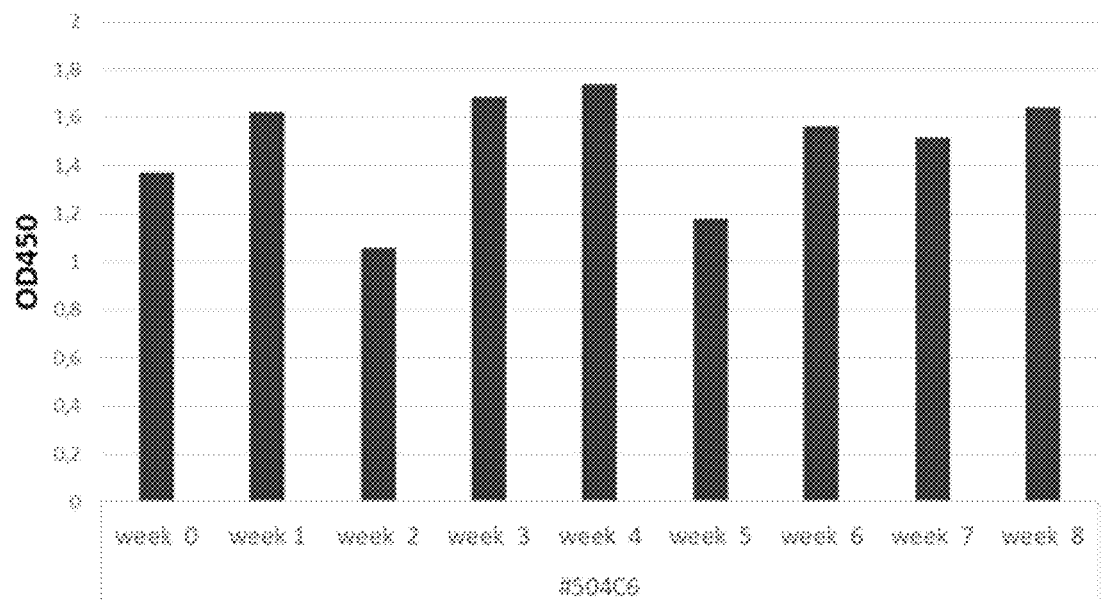

FIG. 6. Stability analysis of 4F3 expression in #504C6 landing pad cell line. For stability analysis, #504C6 cell line was cultivated for 8 weeks. Each week, cells were counted and seeded with density ($5 \times 10^5$ cells/ml) and 2 days later, the samples from cell culture media were collected. 4F3 scFv expression analysis was conducted by ELISA, x-axis presents absorbance at 450 nm.

Figure 7A:
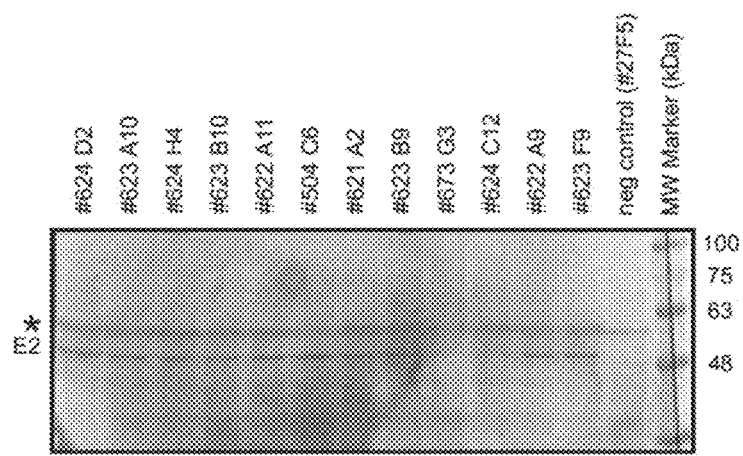

FIG. 7. The presence of BPV1 E2 protein in the landing pad cell lines increases the expression from promoters in the proximity of E2 binding sites. A) Western blot analysis of the expression of BPV1 E2 protein in landing pad cell lines. The mixture of in-house developed antibodies against BPV1 E2 protein (#1E4 and #3E8) was used for detection. E2 marks the BPV1 E2 protein and * marks the unspecific protein recognized by E2 antibody. B) The presence of BPV1 E2 binding sites in the proximity of promoters driving the transcription of recombinant protein (as an example human transferrin, but any preferred protein may be expressed) has positive effect on the expression level of these proteins. Western blot analysis detecting human transferrin expression in BPV1 E2 positive landing pad cell line #504C6 3 days after transfection. Plasmids with (+) or without (−) BPV1 E2 binding sites in front of heIF4A1 and hEF1α promoters driving hTF expression were analyzed. The expression of reporter antibody 4F3 scFv is also detectable, as the secondary antibody recognizing the hTF antibody cross-reacts with human scFV antibody.

FIG. 8. Optimization of recombination efficiency in landing pad cell lines. A) Scheme for the gene of interest (GOI) cell line development experiment for finding suitable conditions for recombination. CHO cells were transfected with different amounts of plasmid DNA (100 ng, 300 ng or 1000 ng) or recombinase mRNA (1 or 3 μg), followed by selection with antibiotics and recovery of pools. B) Estimation of recombination efficiency by fluorescence in situ hybridization (FISH). At least 100 metaphase cells were examined for each pool to calculate the frequencies of targeted integration, targeted integration with additional random integration of the recombination cassette, or random integration events with up to 2 or more integration sites. Cell pool transfected with 3 μg Cre mRNA and 300 ng pGOI had highest frequency of targeted integration and lowest frequency of random integration and was selected for use in single-cell cloning by limiting dilution.

Figures 9A, 9B:
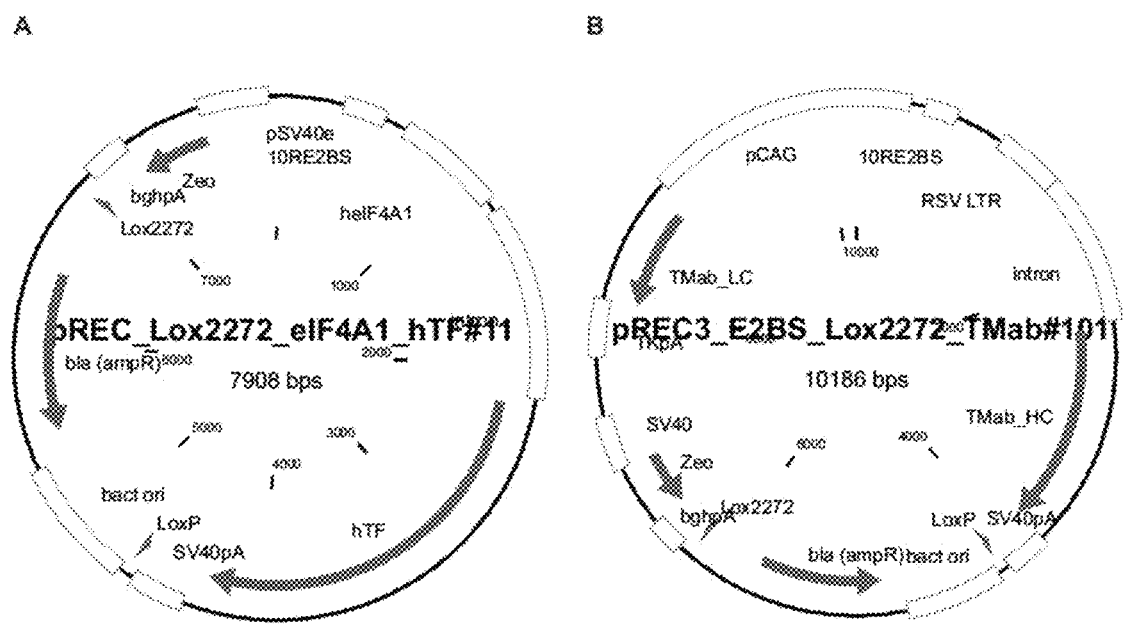

FIG. 9. The schemes of exchange vectors A) single-cassette gene-of-interest expression vectors used for targeted integration. B) double-cassette gene-of-interest expression vector suitable for targeted integration.

FIG. 10. The production of recombinant protein (e.g. human transferrin) in cell lines generated from #504C6 parental cell line. The clonal cell lines were generated by limiting dilution of the pool with highest frequency of targeted integration, followed by screening of the loss of reporter gene in 96-well format. The cell lines with no expression of the reporter antibody (4F3) were expanded to 24-well, 6-well and then to 125 ml shaker flask, after which the fed-batch production was performed. Supernatants were analyzed by SDS-PAGE (A) and ELISA (B). A) SDS-PAGE analysis of the fed-batch production supernatants collected in the end of production; B) ELISA analysis of the fed-batch production supernatants collected in the end of production. Productivity of human transferrin by these cell lines (mg/l) was calculated.

Figure 11:
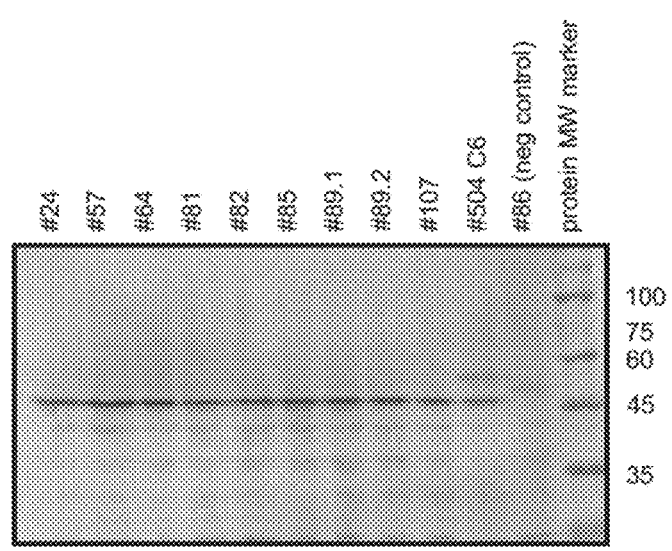

FIG. 11. BPV1 E2 protein is expressed in the human transferrin cell lines generated from #504C6 cell line by RMCE. The expression of BPV1 E2 protein is evaluated by immunoblot. The lysate of ~50 000 cells was separated by SDS-PAGE and transferred to PVDF membrane. For detection, the mixture of in-house developed antibodies against E2 protein (#1E4 and #3E8) were used at concentration 1 µg/ml.

DETAILED DESCRIPTION OF THE INVENTION

Definitions

In this disclosure the following terms are used as defined below:

"A gene of interest" refers to a cDNA encoding a gene product of interest such as a protein of interest or recombinant protein of interest.

```
"attB" refers to nucleotide sequence
                                    (SEQ ID NO: 9)
GGTTTGTCTGGTCAACCACCGCGGTCTCAGTGGTGTACG

GTACAAACC.

"attP" refers to sequence
                                    (SEQ ID NO: 10)
GGCTTGTCGACGACGGCGGTCTCCGTCGTCAGGATCAT.
```

"BPV1" refers to bovine papillomavirus type I.

"E2" refers to a protein encoded by nucleotides 2594-3837 of BPV subtype 1.

"E2BS" refers to bovine papillomavirus E2 protein binding sites.

"EGFP" refers to Enhanced Green Fluorescent Protein.

"FLuc" refers to Firefly Luciferase.

"FR" refers to Family of Repeats, Epstein Barr virus EBNA1 protein binding site.

```
"FRT1" refers to recombinase
recognition sequence of Flp
                                    (SEQ ID NO: 7)
GAAGTTCCTATTCCGAAGTTCCTATT

CTCTAGAAAGTATAGGAACTTC

"FRT6" refers to modified recombinase
recognition sequence of Flp
                                    (SEQ ID NO: 8)
GAAGTTCCTATTCCGAAGTTCCTAT

TCTTCAAAAGTATAGGAACTTC.
```

"GLuc" refers to *Gaussia* luciferase.

"landing pad cell line" refers to a mammalian cell line, that contains the integrated landing pad cassette.

"landing pad" refers to plasmids that contain recognition sequences for site-specific recombinases (suitable recombinases are e.g., BxB1 integrase, Flp or Cre recombinase, but it is to be noted that other recombinases may also be used), expression cassettes of reporter genes (suitable reporter genes are secreted alkaline phosphatase (SEAP), *Gaussia* luciferase, Firefly luciferase, enhanced green fluorescent protein (EGFP) and/or in-house developed single chain antibody 4F3, but it is to be noted that other reported genes may also be used), and expression cassettes for proteins giving resistance to selection antibiotics. Some but not all "landing pad" vectors contain binding sites for BPV1 E2 protein and/or binding sites for EBV EBNA 1 binding sites.

"Lox2272" refers to 34 nucleotide sequence ATAACTTCGTATAAaGTATcCTATACGAAGTTAT (SEQ ID NO:6) which contains 2 altered residues compared to LoxP sequence.

"LoxP" refers to 34 nucleotide sequence ATAACTTCGTATAATGTATGCTATACGAAGTTAT (SEQ ID NO: 5) found on bacteriophage P1. This is a recombination target site of Cre recombinase of bacteriophage P1;

"pyORI" refers to polyomavirus replication origin.

"RMCE" refers to Recombination Mediated Cassette Exchange, facilitated by site-specific recombinase enzymes such as but not limited to Cre, Flp or BxB1.

"SEAP" refers to Secreted Alkaline Phosphatase

The present disclosure provides a method and constructs for development of stable mammalian cell lines for protein production. The mammalian cells may be CHO cells, but other cell lines such as HEK 293, NS0, Sp2/0 are also possible. The methods and constructs of this disclosure can be used to generate host cells for targeted integration. These host cells or landing pad cells contain expression cassettes of reporter genes, selection markers and recognition sites for site-specific recombinases. Based on the expression of the reporter genes and their stability in time, the best parental cell lines can be selected and thoroughly characterized. After this, cell lines expressing protein-of-interest are generated from suitable parental cell line. For this, site-specific recombinases are used in recombination mediated cassette exchange (RMCE) through recombinase target sites flanking the landing pad cassette and recombination vectors.

It was surprisingly found that E2 protein enables generating stable cell pools with high expression level of reporter genes when landing pad constructs containing BPV1 E2 binding sites are used. Therefore, the present invention provides constructs and methods for co-transfecting BPV1 E2 protein together with the landing pad construct, so that landing pad cell pools with higher expression level of reporter genes can be generated.

According to one aspect of the invention methods and constructs for generation of host cells for targeted integration by using landing pad constructs that contain binding sites for BPV1 E2 protein are provided.

According to one aspect recombination plasmids and mechanisms for targeted integration of the gene-of-interest (GOI) expression vectors to the parental mammalian cell lines are provided.

An advantage of the present invention is reduction of the length of cell line development process compared to classical random integration approach and decrease the cost of the process as less cells/plates need to be screened.

According to one aspect of the invention the bovine papillomavirus type I protein E2, the main transcriptional regulator of BPV1 helps to activate the transcription of promoters in the proximity of E2 binding sites in mammalian cells, including but not limited to CHO-S cells. By regulating transcription through E2 binding sites, BPV1 E2 supports the increase of recombinant protein expression level in E2 positive cell line.

Landing Pad Cell Line Development

Landing pad constructs of this disclosure with all necessary elements are shown in FIG. 2. The landing pad cell line development (schematically characterized in FIG. 1) is performed according to classical random integration approach. The process consists of 5 steps and starts with introduction of linearized landing pad expression cassette into the cell by transfection (e.g., electroporation) and is followed by stable pool selection which starts at 3-5 days after transfection. Antibiotic selection lasts about 1-2 weeks, depending on the antibody used, after which the pool is divided by limiting-dilution to generate single cell clones (0.7 to 1 cells/well) or mini-pools (5 to 50 cells/well). In case of landing pad cell line development, thousands of clones/mini-pools need to be screened to achieve clones with high expression of the reporter genes. Based on the expression of reporter genes (e.g. but not limited to SEAP, GLuc, Fluc, EGFP or a scFv antibody), the best producing clones (100-200 clones) were selected in the 96-well format and expanded to 24-wells and then to 6-wells plates. In 6-well, clonal cell lines were counted, normalized based on cell number, and then screened again to reduce the number of clones to be transferred to 125 ml shaker flasks. Research cell banks (RCBs) were generated for best producing landing pad cell lines and the small-scale fed-batch production of reporter genes was performed. Finally, top 4-6 cell lines were characterized by fluorescence in situ hybridization (FISH) to estimate the number of landing pad cassette integration site(s) in the genome of host cells. Monoclonal cell lines that contain only one integration site of the landing pad were considered as suitable cell lines for use for targeted integration of gene-of-interest cassette by recombination-mediated cassette exchange.

Designing of Landing Pad Vectors

To overcome the limitations of random integration, we have engineered landing-pad (LP) expression cassettes that can be integrated to the genome of mammalian cell lines, e.g. but not limited to CHO cells for developing parental cell lines, so called landing pad cell lines. For quantifiable, quick and cost-effective screening, the landing pad constructs encode for one or more detectable fluorescent proteins (e.g. EGFP among others) or secretable proteins (such as antibodies). Once integrated into the cells, landing pad cassette can be replaced with gene-of interest expression cassette by recombination-mediated cassette exchange (RMCE) to generate cell lines producing biologics.

Several versions of the landing pad expression cassettes containing the following elements were engineered:

1. Reporter genes for easy and cost-effective screening of high-producing clones. For protein production in industrial scale, a cell line should have high transcription and translation levels and for evaluation of these processes, both intracellular reporter genes (e.g. but not limited to Firefly luciferase, Fluc; EGFP, Green fluorescent protein) and extracellular reporter genes (e.g. but not limited *Gaussia* luciferase, Gluc; Secretative alkaline phosphatase, SEAP; monoclonal antibody) can be used. After the synthesis and post-translational modification, recombinant protein has to be secreted to the growth media, so that the purification of the protein would be easier. Therefore, besides transcription and translation, the ability to efficiently secrete large amount of protein(s) is crucial. Thus, secretative reporter genes such as SEAP (although other secretative reporter genes may also be used) describe the secretion machinery of the CHO clone.
2. Promoters for driving gene expression. Most promoters used in the landing pad cassettes are relatively weak viral or eukaryotic promoters, the purpose of which is to avoid downregulation of gene expression caused by high level of intracellular proteins. Relatively high levels of reporter gene expression driven by weak promoter usually means that the construct has integrated into transcriptionally active chromatin region.
3. Binding sites for chromatin anchoring proteins. Many different DNA-viruses replicate as extrachromosomal episomes. For efficient gene expression and replication, the episomal viral genomes situate near transcriptionally active regions of cell genome. The viral genomes are often transferred to these regions by viral protein(s) that bind to their respective binding-sites (BS). Therefore, by inserting virus BS-s into LP (landing pad) DNA, in the presence of viral proteins, the LP should be directed to transcriptionally active region of the chromatin prior to integration. For that, a binding region of BPV1 E2 protein and FR—binding region for Epstein Barr virus EBNA1 protein were inserted into the landing pad constructs. In addition, there is also included Polyomavirus replication origin (PY ori) that facilitates amplification of the integrated cassette in the presence of PY LT protein.
4. Recombination target sites (LoxP, FRT and attB) of site-specific recombinases are flanking the expression cassettes of reporter genes and selection marker. These sites are used for generation of cell lines for production of protein of interest. By inserting compatible recombinase target sites for site-specific recombinases to the gene-of-interest expression construct, it can be specifically inserted into genome of a parental cell line to the same position as landing pad. The targeted integration occurs between two LoxP sites facilitated by Cre recombinase, between FRT sites facilitated by Flp recombinase or between attB and attP sites facilitated by BxB1 recombinase.
5. Resistance gene for antibiotic, e.g., for Hygromycin B is required for selection of cells that contain integrated copy or copies of the landing pad cassette.

Plasmids. Detailed Description Vectors Used in Landing Pad Cell Line Development Landing pad vectors were constructed according to principles described above and the integrity of the elements was assessed by sequencing. Linearized constructs are schematically shown in FIG. 2. All plasmid DNA sequences (SEQ ID NO: 1, 2 and 3) are provided; therefore, the detailed molecular cloning steps are not presented here.

LP2str #132 (FIG. 2A, SEQ ID NO:1) contains two expression cassettes. Herpes simplex virus thymidine kinase promoter (pTK), followed by human elongation factor 1α intron A (NCBI Reference Sequence: NC_000006.12) is responsible for expressing the polypeptide, 887 amino acids in length. This polypeptide, encoded by SEQ ID NO:13, is marked as SEAP-2A-HygroR, consists of three parts:

```
i) Secreted alkaline phosphatase (SEAP)
from human placenta:
                              (SEQ ID NO: 16)
(MLLLLLLLGLRLQLSLGIIPVEEENPDFWNREAA

EALGAAKKLQPAQTAAKNLIIFLGDGMGVSTVTAA

RILKGQKKDKLGPEIPLAMDRFPYVALSKTYNVDK

HVPDSGATATAYLCGVKGNFQTIGLSAAARFNQCN

TTRGNEVISVMNRAKKAGKSVGVVTTTRVQHASPA

GTYAHTVNRNWYSDADVPASARQEGCQDIATQLIS

NMDIDVILGGGRKYMFRMGTPDPEYPDDYSQGGTR

LDGKNLVQEWLAKRQGARYVWNRTELMQASLDPSV

THLMGLFEPGDMKYEIHRDSTLDPSLMEMTEAALR

LLSRNPRGFFLFVEGGRIDHGHHESRAYRALTETI

MFDDAIERAGQLTSEEDTLSLVTADHSHVFSFGGY

PLRGSSIFGLAPGKARDRKAYTVLLYGNGPGYVLK
```

DGARPDVTESESGSPEYRQQSAVPLDEETHAGEDV

AVFARGPQAHLVHGVQEQTFIAHVMAFAACLEPYT

ACDLAPPAGTTDAAHPGYSRVGAAGRFEQT)
followed by ii) 2A peptide from foot-and-mouth disease virus
(SEQ ID NO: 17)
(APVKQTLNFDLLKLAGDVESNPGP)
followed by iii) hygromycin B phosphotransferase
(SEQ ID NO: 18)
(KKPELTATSVEKFLIEKFDSVSDLMQLSEGEESR

AFSFDVGGRGYVLRVNSCADGFYKDRYVYRHFASA

ALPIPEVLDIGEFSESLTYCISRRAQGVTLQDLPE

TELPAVLQPVAEAMDAIAAADLSQTSGFGPFGPQG

IGQYTTWRDFICAIADPHVYHWQTVMDDTVSASVA

QALDELMLWAEDCPEVRHLVHADFGSNNVLTDNGR

ITAVIDWSEAMFGDSQYEVANIFFWRPWLACMEQQ

TRYFERRHPELAGSPRLRAYMLRIGLDQLYQSLVD

GNFDDAAWAQGRCDAIVRSGAGTVGRTQIARRSAA

VWTDGCVEVLADSGNRRPSTRPDREMGEAN).

This polypeptide is processed co-translationally, yielding two final products—detectable SEAP and hygromycin B phosphotransferase that gives resistance to hygromycin B.

The second expression cassette contains the SV40 enhancer and early promoter (pSV40e), in-house developed synthetic intron, expression cassette of a second polypeptide, GLuc-2A-EGFP-2A-Fluc, and herpes simplex virus 1 thymidine kinase polyA signal. GLuc-2A-EGFP-2A-Fluc polypeptide, encoded by SEQ ID NO:12, consisting of 1024 amino acids has the following parts:

i) Gaussia luciferase
(SEQ ID NO: 19)
(MGVKVLFALICIAVAEAKPTENNEDFNIVAVASNF

ATTDLDADRGKLPGKKLPLEVLKEMEANARKAGCT

RGCLICLSHIKCTPKMKKFIPGRCHTYEGDKESAQ

GGIGEAIVDIPEIPGFKDLEPMEQFIAQVDLCVDC

TTGCLKGLANVQCSDLLKKWLPQRCATFASKIQGQ

VDKIKGAGGD)
followed by ii) 2A peptide from foot-and-mouth disease virus
(SEQ ID NO: 17)
(APVKQTLNFDLLKLAGDVESNPGP)
followed by iii) Enhanced green fluorescent protein
(SEQ ID NO: 20)
(SEQ ID NO: 15)
(FEMVSKGEELFTGVVPILVELDGDVNGHKFSVSGE

GEGDATYGKLTLKFICTTGKLPVPWPTLVTTLTYG

VQCFSRYPDHMKQHDFFKSAMPEGYVQERTIFFKD

DGNYKTRAEVKFEGDTLVNRIELKGIDFKEDGNIL

GHKLEYNYNSHNVYIMADKQKNGIKVNFKIRHNIE

DGSVQLADHYQQNTPIGDGPVLLPDNHYLSTQSAL

SKDPNEKRDHMVLLEFVTAAGITLGMDELYK)
followed by iv) 2A peptide from foot-and-mouth disease virus
(SEQ ID NO: 16)
(APVKQTLNFDLLKLAGDVESNPGP)
followed by v) Firefly luciferase
(SEQ ID NO: 21)
(MEDAKNIKKGPAPFYPLEDGTAGEQLHKAMKRYAL

VPGTIAFTDAHIEVDITYAEYFEMSVRLAEAMKRY

GLNTNHRIVVCSENSLQFFMPVLGALFIGVAVAPA

NDIYNERELLNSMGISQPTVVFVSKKGLQKILNVQ

KKLPIIQKIIIMDSKTDYQGFQSMYTFVTSHLPPG

FNEYDFVPESFDRDKTIALIMNSSGSTGLPKGVAL

PHRTACVRFSHARDPIFGNQIIPDTAILSVVPFHH

GFGMFTTLGYLICGFRVVLMYRFEEELFLRSLQDY

KIQSALLVPTLFGFFAKSTLIDKYDLSNLHEIASG

GAPLSKEVGEAVAKRFHLPGIRQGYGLTETTSAIL

ITPEGDDKPGAVGKVVPFFEAKVVDLDTGKTLGVN

QRGELCVRGPMIMSGYVNNPEATNALIDKDGWLHS

GDIAYWDEDEHFFIVDRLKSLIKYKGYQVAPAELE

SILLQHPNIFDAGVAGLPDDDAGELPAAVVVLEHG

KTMTEKEIVDYVASQVTTAKKLRGGVVFVDEVPKG

LTGKLDARKIREILIKAKKGGKIAV).

This polypeptide is also processed co-translationally, yielding three final products—*Gaussia* luciferase, EGFP and Firefly luciferase, all of which are reporter proteins that can be used for evaluating the productivity of the cell clones.

Between two expression cassettes are located:
i) The binding sites of BPV1 E2 protein (BPV E2BSs; SEQ ID NO: 22)
ii) polyomavirus core origin (PyVOri SEQ ID NO:23)
iii) The binding sites for EBNA-1 protein from Epstein-Barr virus known as Family of repeats (FR; SEQ ID NO:24)

LP2str #132 contains two types of recombinase target sites—LoxP and attB, recognized by Cre recombinase from bacteriophage P1 and BxB1 integrase from bacteriophage. When cells containing the LP2str #132 are used for generation of cell lines producing protein-of-interest, the exchange vectors should contain either two LoxP sites or two attP sites.

In LP2str_CAR_4F3 #182 and LP2str_4F3_wo BS #3, the expression cassette of Gluc-2A-EGFP-2A-Fluc is replaced with cassette encoding for an in-house developed antibody (4F3 scFv) that recognizes the Ebolavirus Zaire glycoprotein. The expression of this reporter gene is driven by Rous sarcoma virus long terminal repeat promoter (RSV LTR). A small intron (SEQ ID NO:25), located upstream of the ORF, and SV40 polyA signal are also included in the cassette.

LP2str_CAR_4F3 #182 contains incompatible or "heterospecific" recombinase target sites. At one side of the expression cassette, there is wild-type recognition site of Cre recombinase, known as LoxP site. A mutated target site, Lox2272 is flanking the expression cassettes from another side. Recombination occurs between two LoxP sites or between two Lox2272 sites, but not between the incompatible LoxP and Lox2272 sites. The introduction of different recombinase target sites to the plasmids helps to avoid the intramolecular recombination events. In addition, this landing pad cassette includes another set of incompatible recombinase target sites, FRT1 and FRT6 that are used by *Saccharomyces cerevisiae* site specific recombinase flippase (Flp). Recombination occurs between two FRT1 sites or between two FRT6 sites but not between the incompatible sites. For GOI-cell line development, the exchange vectors should also have two incompatible recombinase target sites, either Lox2272 and LoxP site, or FRT1 and FRT6 sites. At the same time, the Cre or Flp recombinase should be expressed.

pQMCF-7-BPVE2 #32 is the expression vector for BPV1 E2 protein. Expression cassette contains herpes simplex virus thymidine kinase promoter followed by human elongation factor 1α intron A, the coding region for BPV1 E2 protein and SV40 polyA sequence. SV40 enhancer and early promoter (pSV40e) drives expression of aminoglycoside phosphotransferase from Tn5 that gives resistance to aminoglycoside antibiotics, such as kanamycin and geneticin, used for selecting bacterial and mammalian cells, respectively. The purpose of using BPV1 E2 protein was to bind it to E2BS present in landing pad expression cassette in order to facilitate the loading of landing pad sequences to transcriptionally active chromatin region.

Designing of Gene-of-Interest Expression Vectors

Depending on the type of protein to be produced, vectors containing either one (e.g. SEQ ID NO:14) or two expression cassettes (SEQ ID NO:15) can be used. It is to be understood that other vectors may also be developed for this purpose. For driving the expression of gene of interest, human eIF4A1, human hEF1α, CAG promoter and RSV LTR are introduced to the cassettes. It is to be understand that other weak promoters may also be used. Also replacing these weak promoters with a stronger one, e.g. with CMV promoter or even with a transcriptionally active cellular promoter may be used.

Recombination vectors contain the expression cassette of another selection marker compared to landing pad cell lines, e.g. *Streptoalloteichus hindustanus* Sh ble gene, conferring resistance to zeocin or puromycin N-acetyltransferase, conferring resistance to puromycin. The expression of resistance gene is driven by SV40 early enhancer and promoter or HSV TK promoter and the bgh polyA signal is used in both cases.

For RMCE, recombinase target sites must be introduced to the recombination vectors. In order to use cell lines containing the LP2str #132 landing pad for protein-of-interest cell line development, recombination plasmids containing two wild-type LoxP sites or two attP sites should be used. For using cell lines having the LP2str_CAR_4F3 #182, recombination plasmids with incompatible Lox2272 and LoxP or recombination plasmids with incompatible FRT1 and FRT6 sites are use in RMCE to develop new cell lines.

Cell Culture and Transfections

CHO cells were cultivated in medium containing 1:1 mixture of CD CHO (Thermo Fisher Scientific, Cat No. 10743-029) and 293 SFMII (Thermo Fisher Scientific, Cat No. 11686-029). Medium is supplemented with 6 mM GlutaMax (Thermo Fisher Scientific, Cat No. 35050-038) and 10 ml/l HT Supplement (Thermo Fisher Scientific, Cat No. 41065-12). For selecting landing pad cell pools, medium is supplemented with 400 µg/ml Hygromycin B (Thermo Fisher Scientific, Cat No. 10687-010). For selecting cells expressing protein of interest, medium is supplemented with 100 µg/ml zeocin (Thermo Fisher Scientific, Cat. No. R250). Cells were grown at 37° C. in a humidified 8% $CO_2$ environment. For cultivating cells in 24-well, 6-well plates or 125 ml shaker flasks, orbital shaking incubator at 110 rpm (orbital diameter 25 mm) is used.

Cells were transfected by electroporation with Bio-Rad Gene Pulser II that was supplied with a capacitance extender (Bio-Rad Laboratories). For transfecting plasmid DNA or co-transfecting mRNA and plasmid DNA, capacitance and voltage settings were at 975 µF and 220 V. Cre (Cat. No. 30-101-113) and Flp mRNA (Cat. No. 130-106769) were obtained from Miltenyi Biotec.

Western Blot Analysis and Coomassie Blue Staining

Western blot analysis is performed to evaluate the expression of intracellular BPV1 E2 protein or the secreted human transferrin present in the cell culture media or fed-batch production media. For lysis, cells were collected by centrifugation, suspended in phosphate buffered saline, lysed in equal volume of Laemmli buffer containing DTT and heated at 100° C. for 5 minutes. The cases when DTT is not added, will be marked. Proteins were separated by SDS-polyacrylamide gel electrophoresis and transferred by a semidry blotting method to a polyvinylidene difluoride (PVDF) membrane (Millipore Corp.). For detecting BPV1 E2, membranes were incubated with in-house developed antibodies against E2 protein (1:1 mixture of #1E4 and #3E8, concentration 1 µg/ml). For detecting hTF, membranes were incubated with antibody against human transferrin (Abcam, Cat. No. 82411, concentration 1:8000). As secondary antibodies, goat anti-mouse IgG or goat anti-rabbit IgG, conjugated with HRP were. Detection was performed using TMB Solution III (Biopanda Diagnostics, Cat. No. TMB-P-001) following the manufacturer's recommendations.

SEAP and GLuc Measurement

For evaluating SEAP and GLuc expression, Secrete-Pair Dual Luminescence Assay Kit (GeneCopoeia, Cat. No. LF032) was used according to manufacturer's suggestions.

ELISA

To evaluate the expression of reporter gene 4F3 scFv by ELISA, in-house produced recombinant Zaire Ebolavirus glycoprotein (1 µg/ml) diluted in PBS was coated onto 96-well MaxiSorp NUNC-immunoplates and incubated overnight at 4° C. Plates were washed with 0.05% Tween20 (PBS-Tw) in PBS and blocked for 1 hour with 2% BSA in PBS-Tw. Dilutions from the cell culture media was prepared and incubated for one hour at room temperature on the shaker. Typically, growth media collected from the 96-well plate is diluted 1:2 to 1:10 and growth media collected from 6-well plate is diluted 1:1000. Horseradish peroxidase (HRP)-conjugated goat anti-human IgG (LabAS), diluted in 1% BSA in PBS-Tw, was used as a secondary antibody for 45 min. After washing, the reaction was developed with the TMB solution VIII (2 in 1) (Biopanda Diagnostics, Cat. No. TMB-P-003) for 10 min and stopped with 0.5 M $H_2SO_4$. The absorbance at 450 nm was measured spectrophotometrically using the ELISA plate reader. For evaluating the concentration of 4F3 scFv in growth media, 2-fold serial dilutions of in-house purified 4F3 scFv antibody were added as standards.

For evaluating the expression level of hTF and calculating the productivity of hTF cell lines, the Elisa kit from Abcam (Cat. No. ab187391) was used according to manufacturer's protocol.

Fed-Batch Production

For fed-batch production analysis, cells were seeded at $4 \times 10^6$ cells/ml in 25-30 ml (in 125 shaker flasks) and the incubation temperature was shifted from 37° C. to 30° C. Cells were fed on days 0, 2, 4, 6 and 8 with 6% of proprietary feed and the production media was collected at day 10. For production of recombinant proteins, Feed B (Thermo Fisher Scientific, Cat. No. A1024001) supplemented with 6 mM GlutaMax (Thermo Fisher Scientific, Cat No. 35050-038) was used. For production of antibodies, the 1:1 mixture of Feed A (Thermo Fisher Scientific, Cat. No. A1023401) and Feed B (Thermo Fisher Scientific, Cat. No. A1024001), supplemented with 6 mM GlutaMax (Thermo Fisher Scientific, Cat No. 35050-038) was used.

Example 1. BPV1 E2 Protein Increases the Expression Level of Recombinant Proteins in Mammalian Cells To test whether BPV1 E2 protein affects the recombinant protein expression in mammalian cells and could be used in stable cell line development, the landing pad vectors with (SEQ ID NO:2) and without BPV1 E2 binding sites (SEQ ID NO:3) were generated. Expect in the presence or absence of E2 binding sites, both vectors are similar and contain the expression cassettes of two reporter genes—one for in-house developed single chain antibody (4F3 scFv, encoded by SEQ ID NO: 11) and the other for secreted alkaline phosphatase (SEAP). SEAP-2A-Hygromycin is transcribed as a single transcript and cleaved during translation by 2A peptide to SEAP and hygromycin phosphotransferase that gives resistance to hygromycin B. Compared to SEAP-2A-Hygromycin, 4F3 scFv was expressed from opposite strand.

Before transfection, LP2str_4F3_CAR #182 (SEQ ID NO:2) and LP2str_4F3_wo BS #3 (SEQ ID NO:3) were linearized with VspI restrictase to excise unnecessary bacterial origin of replication and prokaryotic selection marker region. The gel-purified linearized landing pad cassettes and the circular expression vector of bovine papillomavirus E2 protein (SEQ ID NO:4) were co-transfected to CHO-S clone #QE3 cells by electroporation.

In each transfection, 150 ng of landing pad vector (either SEQ ID NO:8 or SEQ ID NO:9) was used, whereas the amount of transfected BPV1 E2 vector was changed in the experiment. The scheme of the transfection is the following:
1) mock
2) 150 ng LP2str_4F3_CAR #182/VspI
3) 150 ng LP2str_4F3_CAR #182/VspI+5 ng pQMCF-7-BPV1E2 #32
4) 150 ng LP2str_4F3_CAR #182/VspI+50 ng pQMCF-7-BPV1E2 #32
5) 150 ng LP2str_4F3_CAR #182/VspI+250 ng pQMCF-7-BPV1E2 #32
6) 150 ng LP2str_4F3 w/o BS #3/VspI+5 ng pQMCF-7-BPV1E2 #32
7) 150 ng LP2str_4F3 w/o BS #3/VspI+50 ng pQMCF-7-BPV1E2 #32
8) 150 ng LP2str_4F3 w/o BS #3/VspI+250 ng pQMCF-7-BPV1E2 #32

Two days after transfection, the 400 µg/ml Hygromycin B was added to the media and the cells were selected in the presence of antibiotic for one week to generate stable cell pools containing integrated landing pad cassettes. The probe number 1 (mock) did not survive the selection as it was not transfected with landing pad cassette and therefore, it does not contain the hygromycin phosphotransferase gene. 7 days after the addition of hygromycin B, the cells of selected pools were counted, seeded with equal density and the probes for analyzing the expression of reporter genes were collected 2 days after the normalization. The expression of 4F3 scFv was tested by enzyme-linked immunosorbent assay (ELISA) and the expression of SEAP was measured by Secrete-Pair Dual Luminescence Assay Kit (GeneCopoeia) according to manufacturer's recommendations. FIG. 3 summarizes the results of both assays. Results are presented as relatives to probe 2, transfected only with the landing pad expression cassette.

As seen in FIG. 3, the presence of E2 binding sites in the landing pad vector positively affects the expression of 4F3 scFv and SEAP reporter genes. Furthermore, when E2 binding sites are present, the expression of both reporter genes increases together with the amount of transfected BPV1 E2 construct. The expression level of SEAP and 4F3 scFv from LP2str_4F3_CAR #182 is similar to the control (probe 2) if only 5 ng of pQMCF-7-BPV1 E2 was transfected. However, the expression of 4F3 scFv is ~3.5 fold and the expression of SEAP is ~2.5 fold higher than control when 250 ng of pQMCF-7-BPV1 E2 was transfected. When E2 binding sites are not present in the landing pad cassette, the concentration of the reporter proteins in the media is not dependent on the amount of transfected BPV1 E2 vector.

Taken together, the expression of BPV1 E2 protein increases the reporter gene expression when E2 binding sites are introduced to the landing pad vectors. Thus, BPV 1 E2 protein could be used in stable mammalian cell line development to increase the expression of recombinant protein, such as antibodies or other secreted proteins.

Example 2. The Generation of #504C6 Landing Pad Cell Line

FIG. 4A provides an example of landing pad cell line generation. The selected pool, originating from transfection number 5 (FIG. 3, marked with star) had the highest expression of both reporter genes and therefore, it was chosen for sub-cloning to mini-pools. Cloning to mini-pools rather than single-cell clones was preferred as this approach helps to increase the number of clonal cell lines to be analysed.

For mini-pool cloning, the cell pool was counted, diluted to density of 250 cells/ml and seeded to 90 96-well plates (100 µl per well). 5 days later, the ELISA screen for testing the expression of 4F3 scFv antibody was performed, after which the top 20 mini-pools were divided again ($2^{nd}$ round mini-pool cloning). This time, each well, containing ~400-800 cells was divided between two 96-well plates and cultivated for 2 weeks, after which the screening to test the expression of 4F3 scFv was performed to select top 8 mini-pools (#51, 62, 66, 67, 60, 31, 50 and 15). These highest producers were cultivated to larger volume and divided by limiting dilution (0.5 cells/well) to achieve clonal cell lines. After the clones achieved desired cell density, the expression analysis of 4F3 scFv was performed to select top 120 cell lines that were expanded to 6-well plates.

In 6-well plates, cells were counted and diluted to similar density ($5 \times 10^5$ cells/ml). After 3 days, the samples from growth media were collected for evaluating 4F3 scFv expression by ELISA. In 6-well, 120 clonal cell lines were analysed and based on the ELISA results, the top 10% of cell lines (FIG. 4B) were transferred to 125 ml shaker flasks and cultivated to desired volume and density for research cell bank generation. The calculated concentration of 4F3 scFv in culture media of selected 12 cell lines ranged from ~30-60 mg/l in growth conditions. Next, top 12 cell lines were transferred to 30° C. to test the productivity of reporter antibody in small-scale fed-batch production. Throughout production, 6% of the mixture of Feed A and B was added to the cells on days 0, 2, 4, 6 and 8. At day 10, the production media was collected, clarified by centrifugation (1000×g, 30 min, 4° C.) after which the concentration of secreted 4F3 was analysed by Octet K2 (FIG. 4C). The results of Octet K2 show that the productivities of the cell lines ranged from −800 to 1500 mg/l in all cell lines. All clones from mini-pool #62 produced more than 1200 mg/l of 4F3 scFv, whereas the clones from mini-pools #50 and #67 produced 850 mg/l and 800 mg/ of 4F3 scFv, respectively.

Thus, by co-transfecting CHO cells with the landing pad vector (SEQ ID NO:2) and BPV1 E2 expression cassette (SEQ ID NO:4), it is possible to generate the parental cell lines with high expression of reporter antibody.

Example 3. #504C6 Landing Pad Cell Line has One Integration Site in the CHO Genome Great parental cell lines have integrated the landing pad expression cassette into the active site of the genome. Random integration approach, used in the landing pad cell line development, could generate cell lines with either single or several integration sites of the cassette. Therefore, when only one integration site of the transgene is acceptable for the parental cell line, more than one clonal cell line should be developed to the RCB stage.

To investigate the monoclonality of the cell lines as well as the number of integration sites of LP2str_4F3_CAR #182 (SEQ ID NO:2) in the CHO cell genome by fluorescence in situ hybridization (FISH), metaphase chromosomes from three cell lines (#621 A2, #622 A11 and #504 C6) were prepared and hybridized with biotin labeled LP2str_4F3_CAR #182. Signal was amplified with Tyramide signal amplification kit and detected with HRP-Streptavidin and Alexa Fluor™ 488 Tyramide. According to the results, all three cell lines were monoclonal, meaning that all metaphase cells have a similar integration pattern. Two of the cell lines (#621 A2 and #622 A11), originating from the mini-pool #62, had two integration sites of the landing pad cassette and will therefore not used in the later stages of the development. The cell line #504 C6, originating from mini-pool #50, was selected for further studies because this cell line has a single integration site of the LP2str_4F3_CAR #182, located at telomeric region of a large chromosome. The results of FISH analysis of #504 C6 cell line are presented on FIG. 5.

Targeted locus amplification (TLA) analysis (outsourced from Cergentis B.V.) confirmed the FISH analysis, showing that there is only one integration site of the LP2str_4F3_CAR #182 located in the scaffold 15 (data not shown).

Example 4. The Expression of 4F3 scFv Antibody is Stable for at Least 8 Weeks in #504 C6 Landing Pad Cell Line A long generation time of mammalian cells is needed to achieve the desired growth volume and cell density in bioreactors before the production of biologics could be started. Therefore, one important requirement for the production cell line is the stability of recombinant protein expression for at least one month. For testing the stability of the reporter gene expression in our landing pad cell line #504 C6, it was cultivated for 8 weeks. Throughout the experiment, cells were monitored and diluted every 2-3 days. Each week, cells were diluted to the same density ($5\times10^5$ cells/ml in 20 ml) and after 2 days, the sample of the growth media was collected. After 8 weeks, ELISA analysis was performed to compare the amount of 4F3 scFv antibody in growth media. The results, presented in FIG. 6, demonstrate that #504 C6 cell line maintains the stable expression of 4F3 scFv for at least 8 weeks. There are small reductions in the expression level of 4F3 scFv on weeks 2 and 5, probably caused by the difference in the counting of cells.

Example 5. BPV1 E2 Expression Vector has Integrated to the Genome of the Landing Pad Cells Enabling the Constant Expression of BPV1 E2 Protein For generation of landing pad cell line #504 C6, the unmodified CHO-S cell line was co-transfected with LP2str_4F3_CAR #182 and pQMCF-7-BPV1E2 #32. The landing pad vector has the expression cassette for hygromycin phosphotransferase, favoring the integration of the cassette in the presence of hygromycin B selection. pQMCF-7-BPV1E2 #32 contains the expression cassette for aminoglycoside phosphotransferase that makes cells resistant to neomycin and geneticin, however, these antibiotics were not used to select the integration of BPV1 E2 expression cassette. To find out whether the fragments of pQMCF-7-BPV1E2 #32 could also have integrated to the #504 C6 cell line, the TLA analysis of this vector was done together with LP2str_4F3_CAR #182 analysis. To our surprise, #504 C6 cell line contained the whole pQMCF-7-BPV1E2 #32.

Although pQMCF-7-BPV1E2 #32 was integrated to the #504 C6 landing pad cells it does not necessarily mean that the BPV1 E2 protein itself is expressed at the detectable level. Therefore, western blot analysis for evaluating BPV1 E2 expression was performed in 12 parental cell lines, characterized in FIG. 4C. A control cell line #21F5, generated by random integration of only LP2str_4F3_CAR #182 but without pQMCF7-BPV1E2 #32 was also included in the experiment as a negative control. As seen on the western blot, presented in FIG. 7A, all landing pad cell lines, except the negative control #21F5 express BPV1 E2.

Figure 7B:
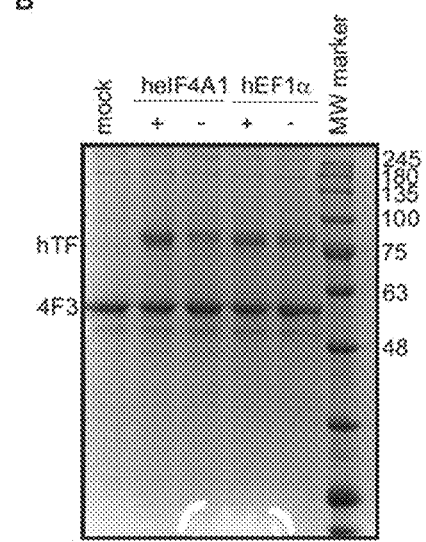

Example 6. BPV1 E2 Protein Upregulates the Transient Expression of Recombinant Proteins Via E2 Binding Sites Introduced to the Plasmids BPV1 E2 protein is a transcription factor that regulates the transcription via its binding sites in the viral genome. To study whether the BPV1 E2 protein, encoded from the integrated expression cassette in CHO cells, could help to increase the expression level of an ectopically expressed recombinant protein via E2 binding sites introduced to the plasmid DNA, a transient expression experiment was performed in #504 C6 landing pad cell lines. For this, 4 different constructs expressing a recombinant protein such as human transferrin were prepared. In two of the plasmids, hTF transcription is driven by the heIF4A1 promoter and in another two plasmids by hEF1α promoter. In both cases, one of the cassette contained the E2 binding sites upstream of the promoter (marked with +), whereas another construct lacks E2 binding sites (marked with −). For evaluating the effect of the E2BSs on the hTF protein expression, the plasmid DNAs and a mock control (only carrier DNA) were transfected by electroporation to #504 C6 cells. 3 days later, supernatant samples were collected and the expression of hTF was analysed by western blot. As seen in FIG. 7B, two proteins have been visualized. The immunoblot analysis demonstrates that the expression of hTF (upper band) is highest from plasmids containing the E2 binding sites. In case of both promoters (heIF4A1 and hEF1), the expression of hTF was lower in the absence of BPV1 E2 binding sites. The reporter antibody 4F3 scFv (lower band), detectable due to the cross-reactivity of the secondary antibody towards scFv, is expressed at similar level in all pools.

Taken together, the presence of BPV1 E2 binding sites in the proximity of promoters driving the transcription of a recombinant protein (such as human transferrin) has a positive effect on the expression level of these proteins in BPV1 E2 positive cell line such as #504 C6.

Example 7. Optimization of the Conditions for Recombination-Mediated Cassette Exchange Required for the Efficient Development of Cell Lines Producing Protein of Interest The IcoCell parental cell lines such as #504 C6 contain the integrated landing pad cassette in the active site of the genome which facilitates the high expression of the reporter genes. In addition, the recognition sites of several site-specific recombinases were introduced to ends of the landing pad cassette so that these sites could facilitate the recombination mediated cassette exchange to replace the landing pad construct with the expression cassettes of monoclonal antibodies or other recombinant proteins. Since #504 C6 landing pad cell line maintains the stable expression of 4F3 scFv for at least 8 weeks (FIG. 6), the cell lines generated via targeted integration through RMCE should have the similar stability properties. The productivity of 4F3 scFv antibody in fed-batch conditions was ~850 mg/l (FIG. 4C) and it is expected that the cell lines generated from #504 C6 by targeted integration produce the recombinant proteins in a similar manner.

504 C6 landing pad cell line consists the LP2str_4F3_CAR #182 (SEQ ID NO:2) which contains the recognition sequences for different site-specific recombinases (Cre, Flp and BxB1). The site-specific recombinase of bacteriophage P1, the Cre protein, recognizes 34 bp DNA sequence known as LoxP site (SEQ ID NO:5), mutated sites such as Lox2272 (SEQ ID:NO6) and others. Compared to LoxP site, Lox2272 contains two mutated residues in the 8 bp spacer sequence and preferably, site-specific recombination occurs either between LoxP or Lox2272 sites. In respect to each other, the "heterospecific" LoxP and Lox2272 sites are "incompatible", meaning that the recombination between these two sites does not take place or occurs at a very low frequency.

LoxP and Lox2272 sites are also included in exchange vectors (SEQ ID NO:7 and SEQ ID NO:8) and for targeted integration, the landing pad cells (e.g., to #504 C6 cells) should be co-transfected with exchange vectors and with either the plasmid DNA or mRNA encoding the Cre recombinase. In respect to recombination efficiency, each genomic locus is different and therefore, optimization of transfection e.g., the amount of plasmid DNA and Cre mRNA is crucial for each parental cell line.

To optimize the recombination process in #504 C6 parental cell line and find suitable conditions for protein of interest cell line development, these cells were co-transfected with pREC-Lox2272-E2BS-heIF4A1-hTF-SV40eP-Zeo #11 plasmid and Cre recombinase mRNA (Miltenyi Biotec GmbH). Scheme of the optimization experiment is presented in FIG. 8A.

Figures 8A, 8B:
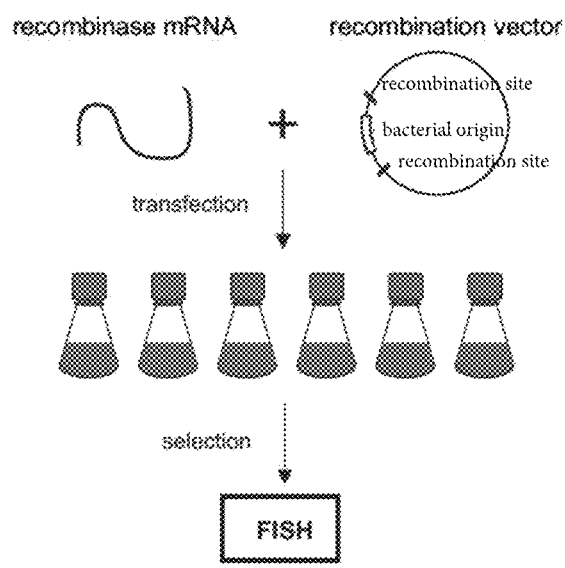

As seen in FIG. 8A, either 1 or 3 µg of Cre mRNA and 100 ng, 300 ng or 1000 ng of the exchange vector was used in each transfection. For increasing transfection efficiency 50 µg of in-house purified carrier DNA from CHO cells was added to each transfection. Mock control, transfected with carrier DNA was included to the experiment to assess the length of zeocin selection. For each transfection, $6 \times 10^6$ cells (in 250 µl of the growth media) were mixed with appropriate amount of carrier, plasmid DNA and Cre mRNA in 4-mm electroporation cuvette and transfected by electroporation using BioRad Gene Pulser II, supplied with a capacitance extender (Bio-Rad Laboratories) (settings 230 V; 975 µF). After transfection, cells were collected by centrifugation (300×g 5 min), diluted to required cell density ($10^6$ cells/ml) and cultivated for 48 hours, after which fresh media was added to the cells. 72 hours after transfection, 100 µg/ml zeocin was added to select the cells containing the exchange vector. After 2 weeks, selection was over and the efficiencies of targeted and random integration of selected pools were assessed by FISH analysis.

For FISH, the plasmid DNA containing unique elements of pREC-Lox2272-E2BS-heIF4A1-hTF-SV40eP-Zeo #11 was constructed, labeled with biotin and used for hybridization of metaphase chromosomes of cell pools selected with zeocin. Signal was amplified with Tyramide signal amplification kit and detected with HRP-Streptavidin and Alexa Fluor™ 488 Tyramide, At least 100 metaphase cells were examined for each pool to calculate the frequencies of targeted integration, targeted integration with additional random integration of the recombination cassette, or random integration events with up to 2 or more integration sites. The results of FISH, summarized in FIG. 8B, demonstrate that the recombination efficiency is the best (42%) in cell pool no 5 which was transfected with 3 µg of Cre mRNA and 300 µg of recombination plasmid. 19% of the cells from pool no 5 contain the exchange vector in 2 integration sites, one of which is targeted and another in the random site of the genome. In 39% of the cells, the targeted integration has not occurred, and the recombination plasmid has integrated to the random site of the genome. The frequency of random integration is high (~60% or more) in cell pools no. 1-3 (transfected with 1 µg of Cre mRNA) and no. 4 (transfected with 3 µg of Cre mRNA and 100 ng exchange vector). Compared to cell pool no. 5, pool no. 6 (3 µg of Cre mRNA and 1000 ng exchange vector) has slightly higher frequency (45%) for random integration and lower (31%) for targeted integration with one integration site. Therefore, the pool no. 5 will be sub-cloned by limiting dilution.

Similar experiment was also performed with Flp recombinase and the exchange vectors containing incompatible recombination target sequences of this enzyme, namely FRT1 and FRT6 sites. It has been shown by several authors that RMCE using FRT sites is efficient and precise and could be used for development of cell lines encoding for protein of interest (Kim and Lee, 2008; Zhang et al., 2015). However, in our system, the frequency of site-specific integration using the Lox2272 and LoxP sites is higher compared to the use of FRT1 and FRT6 sites. In our system, Cre recombinase and exchange plasmids containing its incompatible recombination target sites Lox2272 and LoxP are preferred according to the results of this investigation.

Transfection with 3 µg Cre mRNA and 300 µg recombination plasmid yielded the cell pool with highest frequency of RMCE and lowest frequency of random integration and thus, these conditions will be used for following cell line developments with the #504 C6 parental cell line.

Example 8. Generation of a Cell Line Expressing Recombinant Protein

Figures 10A, 10B:
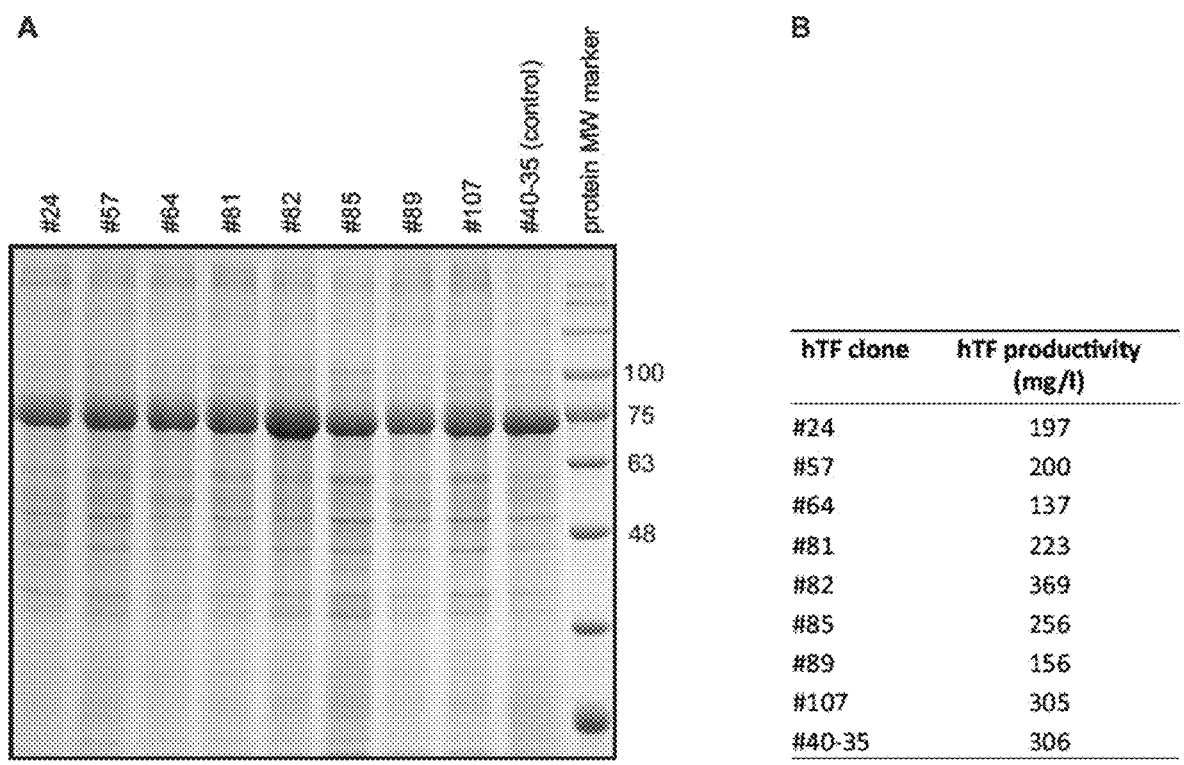

For generation of clonal cell line expressing human transferrin, the cell pool that had the highest frequency of targeted integration was sub-cloned by limiting dilution. After 3-4 weeks, screening of the loss of 4F3 scFv was performed in 96-well format to select cells with targeted integration of the exchange vector and to eliminate clones with random integration of the cassette. The cell lines without 4F3 scFv were expanded to 24-well and to 6-well and normalized to similar density. hTF expression was analyzed using the commercial ELISA kit (Abcam, Cat. No. ab187391) according to manufacturer's recommendation. Cell lines #24, #57, #64, #82, #85, #89 and #107, expressing hTF at highest level, were transferred to 125 ml shaker flasks, cultivated to desired cell density for research cell bank generation. After that, the productivities of cell lines were tested in small-scale fed-batch culture, similarly to 4F3 production described in example 2, except Feed B (not the mixture of Feed A and B) was added every 2 days. Production supernatants were analyzed by SDS-Page followed by Coomassie blue staining (FIG. 10A) and the amount of hTF in the media/productivities of hTF cell lines were quantified with hTF ELISA kit (FIG. 10B).

The Coomassie blue staining of hTF production supernatants (FIG. 10A) demonstrate the proteins are intact and the migration properties of the produced protein are as expected (~75 kDa). The presence of other cellular proteins in the production media is minimal. According to the SDS-Page analysis, clone #82 produces hTF protein at highest level, followed by a control #40-35 from another development. hTF quantification by Elisa (FIG. 10B) confirm that clone #82 with productivity of 369 mg/l is the best cell line, followed by clone #107 and control #40-35 both producing human transferrin with productivity of ~300 mg/l. Thus, the use of RMCE using the #504 C6 parental cell line permits to develop protein of interest cell lines with good productivity.

Example 9. Protein of Interest Cell Lines Developed from #504 C6 Parental Cell Line by RMCE Express BPV1 E2 Protein The parental cell line #504 C6 is BPV1 E2 positive, meaning that it expresses E2 protein at detectable level. Although, BPV1 E2 expression cassette is integrated to the #504 C6 landing pad cell line, it is unknown whether E2 protein is also expressed in protein of interest cell lines that have undergone RMCE, antibiotic selection and the long cultivation time from single cell to RCB. Western blot analysis was performed to test the BPV1 E2 protein expression in hTF cell lines. For this, cells in fed-batch production were counted, lysed and the lysate of ~50 000 cells was analyzed. The immunoblot in FIG. 11 show that BPV1 E2 protein expression is stable as the protein is detectable in all hTF cell lines.

Thus, BPV1 E2 protein expression is stable in protein of interest producing cell lines generated from #504 C6. It is possible, that the transactivation properties of E2 that lead to upregulation of gene expression from promoters close to E2BSs could also occur in stable cell lines generated by RMCE.

REFERENCES

Bebbington, C. R., Renner, G., Thomson, S., King, D., Abrams, D., and Yarranton, G. T. (1992). High-level expression of a recombinant antibody from myeloma cells using a glutamine synthetase gene as an amplifiable selectable marker. Biotechnol. Nat. Publ. Co. 10, 169-175.

Frye, C., Deshpande, R., Estes, S., Francissen, K., Joly, J., Lubiniecki, A., Munro, T., Russell, R., Wang, T., and Anderson, K. (2016). Industry view on the relative importance of "clonality" of biopharmaceutical-producing cell lines. Biol. J. Int. Assoc. Biol. Stand. 44, 117-122.

Inniss, M. C., Bandara, K., Jusiak, B., Lu, T. K., Weiss, R., Wroblewska, L., and Zhang, L. (2017). A novel Bxb1 integrase RMCE system for high fidelity site-specific integration of mAb expression cassette in CHO Cells. Biotechnol. Bioeng. 114, 1837-1846.

Kaufman, R. J., and Sharp, P. A. (1982). Amplification and expression of sequences cotransfected with a modular dihydrofolate reductase complementary dna gene. J. Mol. Biol. 159, 601-621.

Kim, M. S., and Lee, G. M. (2008). Use of Flp-mediated cassette exchange in the development of a CHO cell line stably producing erythropoietin. J. Microbiol. Biotechnol. 18, 1342-1351.

Liu, P.-Q., Chan, E. M., Cost, G. J., Zhang, L., Wang, J., Miller, J. C., Guschin, D. Y., Reik, A., Holmes, M. C., Mott, J. E., et al. (2010). Generation of a triple-gene knockout mammalian cell line using engineered zinc-finger nucleases. Biotechnol. Bioeng. 106, 97-105.

Urlaub, G., and Chasin, L. A. (1980). Isolation of Chinese hamster cell mutants deficient in dihydrofolate reductase activity. Proc. Natl. Acad. Sci. U.S.A 77, 4216-4220.

Wigler, M., Perucho, M., Kurtz, D., Dana, S., Pellicer, A., Axel, R., and Silverstein, S. (1980). Transformation of mammalian cells with an amplifiable dominant-acting gene. Proc. Natl. Acad. Sci. U.S.A 77, 3567-3570.

Zhang, L., Inniss, M. C., Han, S., Moffat, M., Jones, H., Zhang, B., Cox, W. L., Rance, J. R., and Young, R. J. (2015). Recombinase-mediated cassette exchange (RMCE) for monoclonal antibody expression in the commercially relevant CHOK1SV cell line. Biotechnol. Prog. 31, 1645-1656.

Zhu, J. (2012). Mammalian cell protein expression for biopharmaceutical production. Biotechnol. Adv. 30, 1158-1170.

What is claimed is:

1. A method to develop parental cell lines stably expressing BPV1 E2 protein, said method comprising the steps of:
   a) providing a landing pad construct comprising recognition sites of site-specific recombinases at 5' and 3' ends of the landing pad construct, and at least one reporter gene encoding a detectable reporter protein, at least one nucleotide sequence encoding a selection marker, and binding sites of a bovine papillomavirus (BPV) E2 protein;
   b) providing an expression vector comprising a nucleotide sequence encoding a BPV E2 protein;
   c) co-transfecting a mammalian cell with the landing pad construct and the expression vector, wherein the expression vector integrates into the genome of the transfected mammalian cell;
   d) allowing tethering of the landing pad construct to a transcriptionally active chromatin locus by allowing expression of E2 protein from the expression vector integrated into the genome of the transfected mammalian cell; and
   e) screening expression levels of the at least one reporter gene in cell pools obtained from step d) and selecting cells that have highest expression levels as the parental cell lines stably expressing BPV1 E2 protein.

2. The method of claim 1, wherein the mammalian cell is a Chinese Hamster Ovary (CHO) cell.

3. A method for high and stable expression of a gene of interest, said method comprising the steps of:
   a) developing a parental cell line stably expressing BPV1 E2 protein according to the method of claim 1;
   b) providing a gene of interest construct comprising the same recognition sites of the site-specific recombinases as the landing pad construct;
   c) replacing the landing pad construct with the gene of interest construct by co-transfecting the parental cell line with the gene of interest construct and an expression construct or mRNA for site-specific recombinases recognized by the recognition sites; and
   d) cultivating the co-transfected cell line in an environment suitable for expression of the gene of interest.

4. The method of claim 3, wherein the cell line is a Chinese Hamster Ovary (CHO) cell.

5. The method of claim 3, wherein the gene of interest encodes a recombinant protein.

6. The method of claim 5, wherein the recombinant protein is an antibody.

7. The method of claim 1, wherein the recognition sites of site-specific recombinases are wild-type recombination sites of Cre recombinase according to SEQ ID NO: 5.

8. The method of claim 1, wherein the recognition sites of site-specific recombinases are incompatible Cre recombinase sites.

9. The method of claim 1, wherein the landing pad construct comprises a polynucleotide comprising sequences encoding multiple detectable reporter proteins expressed as one polypeptide and wherein each detectable reporter protein is capable of being detected separately.

10. The method of claim 9, wherein the polynucleotide comprises the nucleotide sequence of SEQ ID NO: 12, and the multiple detectable reporter proteins are *Gaussia* luciferase protein, EGFP and firefly luciferase.

11. The method of claim 1, wherein the detectable reporter protein is secreted protein alkaline phosphatase.

12. The method of claim 1, wherein the at least one nucleotide sequence encoding the selection marker and the at least one reporter gene are linked with a nucleotide sequence encoding a Foot and Mouth Disease Virus (FMDV) 2A peptide.

13. The method of claim 1, wherein the landing pad construct comprises the nucleotide sequence of SEQ ID NO: 1 or 2.

* * * * *

SEQUENCE LISTING

```
Sequence total quantity: 26
SEQ ID NO: 1           moltype = DNA   length = 13279
FEATURE                Location/Qualifiers
source                 1..13279
                       mol_type = other DNA
                       organism = synthetic construct
```

SEQUENCE: 1

```
ctaggcttttt gcaaaaagct taagcgtacg gtaagtggcg tttctcgggg agccagctgc    60
gtccgctgtc gtgctgtcgg tgtagtacta gcaagcgtta agtccccatc tggctgcggc   120
ctaccgaaga gtggtcttca cgtcacacgc tgtcccacgc agtggttggt ttggtcgctt   180
ctggttactg actactaagc agcctttcct tttttccttt cagccaccat gggcgtgaag   240
gtgctgttcg ccctgatctg tatcgccgtg gccgaggcca agccaccga gaacaatgag   300
gacttcaaca tcgtggccgt ggccagcaac ttcgccacca cagacctgga tgccgacaga   360
ggcaagctgc ccggcaagaa actgcccctg gaagtgctga agagatgga agccaatgcc   420
agaaaggccg gctgcaccag aggctgcctg atctgcctga gccacatcaa gtgcaccccc   480
aagatgaaga agttcatccc cggcagatgc cacacctatg agggcgacaa agagtctgcc   540
cagggcggca tcggcgaggc catcgtggac atccccgaga tccccggctt caaggacctg   600
gaacccatgg aacagtttat cgcccagtg gacctgtgcg tggactgcac caccggctgt   660
ctgaagggcc tggccaacgt gcagtgcagc gacctgctga gaagtggct gccccagaga   720
tgcgccacct tcgccagcaa gatccagggc caggtgaca caggtcaaggg ggctggcggc   780
gacgcaccgg tgaaacagac tttgaatttt gaccttctca agttggcggg agacgtggag   840
tccaaccctg ggccttcga aatggtgagc aagggcgagg agctgttcac cggggtggtg   900
cccatcctgt tcgagctgga cggcgacgta aacggccaca gttcagcgt gtccggcgag   960
ggcgagggcg atgccaccta cggcaagctg accctgaagt tcatctgcac caccggcgag  1020
ctgcccgtgc cctggcccac cctcgtgacc accctgacct acggcgtgca gtgcttcagc  1080
cgctacccg accacatgaa gcagcacgac ttcttcaagt ccgccatgcc cgaaggctac  1140
gtccaggagc gcaccatctt cttcaaggac gacggcaact acaagaccg cgccgaggtg  1200
aagttcgagg gcgacaccct ggtgaaccgc atcgagctga agggcatcga cttcaaggag  1260
gacggcaaca tcctggggca caagctggag tacaactaca acagccacaa cgtctatatc  1320
atggccgaca gcagaagaa cggcatcaag gtgaacttca agatccgcca caacatcgag  1380
gacggcagcg tgcagctcgc cgaccactac cagcagaaca cccccatcgg cgacggcccc  1440
gtgctgctgc ccgacaacca ctacctgagc acccagtccg ccctgagcaa agaccccaac  1500
gagaagcgcg atcacatggt cctgctggag ttcgtgaccg ccgccgggat cactctcggc  1560
atggacgagc tgtacaaggc accggtgaaa cagactttga attttgacct tctcaagttg  1620
gcgggagacg tggagtccaa ccctgggccc atggaagatg ccaaaaacat taagaaaggc  1680
ccagcgccat tctacccact cgaagacggg accgccgagc agcagctgca caagcatg   1740
aagcgctacg ccctggtgcc cggcaccatc gcctttaccg acgcacatat cgaggtggac  1800
attacctacg ccgagtactt cgagatgagc gttcggctgg cagaagctat gaagcgctat  1860
gggctgaata caaaccatcg gatcgtggtg tgcagcgaga atagcttgca gttcttcatg  1920
cccgtgttgg gcgcctgtt catcggtgtg gctgtggcca cagctaacga catctacaac  1980
gagcgcgagc tgctgaacag catgggcatc agccagccca cgtcgtatt cgtgagcaag  2040
aaagggctgc aaaagatcct caacgtgcaa aagaagctac cgatcataca aaagatcatc  2100
atcatggata gcaagaccga ctaccaggc ttccaaagca tgtacacctt cgtgacttcc  2160
catttgccac ccggcttcaa cgagtacgac ttcgtgcccg agagcttcga ccgggacaaa  2220
accatcgccc tgatcatgaa cagtagtggc agtaccggat tgcccaaggg cgtagcccta  2280
ccgcaccgca ccgcttgtgt ccgattcagt catgcccgcg accccatctt cggcaaccag  2340
atcatccccg acaccgctat cctcagcgtg gtgccatttc accacggctt cggcatgttc  2400
accacgctgg gctacttgat ctgcggcttt cgggtcgtgc tcatgtaccg cttcgaggag  2460
gagctattct tgcgcagctt gcaagactat aagattcaat ctgccctgct ggtgcccaca  2520
ctatttggct tcttcgctaa gagcactctc atcgacaagt acgacctaag caacttgcac  2580
gagatcgcca gcggcgggc gccgctcagc aaggaggtag gtgaggccgt ggccaaacgc  2640
ttccacctac caggcatccg ccagggctac ggcctgacga aaacaaccag cgccattctg  2700
atcaccccg aagggacga caagcctggc gcagtaggca aggtggtgcc cttcttcgag  2760
gctaaggtgg tggacttgga caccggtaag acactgggtg tgaaccagcg cggcgagctg  2820
tgcgtccgtg gccccatgat catgagcggc tacgttaaca accccgaggc tacaaacgct  2880
ctcatcgaca aggacggctg gctgcacagc ggcgacatcg cctactggga cgaggacgag  2940
cacttcttca tcgtggaccg gctgaagtcg ctgatcaaat acaagggcta ccaggtagcc  3000
ccagccgaac tggagagcat cctgctgcaa caccccaaca tcttcgacgc ggggtcgcc  3060
ggcctgcccg acgacgatgc cggcgagctg cccgccgcag tcgtcgtgct ggaacacggt  3120
aaaaccatga ccgagaagga gatcgtggac tatgtggcca gccaggttac aaccgccaag  3180
aagctgcgcg gtgttgttgt gttcgtggac gaggtgccta aggactgcc cggcaagttg  3240
gacgcccgca gatccgcga gattctcatt aaggccaaga agggcggcaa gatcgccgtg  3300
tgaggagatg ggggaggcta actgaaacac ggaaggagac aataccggaa ggaacccgcg  3360
ctatgacggc aataaaaaga cagaataaaa cgcacgggtc ttgggttgtt tgttcataaa  3420
cgcggggttc ggtcccaggg ctggcactct gtcgatacc caccgagacc ccattgggc   3480
caatacgccc gcgtttcttc cttttcccca ccccacccc caagttcggg tgaaggccca  3540
gggctcgcag ccaatgtcgg gcggcaggcc cctgccatag ccactggccc cgtgggttag  3600
ggacggggtc cccatgggga atggttatg gttcgtgggg gttattattt tgggtgttgc  3660
gtggggtctg gggcgcgcca taggtacccg atgatcctga cgacggagac cgccgtcgtc  3720
gacaagccct atatttatct aagacgcact ggtatgaact tgataccttaa atcacttaga  3780
tcacttaga tgaacgagcc gctggtgacg cttagctcct atcattagat aacttcgtat  3840
agcatacatt atacgaagtt atcgcaggta cctataacta tctggtatga tgggactacc  3900
aaaactttac taggttacca atggcacgct ttccctcagc cgaccgaatt agctaggatg  3960
tgatagtcct tagtgaacgt atcaagaatg gaaacgctag cattgatacgt ccgaattat   4020
gttatatttg gcaagattta atttaattaa aagaattaa atttagctgg caattattag  4080
tcttggggcc actcgtcatt tctaaataac tcatgtggca tgttgtacct ttgtcagcaa  4140
tagctcaggc aaggccagtt cttaaggaat taagcctatg attaaggtgt ttcaagagtt  4200
tatatcacta ccgtttgtat ctacactacg atagtacact ctttgaatg ggaaccatgg   4260
tgtgatcacc gttatctcat cctctcgata gaagaggaag aggttaata aactctccat  4320
tggtatgggt aatggtacaa aaccatcttc tcgcgcattg taaggtctat gggcacatta  4380
tcgaacgcct ccctagtccc tagaatgaac cgaccgtaaa acagagccct ttaggatagc  4440
caatcagtag taatctaacg actagccgtc attcacctgc acctgaggca agcttcacgc  4500
tgccgcaagc actcagggcg caagggctgc taaaggaagc ggaacacgta gaaagccagt  4560
ccgcagaaac ggtgctgacc ccgatgaat gtcagctact gggctatctg acaagggaa   4620
aacgcaagcg caaagagaaa gcaggtagct tgcagtgggc ttacatggcg atagctagac  4680
```

-continued

```
tgggcggttt tatggacagc aagcgaaccg gaattgccag ctggggcgcc ctctggtaag    4740
gttgggaagc cctgcaaagt aaactggatg gctttcttgc cgccaaggat ctgatgcgc    4800
aggggatcaa gatctgatca agagacagga tgaggatcgt ttcgcatgat tgaacaagat    4860
ggattgcacg caggttctcc ggccgcttgg gtggagaggc tattcggcta tgactgggca    4920
caacagacaa tcggctgctc tgatgccgcc gtgttccgac tgtcagcgca ggggcgcccg    4980
gttcttttg tcaagaccga cctgtccggt gccctgaatg aactgcagga cgaggcagcg    5040
cggctatcgt ggctggccac gacgggcgtt ccttgcgcag ctgtgctcga cgttgtcact    5100
gaagcgggaa gggactggct gctattgggc gaagtgccgg gcaggatct cctgtcatct    5160
caccttgctc ctgccgagaa agtatccatc atggctgatg caatgcggcg gctgcatacg    5220
cttgatccgg ctacctgccc attcgaccac caagcgaaac atcgcatcga gcgagcacgt    5280
actcggatgg aagccggtct tgtcgatcag gatgatctgg acgaagagca tcaggggctc    5340
gcgccagccg aactgttcgc caggctcaag gcgcgcatgc ccgacggcga ggatctcgtc    5400
gtgacccatg gcgatgcctg cttgccgaat atcatggtgg aaaatggccg cttttctgga    5460
ttcatcgact gtggccggct gggtgtggcg gaccgctatc aggacatagc gttggctacc    5520
cgtgatattg ctgaagagct tggcggcgaa tgggctgacc gcttcctcgt gctttacggt    5580
atcgccgctc ccgattcgca gcgcatcgcc ttctatcgcc ttcttgacga gttcttctga    5640
gcgggactct ggggttcgca tcgatgcatc gatgcggcgg gtgtggtggt tacgcgtaat    5700
ctgctgcttg caaacaaaaa aaccaccgct accagcggtg gtttgtttgc cggatcaaga    5760
gctaccaact cttttttccga aggtaactgg cttcagcaga gcgcagatac caaatactgt    5820
tcttctagtg tagccgtagt taggccacca cttcaagaac tctgtagcac cgcctacata    5880
cctcgctctg ctaatcctgt taccagtggc tgctgccagt ggcgataagt cgtgtcttac    5940
cgggttggac tcaagacgat agttaccgga taaggcgcag cggtcgggct gaacggggg    6000
ttcgtgcaca cagcccagct tggagcgaac gacctacacc gaactgagat acctacagcg    6060
tgagctatga gaaagcgcca cgcttcccga agggagaaag gcggacaggt atccggtaag    6120
cggcagggtc ggaacaggag agcgcacgag ggagcttcca ggggaaacg cctggtatct    6180
ttatagtcct gtcgggtttc gccacctctg acttgagcgt cgatttttgt gatgctcgtc    6240
agggggggcgg agcctatgga aaaacgccca caacgcatcg ataaaataaa agatttatt    6300
tagtctccag aaaaagggg gaatgaaaga ccccaccctgt aggttggca agctaggtgg    6360
cggccgcaaa aagcaggtgt tgcaactata tagagtcttg atgaccaacg taaacctagg    6420
cctttctaca gggattgtat aaagcctagc aatgagaaga tcacctctgg tagtaaatat    6480
ctttgaggtt atattgtcga tatcttcatc ttcgatgcgc cgtagtttag aagtcataag    6540
tcgataacac gagcgtactg ttagattcct tatacgtttc aaagagagcg ttagtacaca    6600
gaggcgcagg tcaatgctag gaagctacgg gcgacgctga ccgtctctaa ctgtcaacaa    6660
agtatatag aagcaatcat gaatttatc taagtagaga ttatgttcat agtcaccttc    6720
agaagagcta tactcagagg cacgccattt ataagcctat ctagtagaag aattgtggga    6780
ttgtacctac accgagctcc tcctgcttaa cccattctgt atttttgatt aaataactac    6840
gtattacata gtcactttgc gcaaggaaaa atagtgcttt tccgtctatg taaagactaa    6900
tcatatcatt agcgaacgcc ttcctcgttt aggcgtctac tgatagctat cgtactggtc    6960
tgcagcagtg gagcataact tcgtataatg tatgctatac gaagttatag ttcttagcat    7020
tataataagg caggcaatta cttatatcag tcaagtttca aacttagtca gccgggttga    7080
gaacggttta gatccacccc gttatgacgg cttgtcgacg acggcggtct ccgtcgtcag    7140
gatcatacca cgtggtcctg ctattgtctt cccaatcctc cccttgctg tcctgcccca    7200
ccccaccccc cagaatgaaa tgacacctac tcagacaatg cgatgcaatt tcctcatttt    7260
attaggaaag gacagtggga gtggcacctt ccagggtcaa ggaaggcacg gggaggggc    7320
aaacaacaga tggctggcaa ctagaaggca cagtcgaggc taatcagcgt cagttagcct    7380
cccccatctc ccgatccgga cgagtgctgg ggcgtcggtt tccactatcg gcgagtactt    7440
ctacacagtc atcggtccag acggccgcgc ttctgcgcag gatttgtgta cgcccgacag    7500
tcccggctcc ggatcggacg attgcgtcgc atcgaccctg cgcccaagct gcatcatcga    7560
aattgccgtc aaccaagctc tgatagagtt ggtcaagacc aatgcggagc atatacgccc    7620
ggagccgcgc cgatcctgca agctccggat gcctccgctc gaagtagcgc gtctgctgct    7680
ccatacaagc caaccacggc ctccagaaga agatgttcgg gacctcgtat tgggaatccc    7740
cgaacatcgc ctcgctccag tcaatgaccg ctgttatgcg gccattgtcc gtcaggacat    7800
tgttggagcc gaaatccgcg tgcacgaggt gccggacttc ggggcagtcc tcggcccaaa    7860
gcatcagctc atcgagagcc tgcgcgacgg acgcactgac ggtgtcgtcc atcacagttt    7920
gccagtgata cacatgggga tcagcaatcg cgcatatgaa atcacgccat gtagtgtatt    7980
gaccgattcc ttgcggtccg aatgggccga acccgctcgt ctggctaaga tcggccgcag    8040
cgatcgcatc catggcctcc gcgaccggct gcagaacagc gggcagtcg gtttcaggca    8100
ggtcttgcaa cgtgacaccc tgtgcacggc gggagatgca ataggtcagg ctctcgctga    8160
attcccccaat gtcaagcact tccggaatcg ggagcgcggc cgatgcaaag tgccgataaa    8220
cataacgatc tttgtagaaa ccatcggcgc agctatttac ccgcaggaca tatccacgcc    8280
ctcctacatc gaagctgaaa gcacgagatt cttcgccctc cgagagctgc atcaggtcgg    8340
agacgctgtc gaacttttcg atcagaaact ctcgacaga cgtcgcggtg agttcaggct    8400
tttgggccc agggttggac tccacgtctc ccgccaactt gagaaggtca aaattcaaag    8460
tctgtttcac cggtgctgtc tgctcgaagc ggccgggggc cccgactcta gagtaacccg    8520
ggtgcgcggc gtcggtggtg ccggcggggg gcgccaggtc gcaggcggtg tagggctcca    8580
gcaggcggc gaaggccatg acgtgcgcta tgaaggtctg ctcctgcacg ccgtgaacca    8640
ggtgcgcctg cgggccgcgc gcgaacaccg ccacgtcctc gcctgcgtgg gtctcttcgt    8700
ccaggggcac tgctgactgc tgccgatact cgggctcccc gctctcgctc tcggtaacat    8760
ccggccgcagg gccgtccttg agcacatagc ctggaccgtt tccgtatagg aggaccgtgt    8820
aggccttcct gtcccgggcc ttgcagggg ccagccgaa gatggagctc cctcgcaggg    8880
ggtagcctcc gaaggagaag acgtgggagt ggtcggcagt gacgaggctc agcgtgtcct    8940
cctcgctggt gagctggccc gccctctcaa tggcgtcgtc gaacatgatc gtctcagtca    9000
gtgcccggta agccctgctt tcatgatgac catggtcgat gcgaccaccc tccacgaaga    9060
ggaagaagcc gcggggggttc ctgctcagca gcaggccagtt agcctccatca    9120
gggagggtc cagtgtggag tctcggtgga tctcgtattt catgtctcca ggctcaaaga    9180
gacccatgag atgggtcaca gacgggtcca gggaagcctg catgagctca gtgcggttcc    9240
acacataccg ggcaccctgg cgcttcgcca gccattcctg caccagattc ttcccgtcca    9300
gcctggtccc accttggctg tagtcatctg ggtactcagg gtctgggggtt cccatgccaa    9360
acatgtactt tcggcctcca cctaggatca cgtcaatgtc catgttggag atgagctgcg    9420
```

```
tagcgatgtc ctggcacccc tcctggcggg ccgaggcagg cacgtcggcg tccgagtacc   9480
agttgcggtt caccgtgtgg gcgtaggtgc cggctggcga ggcgtgctgc actcgtgtgg   9540
tggttaccac tcccactgac ttccctgctt tcttggcccg attcatcacg gagatgacct   9600
cgttgccgcg tgtcgtgttg cactggttaa agcgggcggc tgcactcaag ccaatggtct   9660
ggaagttgcc cttgaccccg cacaggtagg ccgtggctgt ggctccactg tctggcacat   9720
gtttgtctac attgtatgtc ttggacagag ccacatatgg gaagcggtcc atggccaggg   9780
gtatctcagg ccccagtttg tccttcttct gcccttttag gatcctggca gctgtcaccg   9840
tagacacccc catcccatcg cccaggaaga tgatgaggtt cttggcggct gtctgtgcag   9900
gctgcagctt cttggcggca cccagggcct cggctgcctc gcggttccag aagtccgggt   9960
tctcctcctc aactgggatg atgcccaggg agagctgtag cctcaggccc agcagcagca  10020
gcagcagcag catggtggat gcggccgctc tagacacgac acctgaaatg gaagaaaaaa  10080
actttgaacc actgtctgag gcttgagaat gaaccaagat ccaaactcaa aaagggcaaa  10140
ttccaaggag aattacatca agtgccaagc tggcctaact tcagtctcca cccactcagt  10200
gtgggaaaac tccatcgcat aaaaccccctc cccccaacct aaagacgacg tactccaaaa  10260
gctcgagaac taatcgaggt gcctggacgg cgcccggtac tccgtggagt cacatgaagc  10320
gacggctgag gacggaaagg ccctttcct tgtgtgggt gactcacccg cccgctctcc  10380
cgagcgccgc gtcctccatt ttgagctccc tgcagcaggg ccggaagcg gccatctttc  10440
cgctcacgca actggtgccg accggggcca ccttgccgcc caggcgggg cgatacacgg  10500
cggcgcgagg ccaggcacca gagcaggccg gccagcttga gactaccccc gtccgattct  10560
cggtggccgc gctcgcaggc cccgcctcgc cgaacatgtg cgctgggacg cacgggcccc  10620
gtcgccgccc gcggccccaa aaaccgaaat accagtgtgc agatcttggc ccgcatttac  10680
aagactatct tgccagaaaa caaaaagtcgc agcaggtcat caaaaatttt aaatggctag  10740
agacttatcg aaagcagcga gacaggcgcg aaggtgccac cagattgcca cgcggcggcc  10800
ccagcgccca agcaggcct caactcaagc acgaggcgaa ggggctcctt aagcgcaagg  10860
cctcgaactc tcccacccac ttccaacccg aagctcggga tcaagaatca cgtactgcag  10920
ccagggcgt ggaagtaatt caaggcacgc aagggccata acccgtaaag aggccaggcc  10980
cgcgggaacc acacacgca cttacctgtg ttctggcgtc tagagtcgac tagcttttaa  11040
gcgggtcgct gcagggtcgc tcggtgttcg aggccacacg cgtcaccttla atatgcgaag  11100
tggacctggg accgcgccgc cccgactgca tctgcgtgtt cgaattcgcc aatgacaaga  11160
cgctgggcgg ggttttgtgtc atcatagaac taaagacatg caaatatatt tcttccgggga  11220
acaccgccag caaacgcgag caacgggcca cggggatgaa gcagctgcgc cactccctga  11280
agctcctgca gtccctcgcg cctccggggt acaagatagt gtacctgtgc cccgtcctgg  11340
tgtttgtcgc ccaacggacg ctccgcgtca gccgcgtgac ccggctcgtc ccgcagaagg  11400
tctccggtaa tatcaccgca gtcgtgcgga tgctccagag cctgtccacg tatacggtcc  11460
ccatggagcc taggaccag cgagcccgtc gccgccgcg cggcgccgcc cgggggtctg  11520
cgagcagacc gaaaaggtca cactctgggg cgcgccgaccc gccgagtca gcggcccgcc  11580
agttaccacc cgccgaccaa accccgcct ccacggaggg cggggggggtg cttaagagga  11640
tcgcggcgct cttctgcgtg cccgtggcca ccaagaccaa accccgagcc gcctccgaat  11700
gagagtgttt cgttccttcc ccctccccccc gcgtcagaca aaccctaacc accgcttaag  11760
cggcccccgc gaggtccgaa gactcattta gatctaagct attctcagct gccatggaaa  11820
atcgataccg tcttcgctag aactagtcta atgttgccat gggtagcata tactacccaa  11880
atatctggat agcatatgct atcctaatct atatctgggt agcataggct atcctaatct  11940
atatctgggt agcatatgct atcctaatct atatctgggt agtatatgct atccttattt  12000
atatctgggt agcataggct atcctaatct atatctgggt agcatatgct atcctaatct  12060
atatctgggt agtatatgct atcctaatct gtatccgggt agcatatgct atcctaatag  12120
agattagggt agtatatgct atcctaattt atatctgggt agcatatact acccaaatat  12180
ctggatagca tatgctatcc taatctatat ctgggtagca tatgctatcc taatctatat  12240
ctgggtagca taggctatcc taatctatat ctgggtagca tatgctatcc taatctatat  12300
ctgggtagta tatgctatcc taatttatat ctgggtagca taggctatcc taatctatat  12360
ctgggtagca tatgctatcc taatctatat ctgggtagta tatgctatcc taatctgtat  12420
ccgggtagca tatgctatcc tcatgcgtat acagtcgtat tatgataccc gactagtgga  12480
tccccgggc tgcaggaatt cgatggggat ctgtaccgtt gccggtcgga tctgtaccgt  12540
tgccggtcgg atctgtaccg ttgccggtcg gatctgtacc gttgccggtc ggatctgtac  12600
cgttgccggt cggatctgta ccgttgccgg tcggatctgt accgttgccg gtcggatctg  12660
taccgttgcc ggtcggatct gtaccgttgc cggtcggatc tgtaccgttg ccggtcggat  12720
cagcttcaga agatggcgga gggcctccaa cacagtaatt ttcctcccga cagatctcct  12780
agaatgtttc caccaatca ttactatgac aacagctgtt ttttttagta ttaagcagag  12840
gccgggggcc cctggcctcc gcttactctg gagaaaaaga agagaggcat tgtagaggct  12900
tccagaggca acttgtcaaa acaggactgg cgacctgcag gcatgcaagc tgaccctgca  12960
gaatgtgtgt cagttagggt gtggaaagtc cccaggctcc ccagcaggaa gaagtatgca  13020
aagcatgcat ctcaattagt cagcaaccag gtgtggaaag tccccaggct ccccagcagg  13080
cagaagtatg caaagcatgc atctcaatta gtcagcaacc atagtcccgc ccctaactcc  13140
gcccatcccg ccctaactc cgcccagttc cgcccattct ccgccccatg gctgactaat  13200
tttttttatt tatgcagagg ccgaggccgc ctcggcctct gagctattcc agaagtagtg  13260
aggaggcttt tttggaggc                                               13279

SEQ ID NO: 2           moltype = DNA  length = 11795
FEATURE                Location/Qualifiers
source                 1..11795
                       mol_type = other DNA
                       organism = synthetic construct
SEQUENCE: 2
cgcgccatag gtaccggctt gtcgacgacg gcggtctccg tcgtcaggat catctaatga    60
taggagctaa gcgtcaccag cggtcgtttc atctaagtga tttgaagttc ctatactttg   120
tagagaaatag gaacttcgga ataggaactt caatgtgctg caatctcaaa tttcatacca   180
gtgcgtctta gataaatata gataacttcg tataggatac tttatacgaa gttatggtac   240
ctataactat ctggtatgat gggactacca aaacttttact aggttaccaa tggcacgctt   300
tccctcagcc gaccgaatta gctaggatgt gatagtcctt agtgaacgta tcaagaatgg   360
aaacagctga ttgatacgtc cgaattttatg ttatatttgg caagatttaa tttaattaaa   420
```

```
aagaattata tttagctggc aattattagt cttggggcca ctcgtcattt ctaaataact   480
catgtggcat gttgtacctt tgtcagcaat agctcaggca aggccagttc ttaaggaatt   540
aagcctatga ttaaggtgtt tcaagagttt atatcactac cgtttgtatc tacactacga   600
tagtacactc ttttgaatgg gaaccatggt gtgatcaccg ttatctcatc ctctcgatag   660
aagaggaaga ggttaaatata actctccatt ggtatgggta atggtacaaa accatcttct   720
cgcgcattgt aaggtctatg ggcacattat cgaacgcctc cctagtccct agaatgaacc   780
gaccgtaaaa cagagccctt taggatagcc aatcagtagt aatctaacga ctagccgtca   840
ttaatgcttc acgctgccgc aagcactcag ggcgcaaggg ctgctaaagg aagcggaaca   900
cgtagaaagc cagtccgcag aaacggtgct gaccccggat gaatgtcagc tactgggcta   960
tctggacaag ggaaaacgca agcgcaaaga gaaagcaggt agcttgcagt gggccttacat  1020
ggcgatagct agactgggcg gttttatgga cagcaagcga accggaattg ccagctgggg  1080
cgccctctgg taaggttggg aagccctgca aagtaaactg gatggctttc ttgccgccaa  1140
ggatctgatg gcgcagggga tcaagatctg atcaagagac aggatgagga tcgtttcgca  1200
tgattgaaca agatggattg cacgcaggtt ctccggccgc ttgggtgagg aggctattcg  1260
gctatgactg ggcacaacag acaatcggct gctctgatgc cgccgtgttc cggctgtcag  1320
cgcaggggcg cccggttctt tttgtcaaga ccgacctgtc cggtgccctg aatgaactgc  1380
aggacgaggc agcgcggcta tcgtggctgg ccacgacggg cgttccttgc gcagctgtgc  1440
tcgacgttgt cactgaagcg ggaagggact ggctgctatt gggcgaagtg ccggggcagg  1500
atctcctgtc atctcacctt gctcctgccg agaaagtatc catcatggct gatgcaatgc  1560
ggcggctgca tacgcttgat ccggctacct gcccattcga ccaccaagcg aaacatcgca  1620
tcgagcgagc acgtactcgg atggaagccg gtcttgtcga tcaggatgat ctggacgaag  1680
agcatcaggg gctcgcgcca gccgaactgt tcgccaggct caaggcgcgc atgcccgacg  1740
gcgaggatct cgtcgtgacc catggcgatg cctgcttgcc gaatatcatg gtggaaaatg  1800
gccgcttttc tggattcatc gactgtggcc ggctgggtgt ggcggaccgc tatcaggaca  1860
tagcgttggc tacccgtgat attgctgaag agcttggcgg cgaatgggct gaccgcttcc  1920
tcgtgcttta cggtatcgcc gctcccgatt cgcagcgcat cgccttctat cgccttcttg  1980
acgagttctt ctgagcggga ctctgggtt cgcatcgatg catcgatgcg gcggtgtgg  2040
tggttacgcg taatctgctg cttgcaaaca aaaaaaccac cgctaccagc ggtggtttgt  2100
ttgccggatc aagagctacc aactcttttt ccgaaggtaa ctggcttcag cagagcgcag  2160
ataccaaata ctgttcttct agtgtagccg tagttaggcc accacttcaa gaactctgta  2220
gcaccgccta catacctcgc tctgctaatc ctgttaccag tggctgctgc cagtggcgat  2280
aagtcgtgtc ttaccgggtt ggactcaaga cgatagttac cggataaggc gcagcggtcg  2340
ggctgaacgg ggggttcgtg cacacagccc agcttggagc gaacgaccta caccgaactg  2400
agatacctac agcgtgagct atgagaaagc gccacgcttc ccgaagggag aaaggcggac  2460
aggtatccgg taagcggcag ggtcggaaca ggagagcgca cgagggagct tccaggggga  2520
aacgcctggt atctttatag tcctgtcggg tttcgccacc tctgacttga gcgtcgattt  2580
ttgtgatgct cgtcaggggg gcggagccta tggaaaaacg ccagcaacgc atcgataaaa  2640
taaaagattt tatttagtct ccagaaaaag ggggaatga agaccccac ctgtaggttt  2700
ggcaagctag gtggcggccg cattaatgtt gcaactatat agatgcttga tgaccaacgt  2760
aaacctaggc ctttctacag ggattgtata aagcctagca atgagaagat cacctctggt  2820
agtaaatatc tttgaggtta tattgtcgat atcttcatct tcgatgcgcc gtagtttaga  2880
agtcataagt cgataacacg agcgtactgt tagattcctt atacgtttca aagagagcgt  2940
tagtacacag aggcgcaggt caatgctagg aagctacggg cgacgctgac cgtctctaac  3000
tgtcaacaaa gttataatga agcaatcatg aattttatct aagtagagat tatgttcata  3060
gtcaccttca gaagagctat actcagaggc acgccattta taagcctatc tagtagaaga  3120
attgtgggat tgtacctaca ccgagctcct cctgcttaac ccattctgta ttttttgatta  3180
aataactacg tattacatag tcactttgcg caaggaaata tatgtctttt ccgtctatgt  3240
aaagactaat catatcatta gcgaacgcct tcctcgtttta ggcgtctact gatagctatc  3300
gtactggtct gcagcacgtg atgatcctga cgacggagac cgccgtcgtc gacaagccct  3360
aatgatagga gctaagcgtc accagcggct cgttcatcta agtgatttga agttcctata  3420
cttttttgaag aataggaact tcggaatagg aacttcagtg tgctgcaatc tcaaatttca  3480
taccagtgcg tcttagataa atatagataa cttcgtataa tgtatgctat acgaagttat  3540
cacgtggtcc tgctattgtc ttcccaatcc tccccccttgc tgtcctgccc caccccaccc  3600
cccagaatag aatgacacct actcagacaa tgcgatgcaa tttcctcatt ttattaggaa  3660
aggacaggtag gagtggcacc ttccagggtc aaggaaggca cggggggaggg gcaaacaaca  3720
gatggctggc aactagaagg cacagtcgag gctaatcagc gtcagttagc ctcccccatc  3780
tcccgatccg gacgagtgct ggggcgtcgg tttccactat cggcgagtac ttctacacag  3840
ccatcggtcc agacggccgc gcttctgcgg gcgatttgtg tacgcccgac agtcccggct  3900
ccggatcgca cgattgcgtc gcatcgaccc tgcgcccaag ctgcatcatc gaaattgcag  3960
tcaaccaagc tctgatagag ttggtcaaga ccaatgcgga gcatatacgc ccggagccgc  4020
ggcgatcctg caagctccgg atgcctccgc tcgaagtagc gcgtctgctg ctccatacaa  4080
gccaaccacg gcctccagaa gaagatgttg gcgacctcgt attgggaatc cccgaacatc  4140
gcctcgctcc agtcaatgac cgctgttatg cggccattgt ccgtcaggac attgttggag  4200
ccgaaatccg cgtgcacgag gtgccggact tcggggccga cctcggctcc aagcatccgc  4260
tcatcgagag cctgcgcgac ggacgcactg acggtgtcgt ccatcacagt ttgccagtga  4320
tacacatggg gatcagcaat cgcgcatatg aaatcacgcc atgtagtgta ttgaccgatt  4380
ccttgcggtc cgaatgggcc gaacccgctc gtctggctaa gatcggccgc agcgatcgca  4440
tccatggcct ccgcgaccgg ctgcagaaca gcgggcagtt cggtttcagg caggtcttgc  4500
aacgtgacac cctgtgcacg gcgggagatg caataggctc ggctctcgct gaattcccca  4560
atgtcaagca cttccggaat cgggagcgcg gccgatgcaa agtgccgata aacataacga  4620
tcttttgtaga aaccatcggc gcagctattt acccgcagga catatccacg cctcctacaa  4680
tcgaagctga aagcacgaga ttcttcgccc tccgagagct gcatcaggtc ggagacgctg  4740
tcgaacttttt cgatcagaaa cttctcgaca gacgtcgcgg tgagttcagg cttttttggc  4800
ccaggttgg actccacgtc tcccgccaac ttgagaaggt caaaattcaa agtctgtttc  4860
accggtgctg tctgctcgaa gcggccggcc gccccgactc tagagtaacc cgggtgcgcg  4920
gcgtcggtgg tgccgcgg gggcgccagg tcgcaggcgg tgtagggctc caggcaggcg  4980
gcgaaggcca tgacgtgcgc tatgaaggtc tgctcctgca cgccgtgaac caggtgcgcc  5040
tgcgggccgc gcgcgaacac cgccacgtcc tcgcctgcgt gggtctcttc gtccagggc  5100
actgctgact gctgccgata ctcggggctc ccgctctcgc tctcggtaac atccggccgg  5160
```

```
gcgccgtcct tgagcacata gcctggaccg tttccgtata ggaggaccgt gtaggccttc   5220
ctgtcccggg ccttgccagg ggccagcccg aagatggagc tccctcgcag ggggtagcct   5280
ccgaaggaga agacgtggga gtggtcggca gtgacgaggc tcagcgtgtc ctcctcgctg   5340
gtgagctggc ccgccctctc aatggcgtcg tcgaacatga tcgtctcagt cagtgcccgg   5400
taagccctgc tttcatgatg accatggtcg atgcgaccac cctccacgaa gaggaagaag   5460
ccgcggggt tcctgctcag caggcgcagg gcagcctctg tcatctccat cagggagggg   5520
tccagtgtgg agtctcggtg gatctcgtat ttcatgtctc caggctcaaa gagacccatg   5580
agatgggtca cagacgggtc cagggaagcc tgcatgagct cagtgcggtt ccacacatac   5640
cgggcaccct ggcgcttcgc cagccattcc tgcaccagat tcttcccgtc cagcctggtc   5700
ccaccttggc tgtagtcatc tgggtactca gggtctgggg ttcccatgcg aaacatgtac   5760
tttcggcctc cacctaggat cacgtcaatg tccatgttgg agatgagctg cgtagcgatg   5820
tcctggcacc cctcctggcg ggccgaggca ggcacgtcgg cgtccgagta ccagttgcgg   5880
ttcaccgtgt gggcgtaggt gccggctggc gaggcgtgct gcactcgtgt ggtggttacc   5940
actcccactg acttccctgc tttcttggcc cgattcatca cggagatgac ctcgttgccg   6000
cgtgtcgtgt tgcactggtt aaagcggggcg gctgcactca agccaatggt ctggaagttg   6060
cccttgaccc cgcacaggta ggccgtggct gtggctccac tgtctggcac atgtttgtct   6120
acattgtatg tcttggacag agccacatat gggaagcggt ccatgccagg gggtatctca   6180
ggccccagtt tgtccttctt ctgccctttt aggatcctgg cagctgtcac cgtagacacc   6240
cccatcccat cgcccaggaa gatgatgagg ttcttggcgg ctgtctgtgc aggctgcagc   6300
ttcttggcgg cacccagggc ctcggctgcc tcgcggttcc agaagtccgg gttctcctcc   6360
tcaactggga tgatgcccag ggagagctgt agcctcaggc ccagcagcag cagcagcagc   6420
agcatggtgg atgcggccgc tctagacacg cacctgaaa tggaaggaaa aaactttgaa   6480
ccactgtctg aggcttgaga atgaaccaag atccaaactc aaaaagggca aattccaagg   6540
agaattacat caagtgccaa gctggcctaa cttcagtctc cacccactca gtgtggggaa   6600
actccatcgc ataaaacccc tcccccaac ctaaagacga cgtactccaa aagctcgaga   6660
actaatcgag gtgcctggac ggcgcccggt actccgtgga gtcacatgaa gcgacgggtc   6720
aggacggaaa ggcccttttc ctttgtgtgg gtgactcacc cgcccgctct cccgagcgcc   6780
gcgtcctcca ttttgagctc cctgcagcag ggcggaaag cggccatctt tccgctcacg   6840
caactggtgc cgaccgggcc agccttgccg cccaggcgg ggcgatacac ggcggcgcga   6900
ggccaggcac cagagcaggc cggccagctt gagactaccc ccgtccgatt ctcggttgcc   6960
gcgctcgcag gccccgcctc gccgaacatg tgcgctggga cgcacgggcc ccgtcgccgc   7020
ccgcggcccc aaaaaccgaa ataccagtgt gcagatcttg gccgcatttt acaagactat   7080
cttgccagaa aaaagcgtc gcagcaggtc atcaaaaatt ttaaatggct agagacttat   7140
cgaaagcagc gagacaggcg cgaaggtgcc accagattcc cacgcggcgg ccccagcgcc   7200
caagcaggc ctcaactcaa gcacgaggcg aaggggctcc ttaagcgcaa ggcctcgaac   7260
tctcccaccc acttccaacc cgaagctcgg gatcaagaat cacgtactgc agccaggggc   7320
gtggaagtaa ttccaaggcac gcaagggcca taacccgtaa agaggccagg cccgcgggaa   7380
ccacacacgg cacttacctg tgttctggcg tctagagtcg actagctttt aagcgggtcg   7440
ctgcaggtc gctcggtgtt cgaggccaca cgcgtcacct taatatgcga agtggacctg   7500
ggaccgcgcc gccccgactg catctgcgtg ttcgaattcg ccaatgacaa gacgctgggc   7560
gggggtttgtg tcatcataga actaaagaca tgcaaatata ttcttccgg ggacaccgcc   7620
agcaaacgcg agcaacgggc cacggggatg aagcagctgc gccactccct gaagctcctg   7680
cagtccctcg cgcctccggg tgacaagata gtgtacctgt gccccgtcct ggtgttgtc   7740
gcccaacgga cgctccgcgt cagccgcgtg acccggctcg tcccgcagaa ggtctccggt   7800
aatatccacg cagtcgtgcg gatgctccag agcctgtcca cgtatacggt ccccatggag   7860
cctaggaccc agcgagcccg tcgccgccgc ggcggcgccg cccgggggtc tgcgagcaga   7920
ccgaaaaggt cacactctgg ggcgcggac ccgcccgagt cggcgccccg ccagttacca   7980
cccgccgacc aaaccccgc ctccacggag ggcggggggg tgcttaagag gatcgcggc   8040
ctcttctgcg tgcccgtggc caccaagacc aaacccgag ccgcctccga atgagagtgt   8100
ttcgttcctt cccctcccc ccgcgtcaga caaaccctaa ccaccgctta agcggccccc   8160
gcgaggtccg aagactcatt tagatctaag ctattctcag ctgccatgga aaatcgatac   8220
cgtcttcgct agaactagtc taatgttgcc atgggtagca tatactaccc aaatatctgg   8280
atagcatatg ctatcctaat ctatatctgg gtagcatagg ctatcctaat ctatatctgg   8340
gtagcatatg ctatcctaat ctatatctgg gtagtatatg ctatcctaat ttatatctgg   8400
gtagcatagg ctatcctaat ctatatctgg gtagcatatg ctatcctaat ctatatctgg   8460
gtagtatatg ctatcctaat ctgtatccgg gtagcatatg ctatcctaat agagattagg   8520
gtagtatatg ctatcctaat ttatatctgg gtagcatata ctacccaaat atctggatag   8580
catatgctat cctaatctat atctgggtag catatgctat cctaatctat atctgggtag   8640
cataggctat cctaatctat atctgggtag catatgctat cctaatctat atctgggtag   8700
tatatgctat cctaatttat atctgggtag cataggctat cctaatctat atctgggtag   8760
catatgctat cctaatctat atctgggtag tatatgctat cctaatctgt atccgggtag   8820
catatgctat cctcatgcgt atacagtcag catatgatac ccgactagtg gatcctgctg   8880
taccgttgcc ggtcggatct gtaccgttgc cggtcggatc tgtaccgttg ccggtcggat   8940
ctgtaccgtt gccggtcgga tctgtaccgt tgccggtcgg atctgtaccg ttgccggtcg   9000
gatctgtacc gttgccggtc ggatctgtac cgttgccggt cggatctgta ccgttgccgg   9060
tcatcctgca ggtcgatcga ctctagtatg gtgcactctc agtacaatct gctctgatgc   9120
cgcatagtta agccagtatc tgctccctgc ttgtgtgttg gaggtcgctg agtagtgcgc   9180
gagcaaaatt taagctacaa caaggcaagg cttgaccgac aattgcatga agaatctgct   9240
tagggttagg cgttttgcgc tgcttccgcga tgtacgggcc agatatacgc gtatctgagg   9300
ggactagggt gtgtttaggc gaaaagcggg gcttcggttg tacgcggtta ggagtcccct   9360
caggatatag tagtttcgct tttgcatagg gaggggaaa tgtagtctta tgcaatactc   9420
ttgtagtctt gcaacatggt aacgatgagt tagcaacatg ccttacaagg agagaaaaag   9480
caccgtgcat gccgattggt ggaagtaagg tggtacgatc gtgccttatt aggaaggcaa   9540
cagacgggtc tgacatggat tggacgaacc actgaattcc gcattgcaga gatattgtat   9600
ttaagtgcct agctcgatac aataaacgcc atttgaccat tcaccacatt ggtgtgcacc   9660
tccaagctgg tagaggatcg gtcgatcgac tctagacagg taagtggcgt ttctcgggga   9720
gccagctgcg tccgctgtcg tgctgtcggt gtagtactag caagcgttaa gtccccatct   9780
ggctgcggcc taccgaagag tggtcttcac gtcacacgcg gtcccacgca cgtggttggt   9840
ttggtcgctt ctggttactg actactaagc agccttttct ttttttcctt caggttctag   9900
```

```
agcggccgcc accgaaacgc cgtacgccac catggagtgg tcttgggtgt tcctgttctt   9960
tctgtccgtg accacaggcg tccacagcca gtcggtggag gagtccgggg gaggcctggt  10020
caagcctgag ggatccctga cactcacctg cacagcctct ggattctcct tcagttccaa  10080
ctactggata tgctgggtcc gccaggctcc ggggaagggg ctggagtgga tcgcatgcat  10140
ttatgctggt agtgatagta ccactgacta cgcgagctgg gcgaaaggcc gattcaccat  10200
ctccaaaacc tcgtcgacca cggtgactct gcaaatgacc agtctgacag ccgcggacac  10260
ggccacctat ttctgtgcga gaggtactga tcgtagtgct gactacttta acttgtgggg  10320
cccaggcacc ctggtcacca tctcttcagc tggaggaggc ggtagtggtg gtggtggatc  10380
tggtggtggt ggatccgccg atctgaccca gactccagcc tcgatgtctg cagctgtggg  10440
aggcacagtc accatcaact gccaggccag tcagagtgtt agtagtaaca accgcttagc  10500
ctggtatcag cagaaaccag gcagcctcc caagctcctt atctacaggg catccactct  10560
ggcatctggg gtcccatcgc ggttcaaagg cagtggatct gggacacagt tcactctcac  10620
catcagcgac ctggagtgtg ccgatgctgc cacttactac tgtcagagct attattgggg  10680
tagtagtaat agttataatt cctggcttt cggcggaggg accagggtgg tcgtcaaagg  10740
tgctgacaag acccacacct gtccccttg ccctgctcct gagctgctgg gaggccctag  10800
cgtgttcctg ttcccccta agcccaagga caccctgatg atctccagga cccccgaagt  10860
gacctgcgtg gtggtggatg tgagccacga ggaccctgag gtgaagttca actggtacgt  10920
ggacggcgtg gaggtgcaca acgccaagac aaaacccgag gaggagcagt acaacagcac  10980
atatcgggtg gtgagcgtgc tgaccgtgct gcaccaggac tggctgaacg gcaaggagta  11040
caagtgcaag gtgtccaaca aggccctccc cgccccatt gagaagacca tctccaaggc  11100
caagggccag cctagggagc cccaggtgta cacactgcct cccagcaggg acgagctgac  11160
caagaaccag gtgagcctga cctgcctggt gaagggcttc tacccctccg atatcgccgt  11220
ggagtgggag tccaatggcc agcccgaaaa caactacaag accacccccc ctgtgctgga  11280
ctccgatggc agcttcttcc tctactccaa gctgaccgtg gacaagtccc ggtggcagca  11340
gggcaacgtg ttcagctgtt ccgtgatgca cgaggccctg cacaaccatt acacccagaa  11400
gtccctgagc ctgtcccccg gaaaatgatg gggcgcccg cttcgaagcg acttttgtcc  11460
cgaattcctg cagcccctag ctagtctttc cgatcgatgg aaggatccgt cggagctcta  11520
ccttgcggcc gcgacatgat aagatacatt gatgagtttg gacaaaccac aactagaatg  11580
cagtgaaaaa aatgctttat ttgtgaaatt tgtgatgcta ttgctttatt tgtgaaattt  11640
gtgatgctat tgctttattt gtaaccatta taagctgcaa taaacaagtt aacaacaaca  11700
attgcattca ttttatgttt caggttcagg gggaggtgtg ggaggttttt taaagcaagt  11760
aaaacctcta caaatgtggt agatcatttg acccg                            11795

SEQ ID NO: 3          moltype = DNA  length = 10963
FEATURE               Location/Qualifiers
source                1..10963
                      mol_type = other DNA
                      organism = synthetic construct
SEQUENCE: 3
cgcgccatag gtaccggctt gtcgacgacg gcggtctccg tcgtcaggat catctaatga     60
taggagctaa gcgtcaccag cggctcgttc atctaagtga tttgaagttc ctatactttc    120
tagagaatag gaacttcgga ataggaactt caatgtgctg caatctcaaa tttcatacca    180
gtgcgtctta gataaatata gataacttcg tataggatac tttatcgaa gttatggtac    240
ctataactat ctggtatgat gggactacca aaactttact aggttaccaa tggcacgctt    300
tccctcagcc gaccgaatta gctaggatgt gatagtcctt agtgaacgta tcaagaatgg    360
aaacagctga ttgatacgtc cgaatttatg ttatatttgg caagatttaa tttaattaaa    420
aagaattata tttagctggc aattattagt cttggggcca ctcgtcattt ctaaataact    480
catgtggcat gttgtacctt tgtcagcaat agctcaggca aggccagttc ttaaggaatt    540
aagcctatga ttaaggtgtt tcaagagttt atatcactac cgtttgtatc tacactacga    600
tagtacactc ttttgaatgg gaaccatggt gtgatcaccg ttatctcatc ctctcgatag    660
aagaggaaga ggttaatata actctccatt ggtatgggta atggtacaaa accatcttct    720
cgcgcattgt aagtctatg ggcacattat cgaacgcctc cctagtccct agaatgaacc    780
gaccgtaaaa cagagccctt taggatagcc aatcagtagt aatctaacga ctagccgtca    840
ttaatgcttc acgctgccgc aagcactcag ggcgcaaggg ctgctaaagg aagcggaaca    900
cgtagaaagc cagtccgcag aaacgtgct gaccccgagt gaatgtcagc tactgggcta    960
tctggacaag ggaaaacgca agcgcaaaga gaaagcaggt agcttgcagt gggcttacat   1020
ggcgatagct agactgggcg gttttatgga cagcaagcga accggaattg ccagctgggg   1080
cgccctctgt aaggtttggg aagccctgca agtaaactg gatggctttc ttgccgccaa   1140
ggatctgatg gcgcagggga tcaagatctg atcaagagac aggatgagga tcgtttcgca   1200
tgattgaaca agatggattg cacgcaggtt ctccggccgc ttgggtggag aggctattcg   1260
gctatgactg ggcacaacag acaatcggct gctctgatgc cgccgtgttc cggctgtcag   1320
cgcaggggcg cccggttctt tttgtcaaga ccgacctgtc cggtgccctg aatgaactgc   1380
aggacgagge agcgcggcta tcgtggctgg ccacgacggg cgttccttgc gcagctgtgc   1440
tcgacgttgt cactgaagcg ggaagggact ggctgctatt gggcgaagtg ccggggcagg   1500
atctcctgtc atctcacctt gctcctgccg agaaagtatc catcatggct gatgcaatgc   1560
ggcggctgca tacgcttgat ccggctacct gcccattcga ccaccaagcg aaacatcgca   1620
tcgagcgagc acgtactcgg atggaagccg gtcttgtcga tcaggatgat ctggacgaag   1680
agcatcaggg gctcgcgcca gccgaactgt tcgccaggct caaggcgcgc atgcccgacg   1740
gcgaggatct cgtcgtgacc catggcgatg cctgcttgcc gaatatcatg gtggaaaatg   1800
gccgcttttc tggattcatc gactgtggcc ggctgggtgt ggcggaccgc tatcaggaca   1860
tagcgttggc tacccgtgat attgctgaag agcttggcgg cgaatgggct gaccgcttcc   1920
tcgtgcttta cggtatcgcc gctcccgatt cgcagcgcat cgccttctat cgccttcttg   1980
acgagttctt ctgagcggga ctctggggtt cgcatcgatg catcgatgcg gcgggtgtgg   2040
tggttacgcg taatctgctg cttgcaaaca aaaaaccacc gctaccagc ggtggtttgt   2100
ttgccggatc aagagctacc aactcttttt ccgaagtaa ctggcttcag cagagcgcag   2160
ataccaaata ctgttcttct agtgtagccg tagttaggcc accacttcaa gaactctgta   2220
gcaccgccta catacctcgc tctgctaatc ctgttaccag tggctgctgc cagtggcgat   2280
aagtcgtgtc ttaccgggtt ggactcaaga cgatagttac cggataaggc gcagcggtcg   2340
ggctgaacgg ggggttcgtg cacacagccc agcttggagc gaacgaccta caccgaactg   2400
```

```
agatacctac agcgtgagct atgagaaagc gccacgcttc ccgaaggag aaaggcggac 2460
aggtatccgg taagcggcag ggtcggaaca ggagagcgca cgaggagct tccagggga 2520
aacgcctggt atctttatag tcctgtcggg tttcgccacc tctgacttga gcgtcgattt 2580
ttgtgatgct cgtcagggg gcggagccta tggaaaacg ccagcaacgc atcgataaaa 2640
taaaagattt tatttagtct ccagaaaaag ggggaatga aagaccccac ctgtaggttt 2700
ggcaagctag gtggcggccg cattaatgtt gcaactatat agagtcttga tgaccaacgt 2760
aaacctaggc cttctacag ggattgtata aagcctagca atgagaagat cacctctggt 2820
agtaaatatc tttgaggtta tattgtcgat atcttcatct tcgatgcgcc gtagttaga 2880
agtcataagt cgataacacg agcgtactgt tagattcctt atacgtttca aagagagcgt 2940
tagtacacag aggcgcaggt caatgctagg aagctacggg cgacgctgac cgtctctaac 3000
tgtcaacaaa gttataatga agcaatcatg aattttatct aagtagagat tatgttcata 3060
gtcaccttca gaagagctat actcagaggc acgccattta taagcctatc tagtagaaga 3120
attgtgggat tgtacctaca ccgagctcct cctgcttaac ccattctgta ttttttgatta 3180
aataactacg tattacatag tcactttgcg caaggaaaaa tagtgctttt ccgtctatgt 3240
aaagactaat catatcatta gcgaacgcct tcctcgttta ggcgtctact gatagctatc 3300
gtactggtct gcagcacgtg atgatcctga cgacggagac cgccgtcgtc gacaagccct 3360
aatgatagga gctaagcgtc accagcggct cgttcatcta agtgattga agttcctata 3420
cttttgaag aataggaact tcggaatagg aacttcaatg tgctgcaatc tcaaattca 3480
taccagtgcg tcttagataa atatagataa cttcgtataa tgtatgctat acgaagttat 3540
cacgtggtcc tgctattgtc ttcccaatcc tccccttgc tgtcctgccc caccccaccc 3600
cccagaatag aatgacacct actcagacaa tgcgatgcaa tttcctcatt ttattaggaa 3660
aggacagtgg gagtggcacc ttccagggtc aaggaaggca cgggggaggg gcaaacaaca 3720
gatggctggc aactagaagg cacagtcgag gctaatcagc gtcagttagc ctccccccatc 3780
tcccgatccg gacgagtgct ggggcgtcgg ttttccactat cggcgagtac ttctacacag 3840
ccatcggtcc agacgccgc gcttctgcgg gcgatttgtg tacgcccgac agtccccggct 3900
ccggatcgga cgattgcgtc gcatcgaccc tgcgcccaag ctgcatcatc gaaattgccg 3960
tcaaccaagc tctgatagag ttggtcaaga ccaatgcgga gcatatacgc ccggagccgc 4020
ggcgatcctg caagctccgg atgcctccgc tcgaagtagc gcgtcgctg ctccatacaa 4080
gccaaccacg gcctccagaa gaagatgttg gcgacctcgt attggggaatc cccgaacatc 4140
gcctcgctcc agtcaatgac cgctgttatg cggcccattgt ccgtcaggac attgttggag 4200
ccgaaatccg cgtgcacgag gtgccggact tcggggcagt cctcggccca aagcatcagc 4260
tcatccgagag cctgcgcgac ggacgcactg acgggtgtcgt ccatcacagt ttgccagtga 4320
tacacatggg gatcagcaat cgcgcatatg aaatcacgcc atgtagtgta ttgaccgatt 4380
ccttgcggtc cgaatgggcc gaacccgctc gtctggctaa gatcggccgc agcgatcga 4440
tccatggcct ccgcgaccgg ctgcagaaca gcggggcagt cggtttcagg caggtcttgc 4500
aacgtgacac cctgtgcacg gcgggagatg caataggtca ggctctcgct gaattcccca 4560
atgtcaagca cttccggaat cgggagcgcg gccgatgcaa agtgccgata acataacga 4620
tctttgtaga aaccatcggc gcagctattt acccgcagga catatccacg ccctcctaca 4680
tcgaagctga aagcacgaga ttcttcgccc tccgagagct gcatcaggtc ggagacgctg 4740
tcgaactttt cgatcagaaa cttctcgaca gacgtcgcgg tgagttcagg cttttgggc 4800
ccagggttgg actccacgtc tcccgccaac ttgagaaggt caaaattcaa agtctgtttc 4860
accggtgctg tctgctcgaa gcggccggcc gccccgactc tagagtaacc cggggtgcgcg 4920
gcgtcggtgg tgccggcagg gggcgccagg tcgcaggcgg tgtagggctc caggcaggcg 4980
gcgaaggcca tgacgtgcgc tatgaagtc tgctcctgca cgccgtgaac caggtcgcgc 5040
tgcgggccgc gcgcgaacac cgccacgtcc tcgcctgcgt gggtctcttc gtccaggggc 5100
actgctgact gctgccgata tcggggctc ccgctctcgc tctcggtaac atccggccgg 5160
gcgccgtcct tgagcacata gcctggaccg ttttccgtata ggaggaccgt gtaggccttc 5220
ctgtcccggg ccttgccagg ggccagcccg aagatggagc tccctcgcag ggggtagcct 5280
ccgaaggaga agacgtggga gtggtcggca gtgacgaggc tcagcgtgtc ctcctcgctg 5340
gtgagctggc ccgccctctc aatggcgtcg tcgaacatga tcgtctcagt cagtgcccgg 5400
taagccctgc ttcatgatg accatggtc atgcgaccac cctccacgaa gaggaagaag 5460
ccgcggggt tcctgctcag caggcgcagg gcagcctctg tcatctccat caggggaggg 5520
tccagtgtgg agtctcggtg gatctcgtat ttcatgtctc caggctcaaa gagacccatg 5580
agatgggtca cagacgggtc cagggaagcc tgcatgagct cagtgcggtt ccacacatac 5640
cgggcaccct ggcgcttcgc cagccattcc tgcaccagat tcttcccgtc cagcctggtc 5700
ccaccttggc tgtagtcatc tgggtactca gggtctgggg ttcccatgcg aaacatgtac 5760
tttcggcctc cacctaggat cacgtcaatg tccatgttgg agatgagctg cgtagcgatg 5820
tcctggcacc cctcctggcg ggccaggca ggcacgtcgg cgtccgagta ccagttgcgg 5880
ttcaccgtgt gggcgtaggt gccggctggc gaggcgtgct gcactcgtgt ggtggttacc 5940
actcccactg acttcctgc tttcttggcc cgattcatca cggagatgac ctcgttgccg 6000
cgtgtcgtgt tgcactggtt aaagcggcg gctgcactca agcaatggt ctggaagttg 6060
cccttgaccc cgcacaggta ggccgtggct gtggctccac tgtctggcac atgtttgtct 6120
acattgtatg tcttggacag agccacatat gggaagcggt ccatgccagg gggtatctca 6180
ggcccagtt tgtccttctt ctgccctttt aggatcctgg cagtagcacc cgtagacacc 6240
cccatcccat cgcccaggaa gatgatgagg ttcttggcgg ctgtctgtgc aggctgcagc 6300
ttcttggcgg cacccagggc ctcggctgcc tcgcggttcc agaagtccgg gttctcctcc 6360
tcaactggga tgatgcccag ggagagctgt agcctcaggc ccagcagcag cagcagcagc 6420
agcatggtgg atgcggccgc tctagacacg acacctgaaa tggaaggaaa aactttgaa 6480
ccactgctctg aggcttgaga atgaaccaag atccaaactc aaaaagggca aattccaagg 6540
agaattacat caagtgccaa gctggcctaa cttcagtctc cacccactca gtgtggggaa 6600
actccatcgc ataaaacccc tcccccaac ctaaagacga cgtactccaa aagctcgaga 6660
actaatcgag gtgcctggac ggcgcccggt actccgtgga gtcacatgaa gcgacggctg 6720
aggacggaaa ggccctttc ctttgtgtgg gtgactcacc cgcccgctct cccgagcgcc 6780
gcgtcctcca ttttgagctc cctgcagcag ggccggggag gcatctt tccgctcacg 6840
caactggtgc cgaccgggcc agccttgccg cccaggggcgg ggcgatacac ggcggcgcga 6900
ggccaggcac cagagcaggc cggcagcttc gagactaccc ccgtcgatt tcggtggcc 6960
gcgctcgcag gccccgcctc gccgaacatg tgcgctggga cgcacgggcc ccgtcgccgc 7020
ccgcggcccc aaaaacgaa ataccagtgt gcagatcttg gcccgcattt acaagactat 7080
cttgccagaa aaaagcgtc gcagcaggtc atcaaaaatt ttaaatggct agagacttat 7140
```

-continued

```
cgaaagcagc gagacaggcg cgaaggtgcc accagattcg cacgcggcgg ccccagcgcc   7200
caagccaggc ctcaactcaa gcacgaggcg aaggggctcc ttaagcgcaa ggcctcgaac   7260
tctcccaccc acttccaacc cgaagctcgg gatcaagaat cacgtactgc agccagggc   7320
gtggaagtaa ttcaaggcac gcaagggcca taacccgtaa agaggccagg cccgcgggaa   7380
ccacacacgg cacttacctg tgttctggcg tctagagtcg actagctttt aagcgggtcg   7440
ctgcagggtc gctcggtgtt cgaggccaca cgcgtcacct taatatgcga agtggacctg   7500
ggaccgcgcc gccccgactg catctgcgtg ttcgaattcg ccaatgacaa gacgctgggc   7560
ggggtttgtg tcatcataga actaaagaca tgcaaatata tttcttccgg ggacaccgcc   7620
agcaaacgcg agcaacgggc cacggggatg aagcagctgc gccactccct gaagctcctg   7680
cagtccctcg cgcctccggg tgacaagata gtgtacctgt gccccgtcct ggtgtttgtc   7740
gcccaacgga cgctccgcgt cagccgcgtg acccggctcg tcccgcagaa ggtctccggt   7800
aatatcaccg cagtcgtgcg gatgctccag agcctgtcca cgtatacggt ccccatggag   7860
cctaggaccc agcgagcccg tcgccgccgc ggcggcgccg cccgggggtc tgcgagcaga   7920
ccgaaaaggt cacactctgg ggcgcggac cgccccgagt cagccgcccg ccagttacca   7980
cccgccgacc aaaccccccgc ctccacgag ggcggggggg tgcttaagag gatcgcggcg   8040
ctcttctgcg tgcccgtggc caccaagacc aaaccccgag ccgcctccga atgagagtgt   8100
ttcgttcctt ccccctcccc ccgcgtcaga caaaccctaa ccaccgctta agcggccccc   8160
gcgaggtccg aagactcatt tagatctaag ctattctcag ctgccatgaa aaatcgatac   8220
cgtcttcgct agaactaggg tcgatcgact ctagtatgat gcactctcag tacaatctgc   8280
tctgatgccg catagttaag ccagtatctg ctccctgctt gtgtgttgga ggtcgctgag   8340
tagtgcgcga gcaaaattta agctacaaca aggcaaggct tgaccgacaa ttgcatgaag   8400
aatctgctta gggttaggcg ttttgcgctg cttcgcgatg tacgggccag atatacgtgg   8460
atctgagggg actagggtgt gtttaggcga aaagcggggc ttcggttgta cgcggttagg   8520
agtccctca ggatatagta gtttcgcttt tgcatagga ggggggaaatg tagtcttatg   8580
caatactctt gtagtcttgc aacatggtaa cgatgagtta gcaacatgcc ttacaaggag   8640
agaaaaagca ccgtgcatgc cgattggtgg aagtaaggtg gtacgatcgt gccttattag   8700
gaaggcaaca gacgggtctg acatggattg gacgaaccac tgaattccgc attgcagaga   8760
tattgtattt aagtggcctag ctcgatacaa taaacgccat ttgaccattc accacattgg   8820
tgtgcacctc caagctggta gaggatcggt cgatcgactc tagacaggta agtggcgttt   8880
ctcggggagc cagctgcgtc cgctgtcgtg ctgtcggtgt agtactagca agcgttaagt   8940
ccccatctgg ctgcggccta ccgaagagtg tcttcacgt cacacgctgt cccacgcacg   9000
tggttggttt ggtcgcttct ggttactgac tactaagcag cctttctttt tttcctttca   9060
ggttctagag cggccgccac cgaaacgccg tacgccacca tggagtggtc ttgggtgttc   9120
ctgttctttc tgtccgtgac cacaggccgtc cacagccagt cggtggagga gtccggggga   9180
ggcctggtca agcctgaggg atccctgaca ctcacctgca gcctctggg attctccttc   9240
agttccaact actggatatg ctgggtccga caggctccgg ggaagggct ggagtggatc   9300
gcatgcattt atgctggtag tgatagtacc actgactacg cgagctgggc gaaaggccga   9360
ttccaccatct ccaaaacctc gtcgaccacg gtgactctgc aaatgaccag tctgacagcc   9420
gcggacacgg ccacctattt ctgtgcgaga ggtactgctga ctagtctgca ctacttttaac   9480
ttgtggggcc caggcaccct ggtcaccatc tcttcagctg gaggaggcgg tagtggtggt   9540
ggtggatctg gtggtggtgg atccgccgat ctgacccaga ctccagcctc gatgtctgca   9600
gctgtgggag gcacagtcac catcaactgc caggccagtc agagtgttag tagtaacaac   9660
cgcttagcct ggtatcagca gaaaccaggg cagcctccca agctcctat ctacagggca   9720
tccactctgg catctggggt cccatcgcgg ttcaaaggca gtggatctgg gacacagttc   9780
actctcacca tcagcgacct ggagtgtgcc gatgctgcca cttactactg tcagagctat   9840
tattggggta gtagtaatag ttataattcc tgggcttcg gcggagggac cgaggtggtc   9900
gtcaaaggtg ctgacaagac ccacacctgt ccccccttgc ctgctcctga gctgctggga  9960
ggccctagcg tgttcctgtt tccccctaag cccaaggaca ccctgatgat ctccaggacc  10020
cccgaagtga cctgcgtggt ggtggatgtg agccacgagg accctgaggt gaagttcaac  10080
tggtacgtgg acggcgtgga ggtccacaac gccaagacaa acccagggga ggagcagtac  10140
aacagcacat atcgggtggt gagcgtgctg accgtgctgc accaggactg gctgaacggc  10200
aaggagtaca agtgcaaggt gtccaacaag gccctccccg ccccattga gaagaccatc  10260
tccaaggcca agggccagcc tagggagccc caggtgtaca cactgcctcc cagcagggac  10320
gagctgacca gaaccaggt gagcctgacc tgcctggtga agggcttcta ccctccgat  10380
atcgccgtgg agtgggagtc caatggccag cccgaaaaca actacaagac caccccccct  10440
gtgctggact ccgatggcag cttcttcctc tactccaagc tgaccgtgga caagtcccgg  10500
tggcagcagg gcaacgtgtt cagctgttcc gtgatgcacg aggccctgca caaccattac  10560
acccagaagt ccctgagcct gtcccccgga aaatgatggg gcgcgccgct tcgaagcgac  10620
ttttgtcccg aattcctgca gcccctagct agtctttccg atcgatggaa ggatccgtcg  10680
gagctctacc ttgcggccgc gacatgataa gatacattga tgagtttgga caaaccacaa  10740
ctagaatgca gtgaaaaaaa tgctttattt gtgaaatttg tgatgctatt gctttatttg  10800
tgaaatttgt gatgctattg ctttatttgt aaccattata agctgcaata aacaagttaa  10860
caacaacaat tgcattcatt ttatgtttca ggttcagggg gaggtgtggg aggttttta  10920
aagcaagtaa aacctctaca aatgtggtag atcatttgac ccg                    10963
```

SEQ ID NO: 4         moltype = DNA   length = 6679
FEATURE              Location/Qualifiers
source               1..6679
                     mol_type = other DNA
                     organism = synthetic construct
SEQUENCE: 4

```
agcttgcatg cctgcaggtc gccagtcctg ttttgacaag ttgcctctgg aagcctctac     60
aatgcctctc ttcttttttct ccagagtaag cggaggccag gggcccccgg cctctgctta    120
atactaaaaa aaacagctgt tgtcatagta atgattgggt ggaaacattc taggcagatc    180
tagtcgggag gaaaattact gtgttggagg ccctccgcca tcttctgaag ctgatccccg    240
ggggatccac tagtcgggta tcatatgctg actgtatacg catgaggata gcatatgcta    300
cccggataca gattaggata gcatatacta cccagatata gattaggata gcatatgcta    360
cccagatata gattaggata gcctatgcta cccagatata aattaggata gcatatacta    420
cccagatata gattaggata gcatatgcta cccagatata gattaggata gcctatgcta    480
```

```
cccagatata gattaggata gcatatgcta cccagatata gattaggata gcatatgcta  540
tccagatatt tgggtagtat atgctaccca gatataaatt aggatagcat atactaccct  600
aatctctatt aggatagcat atgctacccg gatacagatt aggatagcat atactaccca  660
gatatagatt aggatagcat atgctaccca gatatagatt aggatagcct atgctaccca  720
gatataaatt aggatagcat atactaccca gatatagatt aggatagcat atgctacccg  780
gatatagatt aggatagcct atgctaccca gatatagatt aggatagcat atgctatcca  840
gatatttggg tagtatatgc tacccatggc aacattagac tagttctagc gaagacggta  900
tcgatttttcc atggcagctg agaatagctt agatctaaat gagtcttcgg acctcgcggg  960
ggccgcttaa gcggtggtta gggtttgtct gacgcggggg gaggggggaag gaacgaaaca 1020
ctctcattcg gaggcggctc ggggtttggt cttggtggcc acgggcacgc agaagagcgc 1080
cgcgatcctc ttaagcaccc cccgccctc cgtggaggcg ggggtttggt cggcgggtgg 1140
taactggcgg gccgctgact cgggcgggtc gcgcgcccca gagtgtgacc ttttcggtct 1200
gctcgcagac ccccggcggc gccgccgcg gcggcgacgg gctcgctggg tcctaggctc 1260
catggggacc gtatacgtgg acaggctctg gagcatccgc aagactgcgg tgatattacc 1320
ggagaccttc tgcgggacga gccgggtcac gcggctgacg cggagcgtcc gttgggcgac 1380
aaacaccagg acgggcaca ggtacactat cttgtcaccc ggaggcgcga gggactgcag 1440
gagcttcagg gagtggcgca gctgcttcat ccccgtggcc cgttgctcgc gtttgctggc 1500
ggtgtccccg gaagaaatat atttgcatgt ctttagttct atgatgacac aaaccccgcc 1560
cagcgtcttg tcattggcga attcgaacac gcagatgcag tcggggcggc gcggtcccag 1620
gtccacttcg catattaagg tgacgcgtgt ggcctcgaac accgagcgac cctgcagcga 1680
cccgcttaaa agctagcgta tacgatcga tcctgcaggt cgactctaga cgccagaaca 1740
caggtaagtg ccgtgtgtgg ttcccgcggg cctggcctct ttacgggtta tggcccttgc 1800
gtgccttgaa ttacttccac gcccctggct gcagtacgtg attcttgatc ccgagcttcg 1860
ggttggaagt gggtgggaga gttcgaggcc ttgcgcttaa ggagccccctt cgcctcgtgc 1920
ttgagttgag gcctggcttg ggcgctgggg ccgccgcgtg cgaatctggt ggcaccttcg 1980
cgcctgctctc gctgctttcg ataagtctct agccatttaa aattttttgat gacctgctcg 2040
gacgcttttt ttctggcaag atagtcttgt aaatgcgggc caagatctgc acactggtat 2100
ttcggttttt ggggccgcgg gcggcgacgg ggcccgtgcg tcccagcgca catgttcggc 2160
gaggcgggggc ctgcgagcgc ggccaccgag aatcggacgg gggtagtctc aagctggccg 2220
gcctgctctg gtgcctggcc tcgcgccgcc gtgtatcgcc ccgcccctgg cggcaaggct 2280
ggcccggtcg gcaccagttg cgtgagcgga aagatggccg cttcccggcc ctgctgcagg 2340
gagctcaaaa tggaggacgc ggcgctcggg agagcgggcg ggtgagtcac ccacacaaag 2400
gaaaagggcc tttccgtcct cagccgtcgc ttcatgtgac tccacggagt accgggcgcc 2460
gtccaggcac ctcgattagt tctcgagctt ttggagtacg tcgtctttag gttgggggga 2520
ggggttttat gcgatggagt ttccccacac tgagtgggtg gagactgaag ttaggccgag 2580
ttggcacttg atgtaattct ccttggaatt tgccctttt gagtttggat cttggttcat 2640
tctcaagcct cagacagtgg ttcaaagttt tttccttcca tttcaggtgt cgtgtctaga 2700
gcggccgcca ccgaaacgcc gtacggcgcg atcgccgct agcgcattta aatcctgtac 2760
agccggtccg ggggcgcgcc gcttcgaagc gacttctaga ggatctaaga ggatggagac 2820
agcatgcgaa cgtttacatg tagcgcaaga aacacaaatg cagttgattg agaaaagtag 2880
tgataagttc caagatcata tactgtactg gactgctgtt agaactgaga acacactgct 2940
ttatgctgca aggaaaaaag gggtgactgt cctaggacac tgcagagtac cacactctgt 3000
agtttgtcaa gagagagcca agcaggccat tgaaatgcat tgttcttttgc aggagttaag 3060
caaaactgag tttggggatg aaccatggtc tttgcttgac acaagctggg accgatatat 3120
gtcagaacct aaacggtgct ttaagaaagg cgccagggtg gtagaggtgg agtttgatgg 3180
aaatgcaagc aatacaaact ggtacactgt ctacagcaat ttgtacatgc gcacagagga 3240
cggctgcgcag cttgcgaagg ctggggctga cggaactggg ctctactact gcaccatcgc 3300
cggtgctgga cgcatttact attctcgctt tggtgacgag gcagccagat ttagtacaac 3360
agggcattac tctgtaagag atcaggacag agtgtatgct ggtgtctcat ccacctcttc 3420
tgatttttaga gatcgcccag acggagtctg ggtcgcatcc gaaggacctg aaggagaccc 3480
tgcaggaaaaa gaagccgagc cagcccagcc tgtctcttct ttgctcggct cccccgcctg 3540
cggtcccatc agagcaggcc tcggttgggt acgggacggt cctcgctcgc acccctacaa 3600
ttttcctgca ggctcggggg gctctattct ccgtcttcc tccacccgg tgcagggcac 3660
ggtaccggtg gacttggcat caaggcagga agaagaggag cagtcgcccg actccacaga 3720
ggaagaacca gtgactctcc caaggcgcac caccaatgat ggattccacc tgttaaaggc 3780
aggagggtca tgcttttgctc taatttcagg aactgctaac caggtaaagt gctatcgctt 3840
tcgggtgaaa agaaccata gacatcgcta cgagaactgc accaccacct ggttcacagt 3900
tgctgacaac ggtgctgaaa gacaaggaca agcacaaata ctgatcacct ttggatcgcc 3960
aagtcaaagg caagactttc tgaaacatgt accactacct cctggaatga acatttccgg 4020
ctttacagcc agcttggact tctgatcact gccattgcct tttcttcatc tgactggtat 4080
actatgccaa atctatggtt tctattgttc tgggactag ttgtcccgaa ttcctgcagc 4140
ccctagctag tctttccgat cgatggaagg atccgtcgga gctctaccctt gcggccgcga 4200
catgataaga tacattgatg agttggaca aaccacaact agaatgcagt gaaaaaatg 4260
cttatttgt gaaattgtg atgctattgc tttattgta aatttgtga tgctattgct 4320
ttatttgtaa ccattataag ctgcaataaa caagttaaca acaacaattg cattcatttt 4380
atgtttcagg ttcagggga ggtgtgggag gtttttaaa gcaagtaaaa cctctacaaa 4440
tgtggtagat catttaaatg ttaattgtac tagcttgcca aacctacagg tggggtcttt 4500
cattcccccc ttttttctgga gactaaataa aatctttat tttatcgatg cgttgctggc 4560
gtttttccat aggctccgcc ccctgacga gcatcaaaa aatcgacgct caagtcagag 4620
gtggcgaaac ccgacaggac tataaagata ccaggcgttt ccccctggaa gctccctcgt 4680
gcgctctcct gttccgaccc tgccgcttac cggatacctg tccgcctttc tcccttcggg 4740
aagcgtggcg ctttctcata gctcacgctg taggtatctc agttcggtgt aggtcgttcg 4800
ctccaagctg ggctgtgtgc acgaaccccc gttcagccc gaccgctgcg ccttatccgg 4860
taactatcgt cttgagtcca acccggtaag acacgactta tcgccactgg cagcagccac 4920
tggtaacagg attagcagag cgaggtatgt aggcggtgct acagagttct tgaagtggtg 4980
gcctaactac ggctacacta agaacagt ttttggtatc tgcgctctgc tgaagccagt 5040
taccttcgga aaaagagttg gtagctcttg atccggcaaa caaaccaccg ctggtagcgg 5100
tggttttttt gtttgcaagc agcagattac gcgtaaccac cacacccgcc gcatcgatgc 5160
atcgatgcga acccagagt cccgctcaga agaactcgtc aagaaggcga tagaaggcga 5220
```

-continued

```
tgcgctgcga atcgggagcg gcgataccgt aaagcacgag gaagcggtca gcccattcgc 5280
cgccaagctc ttcagcaata tcacgggtag ccaacgctat gtcctgatag cggtccgcca 5340
cacccagccg gccacagtcg atgaatccag aaaagcggcc attttccacc atgatattcg 5400
gcaagcaggc atcgccatgg gtcacgacga gatcctcgcc gtcgggcatg cgcgccttga 5460
gcctggcgaa cagttcggct ggcgcgagcc cctgatgctc ttcgtccaga tcatcctgat 5520
cgacaagacc ggcttccatc cgagtacgtg ctcgctcgat gcgatgtttc gcttggtggt 5580
cgaatgggca ggtagccgga tcaagcgtat gcagccgccg cattgcatca gccatgatgg 5640
atactttctc ggcaggagca aggtgagatg acaggagatc ctgccccggc acttcgccca 5700
atagcagcca gtcccttccc gcttcagtga caacgctgcg cacagctgcg caaggaacgc 5760
ccgtcgtggc cagccacgat agccgcgctg cctcgtcctg cagttcattc agggcaccag 5820
acaggtcggt cttgacaaaa agaaccgggc gccctgcgc tgacagccgg aacacgcgcg 5880
catcagagca gccgattgtc tgttgtgccc agtcatagcc gaatagcctc tccacccaag 5940
cggccggaga acctgcgtgc aatccatctt gttcaatcat gcgaaacgat cctcatcctg 6000
tctcttgatc agatcttgat ccctgcgcc atcagatcct tggcggcaga aaagccatcc 6060
agtttacttt gcagggcttc ccaacccttac cagagggcgc cccagctggc aattccggtt 6120
cgcttgctgt ccataaaacc gcccagtcta gctatcgcca tgtaagccca ctgcaagcta 6180
cctgctttct ctttgcgctt gcgttttccc ttgtccagat agcccagtag ctgacattca 6240
tccggggtca gcaccgtttc tgcggactgg cttctacgt gttccgcttc ctttagcagt 6300
ccttgcgccc tgagtgcttg cggcagcgtg aagcttttt caaaagccta ggcctccaaa 6360
aaagcctcct cactacttct ggaatagctc agaggccgag gcggcctcgg cctctgcata 6420
aataaaaaaa attagtcagc catggggcgg agaatgggcg gaactgggcg gagttagggg 6480
cgggatgggc ggagttaggg gcgggactgg ggttgctgac taattgagat gcatgctttg 6540
catacttctg cctgctgggg agcctgggga cttttccacac ctggttgctg actaattgag 6600
atgcatgctt tgcatacttc tgcctgctgg ggagcctggg gactttccac accctaactg 6660
acacacattc cacagggtc                                              6679

SEQ ID NO: 5          moltype = DNA  length = 34
FEATURE               Location/Qualifiers
source                1..34
                      mol_type = other DNA
                      organism = synthetic construct
SEQUENCE: 5
ataacttcgt ataatgtatg ctatacgaag ttat                              34

SEQ ID NO: 6          moltype = DNA  length = 34
FEATURE               Location/Qualifiers
source                1..34
                      mol_type = other DNA
                      organism = synthetic construct
SEQUENCE: 6
ataacttcgt ataaagtatc ctatacgaag ttat                              34

SEQ ID NO: 7          moltype = DNA  length = 48
FEATURE               Location/Qualifiers
source                1..48
                      mol_type = other DNA
                      organism = synthetic construct
SEQUENCE: 7
gaagttccta ttccgaagtt cctattctct agaaagtata ggaacttc               48

SEQ ID NO: 8          moltype = DNA  length = 48
FEATURE               Location/Qualifiers
source                1..48
                      mol_type = other DNA
                      organism = synthetic construct
SEQUENCE: 8
gaagttccta ttccgaagtt cctattcttc aaaaagtata ggaacttc               48

SEQ ID NO: 9          moltype = DNA  length = 48
FEATURE               Location/Qualifiers
source                1..48
                      mol_type = other DNA
                      organism = synthetic construct
SEQUENCE: 9
ggtttgtctg gtcaaccacc gcggtctcag tggtgtacgg tacaaacc               48

SEQ ID NO: 10         moltype = DNA  length = 38
FEATURE               Location/Qualifiers
source                1..38
                      mol_type = other DNA
                      organism = synthetic construct
SEQUENCE: 10
ggcttgtcga cgacggcggt ctccgtcgtc aggatcat                          38

SEQ ID NO: 11         moltype = DNA  length = 1497
FEATURE               Location/Qualifiers
source                1..1497
                      mol_type = other DNA
                      organism = synthetic construct
```

```
SEQUENCE: 11
atggagtggt cttgggtgtt cctgttcttt ctgtccgtga ccacaggcgt ccacagccag    60
tcggtggagg agtccggggg aggcctggtc aagcctgagg gatccctgac actcacctgc   120
acagcctctg gattctcctt cagttccaac tactggatat gctgggtccg ccaggctccg   180
gggaagggc tggagtggat cgcatgcatt tatgctgcta gtgatagtac cactgactac   240
gcgagctggg cgaaaggccg attcaccatc tccaaaacct cgtcgaccac ggtgactctg   300
caaatgacca gtctgacagc cgcggacacg gccacctatt tctgtgcgag aggtactgat   360
cgtagtgctg actactttaa cttgtggggc ccaggcaccc tggtcaccat ctcttcagct   420
ggaggaggcg gtagtggtgg tggtggatct ggtggtggtg gatccgccga tctgacccag   480
actccagcct cgatgtctgc agctgtggga ggcacagtca ccatcaactg ccaggccagt   540
cagagtgtta gtagtaacaa ccgcttagcc tggtatcagc agaaaccagg gcagcctccc   600
aagctcctta tctacaggc atccactctg gcatctgggg tcccatcgcg gttcaaaggc   660
agtggatctg ggacacagtt cactctcacc atcagcgacc tggagtgtgc cgatgctgcc   720
acttactact gtcagagcta ttattgggt agtagtaata gttataattc ctgggcttc   780
ggcggaggga ccgaggtggt cgtcaaaggt gctgacaaga cccacacctg tccccttgc   840
cctgctcctg agctgctggg aggccctagc gtgttcctgt tcccccctaa gcccaaggac   900
accctgatga tctccaggac ccccgaagtg acctgcgtgg tggtggatgt gagccacgag   960
gaccctgagg tgaagttcaa ctggtacgtg gacggcgtgg aggtgcacaa cgccaagaca  1020
aaacccaggg aggagcagta caacagcaca tatcgggtgg tgagcgtgct gaccgtgctg  1080
caccaggact ggctgaacgg caaggagtac aagtgcaagg tgtccaacaa ggcccctccc  1140
gcccccattg agaagaccat ctccaaggcc aagggccagc ctagggagcc ccaggtgtac  1200
acactgcctc ccagcaggga cgagctgacc aagaaccagg tgagcctgac ctgcctggtg  1260
aagggcttct accctccga tatcgccgtg gagtgggagt ccaatggcca gcccgaaaac  1320
aactacaaga ccacccccc tgtgctggac tccgatggca gcttcttcct ctactccaag  1380
ctgaccgtgg acaagtcccg gtggcagcag ggcaacgtgt cagctgttc cgtgatgcac  1440
gaggccctgc acaaccatta cacccagaag tccctgagcc tgtccccgg aaaatga    1497

SEQ ID NO: 12           moltype = DNA  length = 3075
FEATURE                 Location/Qualifiers
source                  1..3075
                        mol_type = other DNA
                        organism = synthetic construct
SEQUENCE: 12
atgggcgtga aggtgctgtt cgccctgatc tgtatcgccg tggccgaggc caagcccacc   60
gagaacaatg aggacttcaa catcgtggcc gtgccagca acttcgccac cacagacctg   120
gatgccgaca gaggcaagct gcccggcaag aaactgcccc tggaagtgct gaaagagatg   180
gaagccaatg ccagaaaggc cggctgcacc agaggctgcc tgatctgcct gagccacatc   240
aagtgcaccc ccaagatgaa gaagttcatc ccggcagat gccacaccta tgagggcgac   300
aaagagtctg cccagggcgg catcgcgag gccatcgtga acatcccga gatccccggc   360
ttcaaggacc tggaacccat ggaacagttt atcgcccagg tggacctgtg cgtggactgc   420
accaccggct gtctgaaggg cctgccaac gtgcagtgca gcgacctgct gaagaagtgg   480
ctgcccaga gatgcgccac cttcgccagc aagatccagg ccaggtgga caagatcaag   540
ggggctgcg gcgacgcacc ggtgaaacag actttgaatt ttgaccttct caagttgcg   600
ggagacgtgg agtccaaccc tgggcccttc gaaatggtga gcaagggcga ggagctgttc   660
accggggtg tgcccatcct ggtcgagctg gacggcgacg taaacggcca aagttcagc   720
gtgtccggcg agggcgaggg cgatgccacc tacggcaagc tgaccctgaa gttcatctgc   780
accaccggca agctgcccgt gccctggccc accctcgtga ccacccctga ctacggcgtg   840
cagtgcttca gccgctaccc cgaccacatg aagcagcacg acttcttcaa gtccgccatg   900
cccgaaggct acgtccagga gcgcaccatc ttcttcaagg acgacggcaa ctacaagacc   960
cgcgccgagg tgaagttcga gggcgacacc ctggtgaacc gcatcgagct gaagggcatc  1020
gacttcaagg aggacggcaa catcctgggg cacaagctgg agtacaacta caacagccac  1080
aacgtctata tcatgccga caagcagaag aacggcatca aggtgaactt caagatccgc  1140
cacaacatcg aggacggcag cgtgcagctc gccgaccact accagcagaa cacccccatc  1200
ggcgacggcc ccgtgctgct gcccgacaac cactacctga gcacccagtc cgccctgagc  1260
aaagacccca acgagaagcg cgatcacatg gtcctgctgg agttcgtgac cgccgccggg  1320
atcactctcg gcatggacga gctgtacaag gcaccggtga aacagacttt gaattttgac  1380
cttctcaagt tggcgggaga cgtggagtcc aaccctgggc ccatggaaga tgccaaaaac  1440
attaagaaag gcccagcgcc attctaccca ctcgaagacg gaccgccgg cgagcagctg  1500
cacaaagcca tgaagcgcta cgcccctggtg cccggcacca tcgcctttac cgacgcacat  1560
atcgaggtgg acattaccta cgccagcgac ttcgagatga gcgttcggct ggcagaagct  1620
atgaagcgct atgggctgaa tacaaaccat cggatcgtgg tgtgcagcga aatagcttg  1680
cagttcttca tgcccgtgtt gggtgccctg ttcatcggtg tggctgtggc cccagctaac  1740
gacatctaca cgagcgcga gctgctgaac agcatgggca tcagccagcc caccgtcgta  1800
ttcgtgagca agaaagggct gcaaaagatc ctcaacgtgc aaaagaagct accgatcata  1860
caaaagatca tcatcatgga tagcaagacc gactaccagg cttccaaag catgtacacc  1920
ttcgtgactt cccatttgcc accggctta acgagtacg acttcgtgcc cgagagcttc  1980
gacccgggaca aaaccatcgc cctgatcatg aacagtagtg gcagtaccgg attgccaag  2040
ggcgtagccc taccgcaccg caccgcttgt gtccgattca gtcatgccct cgaccccatc  2100
tccggcaacc agatcatccc cgacaccgct atcctcagcg tggtgccatt tcaccacgc  2160
ttcggcatgt tcaccacgct gggctacttg atctgcggct ttcgggtcgt gctcatgtac  2220
cgcttcgagg aggagctatt ttcgcgcagc ttgcaagact ataagattca atctgccctg  2280
ctggtgccca cactatttgg cttcttcgct aagagcactc tcatcgacaa gtacgaccta  2340
agcaacttgc acgagatcgc cagcggcggg gcgccgctca gcaaggaggt aggtgaggcc  2400
gtggccaaac gcttccacct accaggcatc cgcagggct gacagaacaacc  2460
agcgccattc tgatcacccc cgaaggggac gacaagcctg gcgcagtagg caaggtggtg  2520
cccttcttcg aggctaaggt ggtggacttg gacaccggta agacactggg tgtgaaccag  2580
cgcggcgagc tgtgcgtccg tggcccatg atcatgagcg gctacgttaa caaccccgag  2640
gctacaaacg ctctctatcga caaggacggc tggctgcaca gcggcgacat cgcctactgg  2700
gacgaggacg agcacttctt catcgtggac cggctgaaga gcctgatcaa atacaaaggc  2760
```

```
taccaggtag ccccagccga actggagagc atcctgctgc aacacccaa catcttcgac    2820
gccggggtcg ccggcctgcc cgacgacgat gccggcgagc tgcccgccgc agtcgtcgtg    2880
ctggaacacg gtaaaaccat gaccgagaag gagatcgtgg actatgtggc cagccaggtt    2940
acaaccgcca agaagctgcg cggtggtgtt gtgttcgtgg acgaggtgcc taaaggactg    3000
accggcaagt tggacgcccg caagatccgc gagattctca ttaaggccaa gaagggcggc    3060
aagatcgccg tgtga                                                    3075

SEQ ID NO: 13           moltype = DNA  length = 2664
FEATURE                 Location/Qualifiers
source                  1..2664
                        mol_type = other DNA
                        organism = synthetic construct
SEQUENCE: 13
atgctgctgc tgctgctgct gctgggcctg aggctacagc tctccctggg catcatccca      60
gttgaggagg agaacccgga cttctggaac cgcgaggcag ccgaggccct gggtgccgcc     120
aagaagctgc agcctgcaca gacagccgcc aagaacctca tcatcttcct gggcgatggg     180
atgggggtgt ctacggtgac agctgccagg atcctaaaag gcagaagaa ggacaaactg      240
gggcctgaga taccccatgg catggaccgc ttcccatatg tggctctgtc caagacatac     300
aatgtagaca acacatgtgc agacagtgga gccacagcca cggcctacct gtgcggggtc     360
aagggcaact tccagaccat tggcttgagt gcagccgccc gctttaacca gtgcaacacg     420
acacgcggca acgaggtcat ctccgtgatg aatcgggcca agaaagcagg gaagtcagtg     480
ggagtggtaa ccaccacacg agtgcagcac ccctcgccag ccggcaccta cgcccacacg     540
gtgaaccgca actggtactc ggacgccgac gtgcctgcct cggcccgcca ggaggggtgc     600
caggacatcg ctacgcagct catctccaac atggacattg acgtgatcct aggtggaggc     660
cgaaagtaca tgtttcgcat gggaaccccca gaccctgagt acccagatga ctacagccaa     720
ggtggaacca ggctggacgg gaagaatctg gtgcaggaat gctggcgaa gcctgcaggggt    780
gcccggtatg tgtggaaccg cactgagctc atgcaggctt ccctggaccc gtctgtgacc     840
catctcatgg gtctctttga gcctggagac atgaaatacg agatccaccg agactccaca     900
ctggaccccct ccctgatgga gatgacagag gctgccctgc gctgctgag caggaaccccc    960
cgcggcttct tcctcttcgt ggagggtggt cgcatcgacc atggtcatca tgaaagcagg    1020
gcttaccggg cactgactga gacgatcatg ttcgacgacg ccattgagag ggcgggccag    1080
ctcaccagcg aggaggacac gctgagcctc gtcactgccg accactccca cgtcttctcc    1140
ttcggaggct acccccctgcg agggagctcc atcttcgggc tggcccctgg caaggcccgg    1200
gacaggaagg cctacacggt cctcctatac ggaaacggtc caggctatgt gctcaaggac    1260
gcgcccggc cggatgttac cgagagcgag agcgggagcc ccgagtatcg gcagcagtca    1320
gcagtgcccc tggacgaaga gacccacgca ggcgaggacg tggcggtgtt cgcgcgcggc    1380
ccgcaggcgc acctggttca cggcgtgcag gagcagacct tcatagcgca cgtcatggcc    1440
ttcgccgcct gcctggagcc ctacaccgcc tgcgacctgg cgccccccgc cggcaccacc    1500
gacgccgcca acccggtta ctctagagtc ggggcgacg gccgcttcga cagacacga     1560
ccggtgaaac agactttgaa ttttgacctt ctcaagttgg cgggagacgt ggagtccaac    1620
cctgggccca aaagctga actcaccgcg acgtctgtcg agaagtttct gatcgaaaag    1680
ttcgacagcg tctccgacct gatgcagctc tcggagggcg aagaatctcg tgctttcagc    1740
ttcgatgtag gagggcgtgg atatgtcctg cgggtaaata gctgcgcga tggtttctac    1800
aaagatcgtt atgtttatcg gcactttgca tcggccgcgc tcccgattcc ggaagtgctt    1860
gacattgggg aattcagcga gagcctgacc tattgcatct cccgccgtgc acagggtgtc    1920
acgttgcaag acctgcctga aaccgaactg cccgctgttc tgcagccggt cgcggaggcc    1980
atggatgcga tcgctgcggc cgatcttagc cagacgaggg ggttcggcga attcggaccg    2040
caaggaatcg gtcaatacac tacatggcgt gatttcatat gcgcgattgc tgatccccat    2100
gtgtatcact ggcaaactgt gatggacgac accgtcagtg cgtccgtcgc gcaggctctc    2160
gatgagctga tgctttgggc cgaggactgc cccgaagtcc ggcacctcgt gcacgcggat    2220
ttcggctcca acaatgtcct gacggacaat ggccgcataa cagcggtcat tgactggagc    2280
gaggcgatgt cgggggattc ccaatacgag gtcgccaaca tcttcttctg gaggccgtgg    2340
ttggcttgta tggagcagca gacgcgctac ttcgagcgga gcatccggga cttgcaggga    2400
tcgccgcggc tccgggcgta tatgctccgc attggtcttg accaactcta tcagagcttg    2460
gttgacggca atttcgatga tgcagcttgg gcgcagggtc gatgcgacgc aatcgtccga    2520
tccggagccg ggactgtcgg gcgtacacaa atcgcccgca gaagcgcggc cgtctgaccc    2580
gatgctgtg tagaagtact cgccgatagt ggaaaccgac gccccagcac tcgtccggat    2640
cgggagatgg gggaggctaa ctga                                          2664

SEQ ID NO: 14           moltype = DNA  length = 7908
FEATURE                 Location/Qualifiers
source                  1..7908
                        mol_type = other DNA
                        organism = synthetic construct
SEQUENCE: 14
gacccagcga gcccgtcgcc gccgcggcgg cgccgcccgg gggtctgcga gcagaccgaa      60
aaggtcacac tctgggggcgc gcgacccgcc cgagtcagcg gcccgccagt taccaccgc     120
cgaccaaaacc cccgccctcca cggagggcgg ggggtgctt aagaggatcg cggcgctctt    180
ctgcgtgccc gtggccacca agaccaaacc ccgaccgcc tccgaatgga agtgtttcgt     240
tccttccccc tcccccgcg tcagacaaac cctaaccacc gcttaagcgg ccccccgag     300
gtccgaagac tcatttcgta ctcgtcgaca ccggaagcgg tcgccactct gaccggacac     360
ggttcagaca tagaccgcag gcggttcgta cccataccgt tgccggtgaa atgagttacc     420
gatcacggtg gcacgcctaa ccgccaacgg tgtgtctaaa gaccgcgtcc ggtagctgtc     480
cttaccgttg acggtgtcca gacagaccgc gaacggtgtt ttccaaacc gatagcggta    540
agcttgatat agctccggtg cccgtcagtg ggcagagcgc acatcgccca cagtcccga     600
gaagttgggg ggagggtcg gcaattgaac cggagcttga tgcgtctaga tgatttcctt     660
catccctggc acacgtccag gcagtgtcga atccatctct gctacagggg aaaacaaata     720
acatttgagt ccagtggaga ccgggagcag aagtaaaggg aagtgataac ccccagagcc     780
cggaagcctc tggaggctga gacctcgccc ccttgcgtg atagggccta cggagccaca     840
```

```
tgaccaaggc actgtcgcct ccgcacgtgt gagagtgcag ggccccaaga tggctgccag    900
gcctcgaggc ctgactcttc tatgtcactt ccgtaccggc gagaaaggcg ggccctccag    960
ccaatgaggc tgcggggcgg gccttcacct tgataggcac tcgagttatc caatggtgcc   1020
tgcgggccga agcgactagg aactaacgtc atgccgagtt gctgagcgcc ggcaggcggg   1080
gccgggccgg ccaaaccaat gcgatggcca gggcggagtc gggcgctcta taagttgtcg   1140
ataggcgggc actccgccct agtttctaag gaaccggtag atcgaattcc tgcagcccgg   1200
gggatccact agttctagac gccagaacac aggtaagtgc cgtgtgtggt tcccgcgggc   1260
ctggcctctt tacgggttat ggcccttgcg tgccttgaat tacttccacg ccctggctg    1320
cagtacgtga ttcttgatcc cgagcttcgg gttggaagtg ggtgggagag ttcgaggcct   1380
tgcgcttaag gagccccttc gcctcgtgct tgagttgagg cctggcttgg gcgctggggc   1440
cgccgcgtgc gaatctggtg gcaccttcgc gcctgtctcg ctgctttcga taagtctcta   1500
gccatttaaa atttttgatg acctgctgcg acgctttttt tctggcaaga tagtcttgta   1560
aatgcgggcc aagatctgca cactggtatt tcggttttg gggccgcggg cggcgacggg    1620
gcccgtgcgt cccagccgca catgttcggcg aggcgggccc tgcgagcggg gccaccgaga   1680
atcggacggg ggtagtctca agctggccgg cctgctctgg tgcctggcct cgcgccgccg   1740
tgtatcgccc cgccctgggc ggcaaggctg gcccggtcgg caccagttgc gtgagcggaa   1800
agatggccgc ttcccggccc tgctgcaggg agctcaaaat ggaggacgcg gcgctcggga   1860
gagcgggcgg gtgagtcacc cacacaaagg aaaagggcct ttccgtcctc agccgtcgct   1920
tcatgtgact ccacggagta ccgggcgccg tccaggcacc tcgattagtt ctcgagcttt   1980
tggagtacgt cgtctttagg ttgggggag ggtttttatg cgatggagtt tccccacact    2040
gagtgggtgg agactgaagt taggccagct tggcacttga tgtaattctc cttgaatttt   2100
gcccttttg agtttggatc ttggttcatt ctcaagcctc agacagtggt tcaaagtttt    2160
ttccttccat ttcaggtgtc gtgtctagag cggccgccac cgaaacgccg tacgtcgcca   2220
ccatgaggct cgccgtggga gccctgctgg tctgcgccgt cctggggctg tgtctggctg   2280
tccctgataa aactgtgaga tggtgtgcag tgtcggagca tgaggccact aagtgccaga   2340
gtttccgcga ccatatgaaa agcgtcattc catccagtgt gcttgtgtga                2400
agaaagcctc ctaccttgat tgcatcaggg ccattgcggc aaacgaagcg gatgctgtga   2460
cactggatgc tggtttggtg tatgatgctt acctggctcc caataacctg aagcctgtgg   2520
tggcagagtt ctatgggtcc aaggaggacc cccagacctt ctactacgct gttgctgtgg   2580
tgaagaagga tagtggcttc cagatgaacc agcttcgagg caagaagtcc tgccacagga   2640
gtctaggccg ctccgctggg tggaacatcc cataggcctt actttactgt gacttacctg   2700
agccacgtaa acctcttgag aaagcagtgg ccaatttctt ctcgggcagc tgtgcccctt   2760
gtgcggatgg gacggacttc cccagctgt gtcaactgtg tccagggtgt ggctgctcca    2820
cccttaacca atacttcggc tactcgggag ccttcaagtg tctgaaggat ggtgctgggg   2880
atgtggcctt tgtcaagcac tcgactatat ttgagaactt ggcaaacaag gctgacaggg   2940
accagtgatga gctgctttgc ctggacaaca cccggaagcc ggtagatgaa tacaaggact   3000
gccacttggc ccaggtccct tctcataccg tcgtggcccg aagtatgggc ggcaaggagg   3060
acttgatctg ggagcttctc aaccaggccc aggaacattt tggcaaggac aagtccaagg   3120
agttccagct cttcagctct cctcatggga aggacctgct gtttaaggac tctgcccacg   3180
ggttcttgaa ggtcccccc aggatggatg ccaagatgta cctgggctat gagtatgtca     3240
ctgccatccg gaatctacgg gaaggcacat gcccagaagc cccaacagat gaatgcaagc   3300
ctgtgaagtg gtgtgcgctg agccaccacg agaggctcaa gtgtgatgag tggagtgtta   3360
acagtgtagg gaaaatagag tgtgtatcag cagagaccac cgaagactgc atcgccaaga   3420
tcatgaatgg agaagctgat gccatgagct tggatggagg gtttgtctac atagcgggca   3480
agtgtggtct ggtgcctgtc ctcgccgaga actacaacaa gagcgacaac tgtgaggata   3540
caccagaggc agggtatttt gctgtagcag tggtgaagaa atcagcttct gacctcacct   3600
gggacaatct gaaaggcaag aagtcctgcc atacggcaat tggcagaacc gctggctgga   3660
acatccccat gggcctgctc tacaataaga tcaaccactg ccgcttcgac gagttcttca   3720
gcgagggctg cgcccctggg tctaagaaag actccagtct ctgtaagctg tgtatgggct   3780
caggcctaaa cctgtgtgaa cccaacaaca agagggata ctacggctac acaggcgctt     3840
tcaggtgtct ggttgagaag ggagatgtgg ccttttgtgaa acaccagact gtcccacaga   3900
acactggggg aaagaaccct gatccatggg ctaagaacct gaacgagaag gactacgagc   3960
tcctgtgcct tgatggtacc aggaaacctg tggaggagta tgcgaactgc cacctggcca   4020
gagccccgaa tcacgctgtg gtcacacgga agataaggag agcttgcgtc acaagatat    4080
tacgtcaaca gcagcaccta tttggaagca acgtaactga ctgctcgggc aacttttgtt   4140
tgttccggtc ggaaaccaag gaccttctgt tcagagatga cacagtatgt ttggccaaac   4200
ttcatgacag aaacacctac gagaagtact gggcgagga gtacgtcaag gctgttggta   4260
acctgagaaa atgctccacc tcatcactcc tggaagctcg cactttccgt agaccttaat    4320
gattcgaagc gacttttgtc ccgaattcct gcagcccta gctagtcctt ccgatcgatg    4380
gaaggatccg tcggagctct acccttgcgg cgcgacatga taagatacat tgatgagttt   4440
ggacaaacca caactagaat gcagtgaaaa aaatgcttta tttgtgaaat ttgtgatgct    4500
attgctttat ttgtgaaatt tgtgatgcta ttgctttatt tgtaaccatt ataagctgca    4560
ataaacaagt taacaacaac aattgcattc attttatgtt tcaggttcag ggggaggtgt    4620
gggaggtttt ttaaagcaag taaaaacctct acaaatgtgg tagatcattt aaatgttaat    4680
tgtgtcgaca ggatcctata acttcgtata gcatacatta tacgaagtta tcagacaccc    4740
agtgtcgaac aacacctgac cgcgttgctg gcgttttcc ataggctccg cccccctgac     4800
gagcatcaca aaaatcgacg ctcaagtcag aggtggcgaa acccgacagg actataaaga    4860
taccaggcgt ttccccctgg aagctccctc gtgcgctctc ctgttccgac cctgccgctt    4920
accggatacc tgtccgcctt tctcccttcg ggaagcgtgg cgctttctca tagctcacgc    4980
tgtaggtatc tcagttcggt gtaggtcgtt cgctccaagc tgggctgtgt gcacgaaccc   5040
cccgttcagc ccgaccgctg cgccttatcc ggtaactatc gtcttgagtc aacccggta     5100
agacacgact tatcgccact ggcagcagcc actggtaaca ggattagcag agcgaggtat   5160
gtaggcggtg ctacagagtt cttgaagtgg tggcctaact acggctacac tagaaggaca   5220
gtatttggta tctgcgctct gctgaagcca gttaccttcg gaaaaagagt tggtagctcc   5280
tgatccggca acaaaccac cgctggtagc ggtggttttt tgtttgcaa gcagcagatt      5340
acgcgcagaa aaaaaggatc tcaagaagat cctttgatct tttctacggg gtctgacgct    5400
cagtggaacg aaaactcacg ttaagggatt ttggtcatga gattatcaaa aaggatcttc   5460
acctagatcc ttttaaatta aaaatgaagt tttaaatcaa tctaaagtat atatgagtaa   5520
acttggtctg acagttacca atgcttaatc agtgaggcac ctatctcagc gatctgtcta   5580
```

```
tttcgttcat ccatagttgc ctgactcccc gtcgtgtaga taactacgat acgggagggc   5640
ttaccatctg gccccagtgc tgcaatgata ccgcgagacc cacgctcacc ggctccagat   5700
ttatcagcaa taaaccagcc agccggaagg gccgagcgca gaagtggtcc tgcaacttta   5760
tccgcctcca tccagtctat taattgttgc cgggaagcta gagtaagtag ttcgccagtt   5820
aatagtttgc gcaacgttgt tgccattgct acaggcatcg tggtgtcacg ctcgtcgttt   5880
ggtatggctt cattcagctc cggttcccaa cgatcaaggc gagttacatg atcccccatg   5940
ttgtgcaaaa aagcggttag ctccttcggt cctccgatcg ttgtcagaag taagttggcc   6000
gcagtgttat cactcatggt tatggcagca ctgcataatt ctcttactgt catgccatcc   6060
gtaagatgct tttctgtgac tggtgagtac tcaaccaagt cattctgaga atagtgtatg   6120
cggcgaccga gttgctcttg cccggcgtca atacggtata taccgcgcc acatagcaga   6180
actttaaaag tgctcatcat tggaaaacgt tcttcggggc gaaaactctc aaggatctta   6240
ccgctgttga gatccagttc gatgtaaccc actcgtgcac ccaactgatc ttcagcatct   6300
tttactttca ccagcgtttc tgggtgagca aaaacaggaa ggcaaaatgc cgcaaaaaag   6360
ggaataaggg cgacacgaaa atgttgaata ctcatactct tccttttca atattattga   6420
agcatttatc agggttattg tctcatgagc ggatacatat ttgaatgtat ttagaaaaat   6480
aaacaaatag gggttccgcg cacatttccc cgaaaagtgc cacctgacgt ctaagaaacc   6540
attattatca tgacattaac ctataaaaat aggcgtatca cgaggccctt tcgtctcgcg   6600
cgtttcggtg atgacggtga aaacctctga cacatgcagc tcccggagac ggtcacagct   6660
tgtctgtaag cggatgccgg gagcagacaa gcccgtcagg gcgcgtcagc gggtgttggc   6720
gggtgtcggg gctggcttaa ctatgcggca tcagagcaga ttgtactgag agtgcaccat   6780
atgcggtgtg aaataccgca cagatgcgta aggagaaaat accgcatcag gcgtaccata   6840
acttcgtata aagtatccta tacgaagtta tccatatgtg acagtaggcc caagggtctc   6900
gacttaattt cgttcacctg ctattgtctt cccaatcctc cccttgctg tcctgcccca   6960
ccccaccccc cagaatagaa tgacacctac tcagacaatg cgatgcaatt tcctcatttt   7020
attaggaaag gacagtggga gtggcacctt ccagggtcaa ggaaggcacg ggggagggc    7080
aaacaacaga tggctggcaa ctagaaggca cagtcgaggc tgatcagcga tcgatgcagt   7140
catcagtcct gctcctcggc cacgaagtgc acgcagttgc cggccgggtc gcgcagggcg   7200
aactcccgcc cccacggctg ctcgccgatc tcggtcatgg ccggcccgga ggcgtcccgg   7260
aagttcgtgg acacgacctc cgaccactcg gcgtacagct cgtccaggcc gcgcaccac    7320
acccaggcca gggtgttgtc cggcaccacc tggtcctgga ccgcgctgat gaacagggtc   7380
acgtcgtccc ggaccacacc ggcgaagtcg tcctccacga agtcccggga gaacccgagc   7440
cggtcggtcc agaactcgac cgctccggcc acgtcgcgcg cggtgagcac cggaacggca   7500
ctggtcaact tggccatggt aagcttttg caaaagccta ggcctccaaa aaagcctcct   7560
cactacttct ggaatagctc agaggccgag gcggcctcgg cctctgcata aataaaaaaa   7620
attagtcagc catggggcgg agaatgggcg gaactgggcg gagttagggg cgggatgggc   7680
ggagttaggg gcgggactat ggttgctgac taattgagat gcatgctttg catacttctg   7740
cctgctgggg agcctgggga ctttccacac ctggttgctg actaattgag atgcatgctt   7800
tgcatacttc tgcctgctgg ggagcctggg gactttccac accctaactg acacacattc   7860
cacaggtcga ccactgtgct ggcgaattcc tactacggtc cccactag               7908
```

SEQ ID NO: 15         moltype = DNA   length = 10186
FEATURE               Location/Qualifiers
source                1..10186
                         mol_type = other DNA
                         organism = synthetic construct
SEQUENCE: 15

```
gtagatgtac tgccaagtag gaaagtccca taaggtcatg tactgggcat aatgccaggc     60
gggccattta ccgtcattga cgtcaatagg gggcgtactt ggcatatgat acacttgatg    120
tactgccaag tgggcagttt accgtaaata ctccacccat tgacgtcaat ggaaagtccc    180
tattggcgtt actatgggaa catacgtcat tattgacgtc aatgggcggg ggtcgttggg    240
cggtcagcca ggcgggccat ttaccgtaag ttatgtaacg cggaactcca tatatgggct    300
atgaactaat gaccccgtaa ttgattacta ttaataacta gccggttcaa ttgccgaccc    360
ctcccccaa cttctcgggg actgtgggcg atgtgcgctc tgcccactga cgggcaccgg    420
agctatatca agcttaccgc tatcggttgg aaaaccaacc gttcgcgtc tgtctggaca     480
ccgtcaacgg taaggacagc taccggacgc ggtcttaga cacaccgttg gcggttaggc    540
gtgccaccgt gatcggtaac tcatttcacc ggcaacggta tgggtacgaa ccgcctgcgg   600
tctatgtctg aaccgtgtcc ggtcagagtg gcgaccgctt ccggtgtcga cgtaccgggc   660
ccccctcga ggtcgacggt atcgataagc tagcttgata tatctagttc tagcgaattc    720
tagtaccctc gacctgcagg tcgatcgact ctagtatggt gcactctcag tacaatctgc   780
tctgatgccg catagttaag ccagtatctg ctccctgctt gtgtgttgga ggtcgctgag   840
tagtgcgcga gcaaaattta agctacaaca aggcaaggct tgaccgacaa ttgcatgaag   900
aatctgctta gggttaggcg ttttgcgctg cttcgcgatg tacgggccag atatacgcgt   960
atctgagggg actagggtgt gtttaggcga aaagcgggg ttcggttgta cgcggttagg   1020
agtccctca ggatatagta gtttgctttt gcatagggga ggaaatg tagtcttatg      1080
caatactctt gtagtcttgc aacatgtaa cgatgagtta gcaacatgcc ttacaaggag   1140
agaaaagca ccgtgcatgc cgattggtgg aagtaaggtg gtacgatcgt gccttattag    1200
gaaggcaaca gacgggtctg acatggattg gacgaaccac tgaattccgc attgcagaga   1260
tattgtattt aagtgcctag ctcgatacaa taaacgccat ttgaccattc accacattgg   1320
tgtgcacctc caagctggta gaggatcggt cgatcgactc tagacgccag aacacaggta   1380
agtgccgtgt gtggttcccg cgggcctggc ctctttacgg gttatggccc ttgcgtgcct   1440
tgaattactt ccacgcccct ggctgcagta cgtgattctt gatcccgagc ttcgggttgg   1500
aagtgggtgg gagagttcga ggccttgcgc ttaaggagcc ccttgcctc gtgcttgagt   1560
tgaggcctgg cttgggcgct ggggccgccg cgtgcgaatc tggtgcacc ttcgcgcctg    1620
tctcgctgct ttcgataagt ctctagccat ttaaaatttt tgatgacctg ctgcgacgct   1680
ttttttctgt caagatagtc ttgtaaatgc gggccaagat ctgcacactg gtatttcggt   1740
ttttggggcc gcgggcggcg acggggcccg tgcgtcccag cgcacatgtt cggcgaggcg   1800
gggcctgcga gcgcggccac cgagaatcgg acggggtag tctcaagctg gccggcctgc   1860
tctggtgcct ggcctcgcgc cgccgtgtat cgccccgccc tgggcggcaa ggctggcccg   1920
gtcggcacca gttgcgtgag cggaaagatg gccgcttccc ggccctgctg cagggagctc   1980
```

```
aaaatggagg acgcggcgct cgggagagcg ggcgggtgag tcacccacac aaaggaaaag      2040
ggcctttccg tcctcagccg tcgcttcatg tgactccacg gagtaccggg cgccgtccag      2100
gcacctcgat tagttctcga gcttttggag tacgtcgtct ttaggttggg gggaggggtt      2160
ttatgcgatg gagtttcccc acactgagtg ggtggagact gaagttaggc cagcttggca      2220
cttgatgtaa ttctccttgg aatttgccct ttttgagttt ggatcttggt tcattctcaa      2280
gcctcagaca gtggttcaaa gttttttttct tccatttcag gtgtcgtgtc tagagcggcc      2340
gccaccgaaa cgccgtaccg ccaccatgga gtggtcttgg gtgttcctgt tctttctgtc      2400
cgtgaccaca ggcgtccaca gcgaagtgca actggtggaa agcggcgag gactcgtcca       2460
acctggaggc tccctcagac tgtcctgcgc cgcgagcgga ttcaacatca aagacaccta      2520
tatccactgg gtcaggcaag cccctggcaa aggactggga tgggtcgcca ggatctaccc      2580
caccaatgga tacaccaggt acgctgacag cgtgaaaggc aggttcacaa tctccgccga      2640
caccagcaaa aacaccgcct atctccagat gaactccctg agggcgagg ataccgccgt        2700
ctactactgc agcaggtggg gaggcgacgg cttctacgcc atggattatt ggggacaagg      2760
caccctggtg accgtcagct ccgcttcgac caagggacct agcgtgttcc ctctggcccc      2820
cagcagcaag tctaccagcg gcggaacagc cgccctgggc tgcctggtca aggactactt      2880
ccccgagccc gtgaccgtgt cctgaacag cggagccctg acaagcggag tgcacacctt       2940
ccctgccgtg ctgcagtcca gcggcctgta tagcctgagc agcgtcgtga ccgtgcctag      3000
cagcagcctg ggcacccaga cctacatctg caacgtgaac cacaagccca gcaacaccaa      3060
ggtggacaag aaggtggagc ccaagagctg cgacaagacc catacctgcc cccttgtcc       3120
tgcccctgag ctgctgggcg gacccagcgt gtttctgttc cccccaagc caaggacac       3180
cctgatgatc agccggaccc ccgaagtgac ctgcgtggtg gtggatgtgt cccacgagga      3240
ccctgaagtg aagttcaatt ggtacgtgga cggcgtggag gtgcacaacg caagaccaa       3300
gccccgggag aacagtaca acagcaccta ccggtggtg tccgtgctga ccgtgctgca       3360
ccaggactgg ctgaacggca agaataacaa gtgcaaggtg tccaacaagg ccctgcctgc      3420
ccccatcgag aaaaccatca gcaaggccaa gggccagccc agagaacccc aggtgtacac      3480
cctgcctccc agcagagatg agctgaccaa gaaccaggtg tccctgacct gcctcgtgaa      3540
gggcttctac ccctccgata tcgccgtgga gtgggagagc aacggccagc ctgagaacaa      3600
ctacaagacc accccccctg tgctggatag cgacggcagc ttcttcctgt acagcaagct      3660
gaccgtggac aagagcagat ggcagcaggg caacgtgttc agctgcagcg tgatgcacga      3720
ggccctgcac aaccactaca cccagaagtc cctgagcctg agccccggca agtgatgaac      3780
cggtggcgcg cctagccggc cgcgacatga taagatacat tgatgagttt ggacaaacca      3840
caactagaat gcagtgaaaa aaatgcttta tttgtgaaat tgtgatgct attgctttat      3900
ttgtgaaatt tgtgatgcta ttgctttatt tgtaaccatt ataagctgca ataaacaagt      3960
taacaacaac aattgcattc attttatgtt tcaggttcag gggaggtgt ggggaggttt      4020
ttaaagcaag taaaacctct acaaatgtgg tagatcattt aaatgttaat tgtgtcgaca      4080
ggatcctata acttcgtata gcatacatta tacgaagtta tcagacaccc agtgtcgaac      4140
aacacctgac cgcgttgctg gcgttttcc ataggctccg cccccctgac gagcatcaca       4200
aaaatcgacg ctcaagtcag aggtggcgaa acccgacagg actataaaga taccaggcgt      4260
ttccccctgg aagctccctc gtgcgctctc ctgttccgac cctgccgctt accggatacc      4320
tgtccgcctt tctcccttcg ggaagcgtgg cgctttctca tagctcacgc tgtaggtatc      4380
tcagttcggt gtaggtcgtt cgctccaagc tgggctgtgt gcacgaaccc cccgttcagc      4440
ccgaccgctg cgccttatcc ggtaactatc gtcttgagtc aacccggta agacacgact       4500
tatcgccact ggcagcagcc actggtaaca ggattagcag agcgaggtat gtaggcggtg      4560
ctacagagtt cttgaagtgg tggcctaact acggctacac tagaaggaca gtatttggta      4620
tctgcgctct gctgaagcca gttaccttcg gaaaaagagt tggtagctct tgatccggca      4680
aacaaaccac cgctggtagc ggtggttttt tgttttgcaa gcagcagatt acgcgcagaa      4740
aaaaaggatc tcaagaagat cctttgatct ttttctacgg gtctgacgct cagtggaacg      4800
aaaactcacg ttaagggatt ttggtcatga gattatcaaa aaggatcttc acctagatcc      4860
ttttaaatta aaaatgaagt tttaaatcaa tctaaagtat atatgagtaa acttggtctg      4920
acagttacca atgcttaatc agtgaggcac ctatctcagc gatctgtcta tttcgttcat      4980
ccatagttgc ctgactcccc gtcgtgtaga taactacgat acgggagggc ttaccatctg      5040
gccccagtgc tgcaatgata ccgcgagacc cacgctcacc ggctccagat ttatcagcaa      5100
taaaccagcc agccggaagg gccgagcgca gaagtggtcc tgcaacttta tccgcctcca      5160
tccagtctat taattgttgc cgggaagcta gagtaagtag ttcgccagtt aatagtttgc      5220
gcaacgttgt tgccattgct acaggcatcg tggtgtcacg ctcgtcgttt ggtatggctt      5280
cattcagctc cggttcccaa cgatcaaggc gagttacatg atcccccatg ttgtgcaaaa      5340
aagcggttag ctccttcggt cctccgatcg ttgtcagaag taagttggcc gcagtgttat      5400
cactcatggt tatggcagca ctgcataatt ctcttactgt catgccatcc gtaagatgct      5460
tttctgtgac tggtgagtac tcaaccaagt cattctgaga atagtgtatg cggcgaccga      5520
gttgctcttg cccggcgtca atacgggata ataccgcgc acatagcaga acttttaaaag       5580
tgctcatcat tggaaaacgt tcttcggggc gaaaactctc aaggatctta ccgctgttga      5640
gatccagttc gatgtaaccc actcgtgcac ccaactgatc ttcagcatct tttactttca      5700
ccagcgtttc tgggtgagca aaaacaggaa ggcaaaatgc cgcaaaaaag ggaataaggg      5760
cgacacggaa atgttgaata ctcatactct tcctttttca atattattga agcatttatc      5820
agggttattg tctcatgagc ggatacatat ttgaatgtat ttagaaaaat aaacaaatag      5880
gggttccgcg cacatttccc cgaaaagtgc cacctgacgt ctaagaaacc attattatca      5940
tgacattaac ctataaaaat aggcgtatca cgaggccctt tcgtctcgcg cgtttcggtg      6000
atgacggtga aaacctctga cacatgcagc tcccggagac ggtcacagct tgtctgtaag      6060
cggatgccgg gagcagacaa gcccgtcagg gcgcgtcagc gggtgttggc gggtgtcggg      6120
gctggcttaa ctatgcggca tcagagcaga ttgtactgag agtgcaccat atgcggtgtg      6180
aaataccgca cagatgcgta aggagaaaat accgcatcag gcgtaccata acttcgtata      6240
aagtatccta tacgaagtta tccatatgtg acagtaggcc caagggtctc gacttaattt      6300
cgttcacctg ctattgtctt cccaatcctc cccttgctg tcctcccca ccccacccc         6360
cagaatagaa tgacacctac tcagacaatg cgatgcaatt tcctcatttt attaggaaag      6420
gacagtggga gtggcacctt ccagggtcaa ggaaggcacg gggaggggc aaacaacaga       6480
tggctggcaa ctagaaggca cagtcgaggc tgatcagcga tcgatgcatc atcagtcctg      6540
ctcctcggcc acgaagtgca cgcagttgcc ggccgggtcg cgcagggcga actcccgccc      6600
ccacggctgc tcgccgatct cggtcatggc cggcccggag gcgtcccgga agttcgtgga      6660
cacgacctcc gaccactcgg cgtacagctc gtccaggccg cgcacccaca cccaggccag      6720
```

-continued

```
ggtgttgtcc ggcaccacct ggtcctggac cgcgctgatg aacagggtca cgtcgtcccg   6780
gaccacaccg gcgaagtcgt cctccacgaa gtcccgggag aacccgagcc ggtcggtcca   6840
gaactcgacc gctccggcga cgtcgcgcgc ggtgagcacc ggaacggcac tggtcaactt   6900
ggccatggta agcttttgc aaaagcctag gcctccaaaa aagcctcctc actacttctg    6960
gaatagctca gaggccgagg cggcctcggc tctctgcataa ataaaaaaaa ttagtcagcc  7020
atggggcgga gaatgggcgg aactgggcgg agttaggggc gggatgggcg gagttagggg   7080
cgggactatg gttgctgact aattgagatg catgctttgc atacttctgc ctgctgggga   7140
gcctggggac tttccacacc tggttgctga ctaattgaga tgcatgcttt gcatacttct   7200
gcctgctggg gagcctgggg actttccaca ccctaactga cacacattcc acaggtcgac   7260
cactgtgctg gcgaattcct actacggtcc ccatggagcc taggaccag cgagcccgtc    7320
gccgccgcgg cggcgccgcc cggggggtctg cgagcagacc gaaaaggtca cactctgggg  7380
cgcgcgaccc gcccgagtca gcggcccgcc agttaccacc cgccgaccaa ccccgcct    7440
ccacggaggg cgggggggtg cttaagagga tcgcggcgct cttctgcgtg cccgtggcca   7500
ccaagaccaa accccgagcc gcctccgaat gagagtgttt cgttccttcc ccctccccgc   7560
gcgtcagaca aacccctaacc accgcttaag cggcccccgc gaggtccgaa gactcatttc  7620
gtactcgtcg acagcccaga ccccacgcaa cgcccaaaat aataaccccc acgaaccata   7680
aaccattccc catggggacc ccgtcctaa cccacggggc cagtggctat ggcagggcct    7740
gccgccccga cgttggctgc gagccctggg ccttcacccg aacttgggg gtgggggtgg   7800
gaaaaggaag aaacgcgggc gtattggccc caatggggtc tcgtgggg atcgacagag     7860
tgccagccct gggaccgaac cccgcgttta tgaacaaacg acccaacacc cgtgcgtttt   7920
attctgtctt tttattgccg tcatagcgcg ggttccttcc ggtattgtct ccttccgtgt   7980
ttcagttagc ctcccccatc tccttaatta agccggtcat cagcactcgc cccggttgaa   8040
gctcttggtc acggggctgg acaggccctg gtgggtcact tcgcaggcgt acaccttgtg   8100
cttctcgtag tcggccttgc tcagggtcag ggtgctgctc aggctgtagg tggagtcctt   8160
gctgtcctgc tcggtgacgc tttcctggct gttgccggac tgcagggcgt tgtccacctt   8220
ccactgcacc ttggcctccc ggggggtagaa gttgttcagc aggcacacga cgctggcggg   8280
gccggacttc agctgctcgt cgctgggggg gaagatgaac acgcttggag cagcaacggt   8340
tcgtttgatc tccaccttg tgccttggcc gaaggtgggg ggggttgtgt aatgctgctg    8400
gcagtagtag gtgcaaaat cctcgggttg caggctggag attgtcagtg tgaagtcggt    8460
tccggacctg gagccggaaa atctggaagg cacgccgcta tacaggaagg aggcgctata   8520
gatgagcagc ttgggagcct tgccaggttt ctgctggtac caagccacg ctgtgttcac    8580
atcctgctg gccctgcagg taatggtcac cctatctccc acggaagcgg acagggagga   8640
gggggactgt gtcatctgaa tgtcgcacct ggcgtctgtc agccacagca gcagcaggcc   8700
caggacctgg gtgggcacgg acatggtggc ttcgccgagc ttgtacgcta gaagggtacg   8760
gcgtttcggt ggcggccgct agatcggatc ctgcagaatt ccaccacact ggactagaat   8820
tctttgccaa aatgatgaga cagcacaata accagcacgt tgcccaggag ctgtaggaaa   8880
aagaagaagg catgaacatg gttagcagag gctctagagc cgccggtcac acgccagaag   8940
ccgaaccccg ccctgccccg tccccccga aggcagccgt cccccgcgg acagcccga     9000
ggctggagag ggagaagggg acggccgcgc ggcgacgcac gaaggccctc cccgcccatt   9060
tccttcctgc cggcgccgca ccgcttcgcc ccgcgcccgc tagagggggt gcggcggcgc   9120
ctcccagatt tcggctccgc acagatttgg gacaaaggaa gtcctgcgc cctctcgcac    9180
gattaccata aaaggcaatg gctgcggctc gccgcgcctc gacagccgcc ggcgctccgg   9240
gggccgcgc gcccctcccc cgagcctcc ccggcccgag gaggcccgc cccgccccgg     9300
accccccacct gccgccaccc ccgcccggc acgcgagcc ccgcgccacg ccccgtacgg    9360
agccccgcac ccgaagccgg gccgtgctca gcaactcggg gagggggtg cagggggggt   9420
tgcagcccga ccgacgcgcc cacaccccct gctcacccc ccacgcacac accccgcacg   9480
cagcctttgt tcccctcgca gccccccccg caccgcgggg accgcgcgc ggcgcgctc    9540
ccctcgcgca cactgcggag cgcacaaagc cccgcgccgc gcccgcagcg ctcacagccg   9600
ccgggcagcg cggagccgca cgcggcgctc cccacgcaca cacacacgca cgcacccccc   9660
gagccgctcc ccccgcacaa agggccctcc cggagcccct caaggctttc acgcagccac   9720
agaaaagaaa caagccgtca ttaaaccaag cgctaattac agcccggagg agaagggccg   9780
tcccgcccgc tcacctgtgg gagtaacgcg gtcagtcaga gccggggcgg gcggcgcgag   9840
gcggcggcg agcggggcac ggggcgaagg cagcgcgcag cgactccgc ccgccgcgcg    9900
cttcgctttt tataggggccg ccgccgccgc cgcctgccca taaaggaaa ctttcggagc   9960
gcgccgctct gattggctgc cgccgcacct ctccgcctcg ccccgccccg ccctcgccc   10020
cgccccgccc cgcctggcgc gcgcccccccc ccccgccccc catcgctgca caaaataatt  10080
aaaaaataaa taaatacaaa attggggggtg gggaggggg ggagatgggg agagtgaagc   10140
agaacgtggg gctcacctcg accatggtaa tagcgatgac taatac                  10186
```

| SEQ ID NO: 16 | moltype = AA length = 519 |
|---|---|
| FEATURE | Location/Qualifiers |
| source | 1..519 |
| | mol_type = protein |
| | organism = Homo sapiens |

SEQUENCE: 16

```
MLLLLLLLGL RLQLSLGIIP VEEENPDFWN REAAEALGAA KKLQPAQTAA KNLIIFLGDG    60
MGVSTVTAAR ILKGQKKDKL GPEIPLAMDR FPYVALSKTY NVDKHVPDSG ATATAYLCGV  120
KGNFQTIGLS AAARFNQCNT TRGNEVISVM NRAKKAGKSV GVVTTTRVQH ASPAGTYAHT  180
VNRNWYSDAD VPASARQEGC QDIATQLISN MDIDVILGGG RKYMFRMGTP DPEYPDDYSQ  240
GGTRLDGKNL VQEWLAKRQG ARYVWNRTEL MQASLDPSVT HLMGLFEPGD MKYEIHRDST  300
LDPSLMEMTE AALRLLSRNP RGFFLFVEGG RIDHGHHESR AYRALTETIM FDDAIERAGQ  360
LTSEEDTLSL VTADHSHVFS FGGYPLRGSS IFGLAPGKAR DRKAYTVLLY GNGPGYVLKD  420
GARPDVTESE SGSPEYRQQS AVPLDEETHA GEDVAVFARG PQAHLVHGVQ EQTFIAHVMA  480
FAACLEPYTA CDLAPPAGTT DAAHPGYSRV GAAGRFEQT                        519
```

| SEQ ID NO: 17 | moltype = AA length = 24 |
|---|---|
| FEATURE | Location/Qualifiers |
| source | 1..24 |
| | mol_type = protein |

```
                        organism = Foot-and-mouth disease virus
SEQUENCE: 17
APVKQTLNFD LLKLAGDVES NPGP                                          24

SEQ ID NO: 18          moltype = AA   length = 344
FEATURE                Location/Qualifiers
source                 1..344
                       mol_type = protein
                       organism = synthetic construct
SEQUENCE: 18
KKPELTATSV EKFLIEKFDS VSDLMQLSEG EESRAFSFDV GGRGYVLRVN SCADGFYKDR    60
YVYRHFASAA LPIPEVLDIG EFSESLTYCI SRRAQGVTLQ DLPETELPAV LQPVAEAMDA   120
IAAADLSQTS GFGPFGPQGI GQYTTWRDFI CAIADPHVYH WQTVMDDTVS ASVAQALDEL   180
MLWAEDCPEV RHLVHADFGS NNVLTDNGRI TAVIDWSEAM FGDSQYEVAN IFFWRPWLAC   240
MEQQTRYFER RHPELAGSPR LRAYMLRIGL DQLYQSLVDG NFDDAAWAQG RCDAIVRSGA   300
GTVGRTQIAR RSAAVWTDGC VEVLADSGNR RPSTRPDREM GEAN                    344

SEQ ID NO: 19          moltype = AA   length = 185
FEATURE                Location/Qualifiers
source                 1..185
                       mol_type = protein
                       organism = synthetic construct
SEQUENCE: 19
MGVKVLFALI CIAVAEAKPT ENNEDFNIVA VASNFATTDL DADRGKLPGK KLPLEVLKEM    60
EANARKAGCT RGCLICLSHI KCTPKMKKFI PGRCHTYEGD KESAQGGIGE AIVDIPEIPG   120
FKDLEPMEQF IAQVDLCVDC TTGCLKGLAN VQCSDLLKKW LPQRCATFAS KIQGQVDKIK   180
GAGGD                                                               185

SEQ ID NO: 20          moltype = AA   length = 241
FEATURE                Location/Qualifiers
source                 1..241
                       mol_type = protein
                       organism = synthetic construct
SEQUENCE: 20
FEMVSKGEEL FTGVVPILVE LDGDVNGHKF SVSGEGEGDA TYGKLTLKFI CTTGKLPVPW    60
PTLVTTLTYG VQCFSRYPDH MKQHDFFKSA MPEGYVQERT IFFKDDGNYK TRAEVKFEGD   120
TLVNRIELKG IDFKEDGNIL GHKLEYNYNS HNVYIMADKQ KNGIKVNFKI RHNIEDGSVQ   180
LADHYQQNTP IGDGPVLLPD NHYLSTQSAL SKDPNEKRDH MVLLEFVTAA GITLGMDELY   240
K                                                                   241

SEQ ID NO: 21          moltype = AA   length = 550
FEATURE                Location/Qualifiers
source                 1..550
                       mol_type = protein
                       organism = synthetic construct
SEQUENCE: 21
MEDAKNIKKG PAPFYPLEDG TAGEQLHKAM KRYALVPGTI AFTDAHIEVD ITYAEYFEMS    60
VRLAEAMKRY GLNTNHRIVV CSENSLQFFM PVLGALFIGV AVAPANDIYN ERELLNSMGI   120
SQPTVVFVSK KGLQKILNVQ KKLPIIQKII IMDSKTDYQG FQSMYTFVTS HLPPGFNEYD   180
FVPESFDRDK TIALIMNSSG STGLPKGVAL PHRTACVRFS HARDPIFGNQ IIPDTAILSV   240
VPFHHGFGMF TTLGYLICGF RVVLMYRFEE ELFLRSLQDY KIQSALLVPT LFGFFAKSTL   300
IDKYDLSNLH EIASGGAPLS KEVGEAVAKR FHLPGIRQGY GLTETTSAIL ITPEGDDKPG   360
AVGKVVPFFE AKVVDLDTGK TLGVNQRGEL CVRGPMIMSG YVNNPEATNA LIDKDGWLHS   420
GDIAYWDEDE HFFIVDRLKS LIKYKGYQVA PAELESILLQ HPNIFDAGVA GLPDDDAGEL   480
PAAVVVLEHG KTMTEKEIVD YVASQVTTAK KLRGGVVFVD EVPKGLTGKL DARKIREILI   540
KAKKGGKIAV                                                          550

SEQ ID NO: 22          moltype = DNA   length = 181
FEATURE                Location/Qualifiers
source                 1..181
                       mol_type = other DNA
                       organism = synthetic construct
SEQUENCE: 22
accgttgccg gtcggatctg taccgttgcc ggtcggatct gtaccgttgc cggtcggatc    60
tgtaccgttg ccggtcggat ctgtaccgtt gccggtcgga tctgtaccgt tgccggtcgg   120
atctgtaccg ttgccggtcg gatctgtacc gttgccggtc ggatctgtac cgttgccggt   180
c                                                                   181

SEQ ID NO: 23          moltype = DNA   length = 210
FEATURE                Location/Qualifiers
source                 1..210
                       mol_type = other DNA
                       organism = synthetic construct
SEQUENCE: 23
agcttcagaa gatggcggag ggcctccaac acagtaattt tcctcccgac agatctccta    60
gaatgtttcc acccaatcat tactatgaca acagctgttt tttttagtat taagcagagg   120
ccgggggccc ctggcctccg cttactctgg agaaaaagaa gagaggcatt gtagaggctt   180
ccagaggcaa cttgtcaaaa caggactggc                                    210
```

```
SEQ ID NO: 24          moltype = DNA   length = 622
FEATURE                Location/Qualifiers
source                 1..622
                       mol_type = other DNA
                       organism = synthetic construct
SEQUENCE: 24
taatgttgcc atgggtagca tatactaccc aaatatctgg atagcatatg ctatcctaat   60
ctatatctgg gtagcatagg ctatcctaat ctatatctgg gtagcatatg ctatcctaat  120
ctatatctgg gtagtatatg ctatcctaat ttatatctgg gtagcatagg ctatcctaat  180
ctatatctgg gtagcatatg ctatcctaat ctatatctgg gtagtatatg ctatcctaat  240
ctgtatccgg gtagcatatg ctatcctaat agagattagg gtagtatatg ctatcctaat  300
ttatatctgg gtagcatata ctacccaaat atctggatag catatgctat cctaatctat  360
atctgggtag catatgctat cctaatctat atctgggtag cataggctat cctaatctat  420
atctgggtag catatgctat cctaatctat atctgggtag tatatgctat cctaatttat  480
atctgggtag cataggctat cctaatctat atctgggtag catatgctat cctaatctat  540
atctgggtag tatatgctat cctaatctgt atccgggtag catatgctat cctcatgcgt  600
atacagtcag catatgatac cc                                           622

SEQ ID NO: 25          moltype = DNA   length = 194
FEATURE                Location/Qualifiers
source                 1..194
                       mol_type = other DNA
                       organism = synthetic construct
SEQUENCE: 25
gtaagtggcg tttctcgggg agccagctgc gtccgctgtc gtgctgtcgg tgtagtacta   60
gcaagcgtta agtccccatc tggctgcggc ctaccgaaga gtggtcttca cgtcacacgc  120
tgtcccacgc acgtggttgg tttggtcgct tctggttact gactactaag cagcctttc   180
tttttccctt tcag                                                    194

SEQ ID NO: 26          moltype = DNA   length = 258
FEATURE                Location/Qualifiers
source                 1..258
                       mol_type = other DNA
                       organism = synthetic construct
SEQUENCE: 26
cgacatgata agatacattg atgagtttgg acaaaccaca actagaatgc agtgaaaaaa   60
atgctttatt tgtgaaattt gtgatgctat tgctttattt gtgaaatttg tgatgctatt  120
gctttatttg taaccattat aagctgcaat aaacaagtta acaacaacaa ttgcattcat  180
tttatgtttc aggttcaggg ggaggtgtgg gaggtttttt aaagcaagta aaacctctac  240
aaatgtggta gatcattt                                                258
```